(12) United States Patent
Folk et al.

(10) Patent No.: US 12,390,479 B2
(45) Date of Patent: *Aug. 19, 2025

(54) NITRIC OXIDE-RELEASING ANTIBACTERIAL COMPOUNDS, FORMULATIONS, AND METHODS PERTAINING THERETO

(71) Applicant: KNOW BIO, LLC, Durham, NC (US)

(72) Inventors: Drew Folk, Durham, NC (US); Ryan Gerald Anderson, Morrisville, NC (US); John Kelly Simons, Cary, NC (US); Mona Jasmine Rosales Ahonen, Durham, NC (US); Rebecca Anthouard McDonald, Chapel Hill, NC (US)

(73) Assignee: KNOW BIO, LLC, Durham, NC (US)

( * ) Notice: Subject to any disclaimer, the term of this patent is extended or adjusted under 35 U.S.C. 154(b) by 935 days.

This patent is subject to a terminal disclaimer.

(21) Appl. No.: 17/312,321

(22) PCT Filed: Feb. 5, 2021

(86) PCT No.: PCT/US2021/016854
§ 371 (c)(1),
(2) Date: Jun. 9, 2021

(87) PCT Pub. No.: WO2021/158941
PCT Pub. Date: Aug. 12, 2021

(65) Prior Publication Data
US 2022/0160736 A1    May 26, 2022

Related U.S. Application Data

(60) Provisional application No. 62/971,624, filed on Feb. 7, 2020.

(51) Int. Cl.
A61K 31/655    (2006.01)
A01N 33/12    (2006.01)
(Continued)

(52) U.S. Cl.
CPC ............ A61K 31/655 (2013.01); A01N 33/12 (2013.01); A01N 51/00 (2013.01); A01N 59/06 (2013.01);
(Continued)

(58) Field of Classification Search
None
See application file for complete search history.

(56) References Cited

U.S. PATENT DOCUMENTS 5,910,316 A    6/1999  Keefer
11,813,270 B2 * 11/2023  Folk ....................... A61K 33/06
(Continued)

OTHER PUBLICATIONS

Amati et al. The biology of pulmonary exacerbations in bronchiectasis. Eur Respir Rev 2019; 28: 190055 (Year: 2019).*
(Continued)

Primary Examiner — Jeffrey S Lundgren
Assistant Examiner — Anthony Joseph Seitz
(74) Attorney, Agent, or Firm — David S. Bradin; Maynard Nexsen PC

(57) ABSTRACT

Several embodiments of NO releasing compounds are disclosed. In some embodiments, the structures are covalently modified to store and release nitric oxide. Some embodiments pertain to methods of making and use of these structures. The compounds may be tailored to release nitric oxide in a controlled manner and can be useful, for example, for treating or preventing microbial infections, or reducing the microbial load of a microbial infection.

15 Claims, 10 Drawing Sheets

(51) Int. Cl.
*A01N 51/00* (2006.01)
*A01N 59/06* (2006.01)
*A01P 1/00* (2006.01)
*A61K 33/02* (2006.01)
*A61K 33/06* (2006.01)
*A61K 33/24* (2019.01)
*A61K 39/42* (2006.01)
*A61K 45/06* (2006.01)
*A61P 31/00* (2006.01)

(52) U.S. Cl.
CPC ............... *A01P 1/00* (2021.08); *A61K 33/02* (2013.01); *A61K 33/06* (2013.01); *A61K 33/24* (2013.01); *A61K 39/42* (2013.01); *A61K 45/06* (2013.01); *A61P 31/00* (2018.01)

(56) References Cited

U.S. PATENT DOCUMENTS

2005/0203069 A1  9/2005  Arnold et al.
2009/0042819 A1* 2/2009  Ellis .................. A61P 31/12
                                                540/355
2012/0269897 A1  10/2012 Chen et al.

OTHER PUBLICATIONS

Jeong et al., Mol Pharm. Feb. 3, 2020;17(2):656-665. Epub Jan. 22, 2020 (Year: 2020).*
International Search Report and Written Opinion issued in counterpart PCT Application No. PCT/US2021/016854 dated Jun. 24, 2021 (twelve (12) pages).
Arulsamy et al. 2001. "Multiplicity Control in the Polygeminal Diazeniumdiolation of Active Hydrogen Bearing Carbons: Chemistry of a New Type of Trianionic Molecular Propeller." J. Am. Chem. Soc. vol. 123, pp. 10860-10869.
PubChem-CID-135525507, Create Date: Jan. 15, 2019, p. 2.
Jeong, Hyjoong, et al. "Sustained nitric oxide-providing small molecule and precise release behavior study for glaucoma treatment." Mol. Pharmaceutics. Publication date Jan. 8, 2020.

* cited by examiner

Reaction Product $^1$H NMR

NITRIC OXIDE-RELEASING ANTIBACTERIAL COMPOUNDS, FORMULATIONS, AND METHODS PERTAINING THERETO

CROSS-REFERENCE TO RELATED APPLICATIONS

The present patent application is a 35 U.S.C. § 371 U.S. national phase entry of International Application PCT/US2021/016854 having an international filing date of Feb. 5, 2021, which claims the benefit and priority of U.S. Provisional Patent Application No. 62/971,624, filed on Feb. 7, 2020, titled "NITRIC OXIDE-RELEASING ANTIBACTERIAL COMPOUNDS, FORMULATIONS, AND METHODS PERTAINING THERETO," the contents of which are hereby incorporated by reference in their entireties.

FIELD

The present disclosure relates generally to nitric oxide-releasing compounds, their synthesis, and their use as antimicrobial compounds. Antimicrobial compositions comprising these compounds and their methods of use are also disclosed.

BACKGROUND

Respiratory viruses include rhinoviruses and enteroviruses (Picornaviridae), influenza viruses (Orthomyxoviridae), parainfluenza, metapneumoviruses and respiratory syncytial viruses (Paramyxoviridae), coronaviruses (Coronaviridae), and several adenoviruses, and these also pose a great challenge to human health. Further, exposure to respiratory viruses often results in a secondary bacterial infection.

Bacterial infections pose a great challenge to human health in community and hospital settings, and antibacterial resistance is leading to multi-drug resistant bacteria that are becoming increasingly difficult to treat.

Biofilms are cooperative communities of bacteria encapsulated by an exopolysaccharide (EPS) matrix protecting the bacteria from host immune response and antibiotics. Bacteria growing in biofilms are typically more resistant to antibiotics and disinfectants than planktonic cells, and the resistance increases with the age of the biofilm. Bacterial biofilm also exhibits increased physical resistance towards desiccation, extreme temperatures or light, and conventional antibiotic treatment is often ineffective at treating biofilms.

Conventional treatments for microbial infections typically involve systemic administration of antimicrobials (antibiotics or antivirals), which can lead to drug resistance and a number of adverse effects from loss of hearing to gastrointestinal distress. It would be advantageous to have alternative treatments for microbial infections that used an orthogonal mechanism of action to treat microbial infections.

Nitric oxide is known for having such an orthogonal antimicrobial mechanism of action. See, e.g., U.S. Patent Application Publication No. 2019/0322770. While the precise mechanisms by which nitric oxide (NO) kills or inhibits the replication of a variety of intracellular pathogens is not completely understood, reactivity towards iron centers involved in cellular metabolism, the imposition of nitrosative stress, and activation of host immunity are likely implicated. Nitric oxide is also understood to target cysteine proteases (Saura et al., Immunity, Volume 10, Issue 1, 1 Jan. 1999, Pages 21-28). NO S-nitrosylates the cysteine residue in the active site of certain viral proteases, inhibiting protease activity and interrupting the viral life cycle. Since cysteine proteases are critical for virulence or replication of many viruses, bacteria, and parasites, NO can be used to treat microbial infections. While long seen as a potentially beneficial therapeutic, the administration of NO gas via inhalation is difficult and time-consuming and antimicrobial levels are close to therapeutic levels, leaving little safety interval.

NO-releasing compounds (i.e., NO donors) have been proposed as therapeutics, often in the form of polymers with side-chains that include nitric oxide-releasing moieties, such as nitrosothiols and diazeniumdiolates. Nitric oxide-releasing polymers have heretofore been underused as therapeutics, based at least in part on limited NO payloads, NO release rates that are more rapid than desired, and the lack of targeted NO delivery.

It would be advantageous to have pharmaceutical compositions comprising NO donors to deliver antimicrobial concentrations of NO to a patient. It would also be advantageous to have additional compounds, compositions, and methods for treating microbial infections, particularly compounds and methods that are effective at treating drug resistant microbes, and at treating biofilms. The present invention provides such compounds, compositions, and methods.

SUMMARY

Nitric oxide, an endogenously produced diatomic free radical, is associated with numerous biological processes. Exogenous NO delivery can be an effective strategy for treating or preventing microbial infections. Nitric oxide-releasing compounds (also referred to as nitric oxide donors or NO donors), compositions containing such compounds, and methods of treating microbial infections using the compounds and compositions, are disclosed.

In one embodiment, the compounds disclosed herein have the following formula:

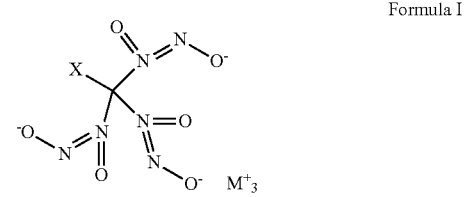

Formula I wherein:
X is selected from the group consisting of H, D, R, and RC(O)—,
R is $C_{1-12}$ alkyl, aryl, heteroaryl, alkylaryl, or arylalkyl, optionally substituted with one or more substituents as defined herein,
and $M^+$ is a pharmaceutically-acceptable cation.

In some embodiments, $M^+$ is a cation with a valence other than one, for example, $^{+2}$ or $^{+3}$, in which case the ratio of the compound of Formula I to the cation is such that the total positive charge equals the total negative charge. So, for a compound with a total charge of negative three, and a cation with a total charge of positive two, there would be two compounds and three cations.

Representative positively charged cations include sodium, potassium, lithium, calcium, magnesium, and quaternary ammonium salts.

Methods for making these compounds are also disclosed. In one embodiment, compounds with an R(CO)— moiety that does not include acidic α C—H (i.e., alpha to the carbonyl), such as aryl, heteroaryl, and branched alkyl groups, like t-butyl groups, can be prepared by reacting all acidic α C—H on the methyl group of a compound with the formula $R(CO)CH_3$ with nitric oxide in basic methanol to give trisdiazeniumdiolates. A representative reaction is shown below:

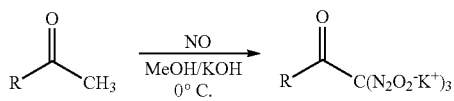

By way of example, the reaction product of acetophenone with nitric oxide in KOH/methanol is:

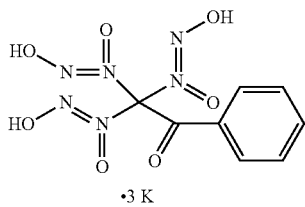 [SMILES: O=C(c1ccccc1)C(/[N+]([O-])=N/O)(/[N+]([O-])=N/O)/[N+]([O-])=N/O]

In another embodiment, compounds where X is H or D can be prepared by reacting acetone with nitric oxide in basic methanol or deuterated methanol to give tris-diazeniumdiolates.

In another embodiment, the NO-releasing compound has the structure of Formula II:

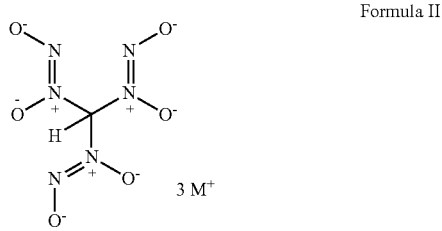

Formula II where $M^+$ is as defined above with respect to Formula I.

In some embodiments, the cation is sodium, lithium, potassium, or a quaternary ammonium salt.

The compounds of Formula II can be prepared, for example, by reacting acetone, acetonitrile, or ethanol with NO, optionally at high pressures (i.e., pressures above atmospheric pressure, ideally above about 2 ATM of pressure, and preferably above about 10 ATM of pressure) in the presence of a base, such as a methoxide/methanol solution, to form one or more diazeniumdiolate-containing species. In several embodiments, high purity compounds (greater than about 80%, greater than about 90%, greater than about 95%, or greater than about 98%) can be produced according to the methods disclosed herein.

In still another embodiment, the NO-releasing compound has the structure of Formula III:

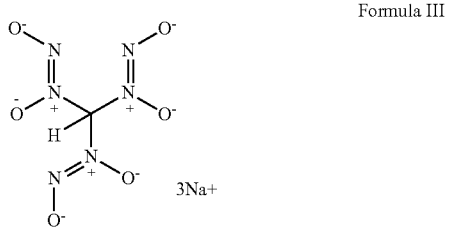

Formula III

In some embodiments, the compounds of any of Formulas I, II or III have a purity in excess of 96%, in excess of 97%, in excess of 98%, in excess of 99%, or in excess of 99.5%. The present disclosure also relates to compounds having this purity level.

In one embodiment, the nitric oxide-releasing compound has a NO-release half-life, at normal physiological temperature and pH, of between 0.1 and 24 hours. In another embodiment, the NO-release half-life is at least 15 minutes. In some embodiments, the compound has a total releasable NO storage in a range of 2-10 μmol of NO per mg of NO donor compound. In several embodiments, the compound has a total duration of NO release in the range of 1-60 hours. In several embodiments, the total NO release after 4 hours is in the range between 0.1-1.0 μmol of NO per mg of compound.

The compounds can be formulated in a variety of pharmaceutical compositions, for delivery intravenously, via inhalation, via nebulization, via intranasal administration, via oral administration, via injection, via rectal or vaginal administration, and via topical administration.

In one embodiment, the pharmaceutical compositions comprise one or more nitric oxide-releasing compounds described herein and an aqueous solution. In one aspect of this embodiment, the nitric oxide releasing compound has an aqueous solubility of at least about 25 mg/ml in the aqueous solution, at a physiologically compatible pH.

The pharmaceutical compositions can further include one or more additional active agents, depending on the type of microbial infection to be treated. For example, where the infection is a bacterial, viral, or fungal infection, one or more antibacterial, antiviral, or antifungal compounds can be present. Anti-inflammatory compounds can also be present.

In some embodiments, the compositions can further include one or more of a chelating agent, a mucoadhesive agent, or a low molecular weight polyethylene glycol.

In one embodiment, the compositions further include a gallium salt.

In certain embodiments, the small molecule nitric oxide donors are provided in dilute solutions (e.g., for nebulization, vaporization or inhalation), and in other embodiments, are provided in the form of gels or viscous liquids, for example, for topical administration.

Methods for treating microbial infections are also disclosed. In some embodiments, the methods involve delivering nitric oxide to a subject in need of antimicrobial treatment, by delivering the compounds of any of Formulas I, II or III, and having the compound degrade upon exposure to physiological pH and temperature to release nitric oxide. In some embodiments, the amount of the compounds that is administered is an effective amount of the compounds, or compositions including the compounds, to bring about the desired antimicrobial effect, namely, treatment, prevention, or reduction in the microbial load.

Representative microbes include viruses, Gram-positive bacteria, Gram-negative bacteria, drug-resistant bacteria, molds, yeasts, fungi, and combinations thereof. In some embodiments, the microbes include one, two, or more of the following: gram-positive bacteria, gram-negative bacteria, drug-resistant bacteria, fungi, yeast, and viruses.

While not wishing to be bound by a particular theory, it is believed that the compounds generate nitric oxide and induce oxidative and/or nitrosative damage to microbial DNA and membrane structures, thereby treating the microbial infections, preventing the microbial infections, reducing microbial load by reducing the number of viable microbes and/or preventing the colonization or infection with microbes. In some embodiments, a NO-donor of the compound or composition generates NO and induces damage to the membrane and/or DNA of the microbes.

Representative microbial infections include bacterial, fungal, and viral infections, specifically including those which result in gastrointestinal disorders, respiratory disorders, and sexually transmitted diseases.

Representative viral infections that can be treated include those associated with one or more of human immunodeficiency virus, herpes simplex virus, papilloma virus, parainfluenza virus, influenza, hepatitis, Coxsackie Virus, herpes zoster, measles, mumps, rubella, rabies, pneumonia, hemorrhagic viral fevers, H1N1, SARS, MERS, and SARS-CoV2. Representative fungal infections that caq be treated include those associated with mold, including black mold, *Candida albicans, Aspergillus niger.*

Representative bacterial infections that can be treated include *Escherichia coli, Pseudomonas aeruginosa,* and *Staphylococcus aureus,* Group A streptococci, *S. pneumoniae, Mycobacterium tuberculosis, Campylobacter jejuni, Salmonella, Shigella,* carbapenem-resistant Enterobacteriaceae Methicillin-resistant *Staphylococcus aureus,* and *Burkholderia cepacia.* In several embodiments, the microbial load comprises Methicillin-resistant *Staphylococcus aureus.* In several embodiments, the microbial load comprises carbapenem-resistant Enterobacteriaceae. In several embodiments, the microbial load comprises *Staphylococcus aureus.* In several embodiments, the microbial load comprises *Pseudomonas aeruginosa.* In several embodiments, the microbial load comprises *Burkholderia cepacia.*

In some embodiments, the microbe is a parasite.

In several embodiments, the microbial infection being treated is present on an organic surface, such as human or animal skin, including epithelial tissue, or a wound surface. In several embodiments, the application does not induce skin irritation. The skin surface can be, for example, in the mouth or surrounding tissues (e.g., lips, nasal nares, teeth, gums, etc.), the oral mucosa, any portion of the digestive tract, or the lungs or any other part of the respiratory tract.

In several embodiments, the effective amount of the compounds or compositions is administered as a solution via nebulization. In several embodiments, the subject is a patient who has suffered a lung infection and the compounds are administered to treat, and, ideally, to eliminate the infection.

In several embodiments, the subject has an infection of the gastrointestinal tract or another tissue or organ and a composition of the present disclosure is administered as an anti-infective agent. Several chronic infections, such as those associated with implanted devices, chronic wounds, and cystic fibrosis, are frequently caused by biofilm-forming pathogens such as *Pseudomonas aeruginosa* and *Staphylococcus aureus.* Biofilms are cooperative communities of bacteria encapsulated by an exopolysaccharide (EPS) matrix protecting the bacteria from host immune response and antibiotics. It has been reported that eradication of biofilms may require up to 1000 times higher antibiotic concentrations relative to those needed for plankton bacteria. Resistant respiratory infections are particularly difficult to treat because they form protective biofilms inside airway mucus and can survive for decades. There exists a need in the art for new antibacterial compositions because of the resistance of biofilms to conventional antibacterial agents.

Gallium has been reported to possess both antimicrobial and immunosuppressant effects. Activity towards viruses (Narayanasamy, et al., "Prolonged-acting, Multi-targeting Gallium Nanoparticles Potently Inhibit Growth of Both HIV and Mycobacteria in Co-Infected Human Macrophages," Sci Rep 5, 8824 (2015)) has been demonstrated. Likewise, gallium damages key iron-dependent enzymes in bacteria (See Goss, et al., "Gallium disrupts bacterial iron metabolism and has therapeutic effects in mice and humans with lung infections," Sci Transl Med. 2018; 10(460):eaat7520), which has led to the use of gallium citrate as a pharmaceutical product (AR-501 by Aridis). Gallium has been studied against planktonic, biofilm, and in vivo PA (See Kaneko, et al., J Clin Invest., 2007; 117(4):877-888). Tested against planktonic and macrophage-grown non-tuberculosis mycobacteria (NTM), gallium has shown some promise for the treatment of chronic infections (See Abdalla et al, Antimicrob Agents Chemother. 2015; 59(8):4826-4834).

A combination of gallium and one or more of the nitric-oxide donor compounds described herein can produce a synergistic anti-microbial effect, for example, against biofilms, which are notoriously difficult to treat with conventional antimicrobial compositions. These combinations can further include a siderophore. Compositions comprising gallium, at least one nitric oxide donor compound described herein, and, optionally, at least one siderophore, also exhibit synergistic effects against plankton bacteria and biofilms.

The compositions and related methods set forth in further detail below describe certain actions taken by a practitioner; however, it should be understood that they can also include the instructions of those actions by another party. Thus, actions such as "administering a NO-donating compound" include "instructing the administration of a NO-donating compound."

The embodiments discussed above will be better understood with reference to the following detailed description.

DETAILED DESCRIPTION

Figure 1:
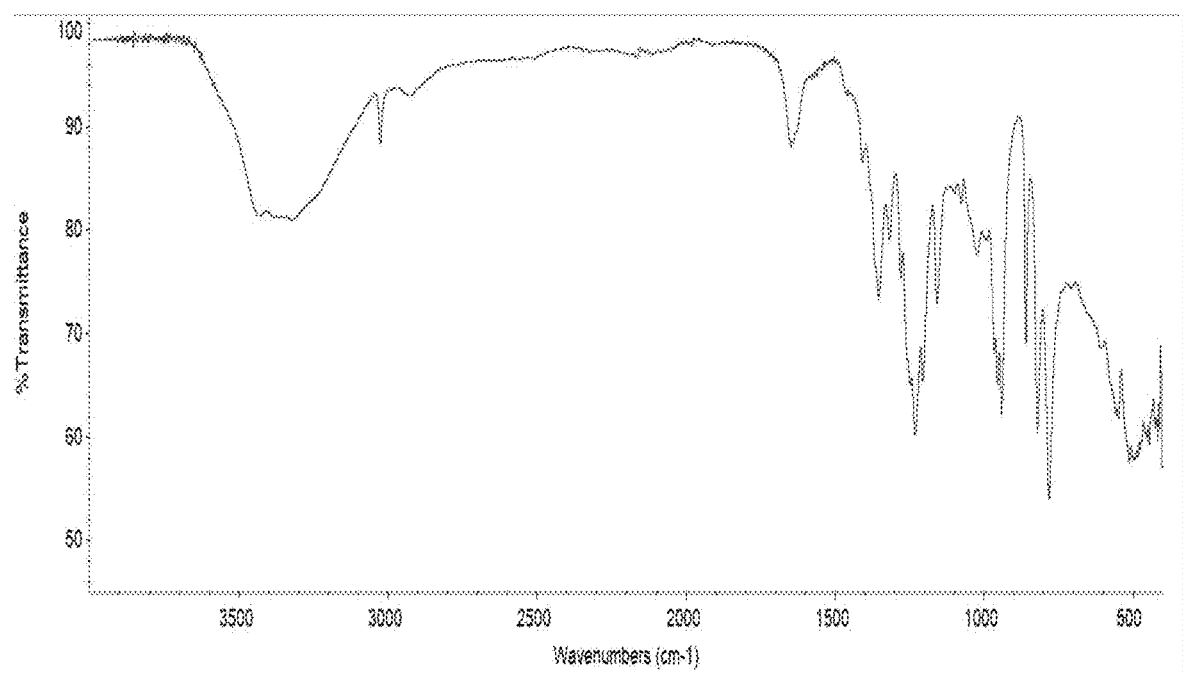
FIG. 1 shows the FTIR spectrum of the compound of Formula III.

Nitric oxide (NO) is antimicrobial, but its role as a therapeutic has heretofore been underused, based at least in part on limited NO payloads of therapeutic compositions, NO release rates that are more rapid than desired, and a lack of targeted NO delivery.

NO-releasing compounds, compositions comprising such compounds, methods of producing such compounds and compositions, and methods of treating or preventing microbial infections, or reducing microbial load, are disclosed. In some embodiments, the compounds are present in pharmaceutical compositions with desired physical properties, such as viscosity and gelation.

The compounds are small molecules, i.e., have a molecular weight below around 500 g/mol, and, in some embodiments, around 200 g/mol, not including the associated cation. One of the advantages of using small molecules over polymers is that the compounds can be prepared with relatively lower impurity levels than polymeric compounds. Further, relative to polymeric compounds, the NO load can be higher, because the percent composition ratio between NO to the scaffold can be maximized, as described herein.

Small molecule precursor compounds, which can be converted to the NO-releasing compounds described herein, can be selected with a relatively low number of reactive groups, for example, a hydrogens adjacent a carbonyl group, reducing the possibility that many different species will result from a nitrosation reaction. As a result, nitrosylation of the NO-precursor can proceed with little or no partial reaction products, which provides the potential for relatively pure products.

Knowing the structure of the small molecule allows for more predictable release kinetics than that obtainable with polymers. Additionally, and desirably, the cation associated with the negatively charged diazenium ions can be selected such that it also has desirable properties. For example, quaternary ammonium salts also have antimicrobial properties.

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The present invention will be better understood with reference to the following definitions.

Definitions

Unless otherwise defined, all technical and scientific terms used herein have the same meaning as commonly understood by one of ordinary skill in the art to which this subject matter belongs. The terminology used in the description of the subject matter herein is for the purpose of describing particular embodiments only and is not intended to be limiting of the subject matter.

The term "effective amount," as used herein, refers broadly to that amount of a recited compound effective to treat, prevent, or reduce the microbial load in a subject afflicted with a microbial infection. This includes improving the subject's condition (e.g., in one or more symptoms), delaying or reducing the progression of the infection, preventing or delaying the onset of the infection, and/or changing clinical parameters, disease or illness, etc., as would be well known in the art.

For example, an effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In some embodiments, an improvement in a condition can be a reduction in infection. In some embodiments, an improvement can be reduction of bacterial load (e.g., bioburden) on a surface or in a subject. Actual dosage levels of active ingredients in an active composition of the presently disclosed subject matter can be varied so as to administer an amount of the active compound(s) that is effective to achieve the desired response for a particular subject. The selected dosage level will depend upon a variety of factors including, but not limited to, the activity of the composition, formulation, route of administration, combination with other drugs or treatments, severity of the condition being treated, and the physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are contemplated herein.

"Treat" or "treating" or "treatment" refers broadly to any type of action that imparts a desired antimicrobial effect, including treating or preventing a microbial infection, reducing the microbial load, improving the condition of the subject (e.g., in one or more symptoms), delaying or reducing the progression of the infection, and/or changing one or more clinical parameters.

The terms "disrupting" and "eradicating" refer broadly to the ability of the presently disclosed structures to combat biofilms. The biofilms may be partially eradicated or disrupted, meaning that the cells no longer attach to one another or to a surface. The biofilm may be completely eradicated, meaning that the biofilm is no longer an interconnected, cohesive, or continuous network of cells to a substantial degree.

The terms "nitric oxide donor" or "NO donor" refer broadly to species and/or molecules that donate, release and/or directly or indirectly transfer a nitric oxide species, and/or stimulate the endogenous production of nitric oxide in vivo and/or elevate endogenous levels of nitric oxide in vivo, such that the biological activity of the nitric oxide species is expressed at the intended site of action.

The terms "nitric oxide releasing" or "nitric oxide donating" refer to species that donate, release and/or directly or indirectly transfer any one (or two or more) of the three redox forms of nitrogen monoxide (NO+, NO−, NO (e.g., •NO)) and/or methods of donating, releasing and/or directly or indirectly transferring any one (or two or more) of the three redox forms of nitrogen monoxide (NO+, NO−, NO). In some embodiments, the nitric oxide releasing is accomplished such that the biological activity of the nitrogen monoxide species is expressed at the intended site of action.

The term "microbial infection" as used herein refers broadly to bacterial, fungal, viral, yeast infections, as well other microorganisms, and combinations thereof.

The term "respiratory tract" includes not only the lungs, but also the mouth, nasal passages, throat, esophagus, larynx, pharynx, and trachea. Within the lungs, therapy can be targeted to one or more of the bronchioles, bronchi, upper airways, and lower airways. The therapeutic approaches described herein can be used to treat or prevent, slow the progression or, or reverse the damage associated with, a number of different types of respiratory disorders. Certain respiratory disorders are associated with microbial infection, and the compounds used to treat the disorders can produce nitric oxide in concentrations effective for killing the microbes. Certain respiratory disorders, such as COPD, emphysema, and both acute and chronic bronchitis, are associated with poor vascularization, and/or can benefit from increased vascularization. Exogenous nitric oxide, released as the compounds described herein undergo degradation, can increase vascularization, so can be particularly effective in treating such disorders.

The "patient" or "subject" treated as disclosed herein is, in some embodiments, a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" as used herein includes, but is not limited to, humans, non-human primates, cattle, sheep, goats, pigs, horses, cats, dog, rabbits, rodents (e.g., rats or mice), monkeys, etc. Human subjects include neonates, infants, juveniles, adults and geriatric subjects. The subject "in need of" the methods disclosed herein can be a subject that is experiencing a disease state and/or is anticipated to experience a disease state, and the methods and compositions of the invention are used for therapeutic and/or prophylactic treatment.

For the general chemical formulas provided herein, if no substituent is indicated, a person of ordinary skill in the art will appreciate that the substituent is hydrogen. A bond that is not connected to an atom, but is shown, indicates that the position of such substituent is variable. A jagged line, wavy line, two wavy lines drawn through a bond or at the end of a bond indicates that some additional structure is bonded to that position. For a great number of the additional monomers disclosed herein, but not explicitly shown in structures, it is understood by those in the art of polymers, that these monomers can be added to change the physical properties of the resultant polymeric materials even where the elemental analysis would not indicate such a distinction could be expected. Such physical properties include solubility, charge, stability, cross-linking, secondary and tertiary structure, and the like. Moreover, if no stereochemistry is indicated for compounds having one or more chiral centers, all enantiomers and diasteromers are included. Similarly, for a recitation of aliphatic or alkyl groups, all structural isomers thereof also are included. Unless otherwise stated, groups shown as $A_1$ through $A_n$ and referred to herein as an alkyl group, in the general formulas provided herein are independently selected from alkyl or aliphatic groups, particularly alkyl having 20 or fewer carbon atoms, and even more typically lower alkyl having 10 or fewer atoms, such as methyl, ethyl, propyl, isopropyl, and butyl. The alkyl may be optionally substituted (e.g., substituted or not substituted, as disclosed elsewhere herein). The alkyl may be a substituted alkyl group, such as alkyl halide (e.g. $-CX_3$ where X is a halide, and combinations thereof, either in the chain or bonded thereto), alcohols (e.g. aliphatic or alkyl hydroxyl, particularly lower alkyl hydroxyl) or other similarly substituted moieties such as amino-, amino acid-, aryl-, alkyl aryl-, alkyl ester-, ether-, keto-, nitro-, sulfhydryl-, sulfonyl-, sulfoxide modified-alkyl groups.

The term "amino" and "amine" refer to nitrogen-containing groups such as $NR_3$, $NH_3$, $NHR_2$, and $NH_2R$, wherein R can be as described elsewhere herein. Thus, "amino" as used herein can refer to a primary amine, a secondary amine, or a tertiary amine. In some embodiments, one R of an amino group can be a diazeniumdiolate (e.g., NONO).

Whenever a group is described as being "optionally substituted" that group may be unsubstituted or substituted with one or more of the indicated substituents. Likewise, when a group is described as being "unsubstituted or substituted" (or "substituted or unsubstituted") if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, nitro, sulfenyl, sulfinyl, sulfonyl, haloalkyl, haloalkoxy, an amino, a mono-substituted amine group, a di-substituted amine group, a mono-substituted amine(alkyl), a di-substituted amine(alkyl), a diamino-group, a polyamino, a diether-group, and a polyether-group.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" or "$C_1$-$C_4$ alkyl" group refers broadly to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

As used herein, the term "alkyl" refers broadly to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers broadly to each integer in the given range; e.g., "1 to 30 carbon atoms" means that the alkyl group may consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, although the present definition also covers the occurrence of the term "alkyl" where no numerical range is designated). The "alkyl" group may also be a medium size alkyl having 1 to 12 carbon atoms. The "alkyl" group could also be a lower alkyl having 1 to 6 carbon atoms. An alkyl group may be substituted or unsubstituted. By way of example only, "$C_1$-$C_5$ alkyl" indicates that there are one to five carbon atoms in the alkyl chain, e.g., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl.

As used herein, the term "alkylene" refers broadly to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by ~~, followed by the number of carbon atoms, followed by a "*". For example,

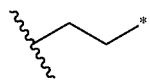

to represent ethylene. The alkylene group may have 1 to 30 carbon atoms (whenever it appears herein, a numerical range such as "1 to 30" refers broadly to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 6 carbon atoms. An alkylene group may be substituted or unsubstituted. For example, a lower alkylene group can be substituted by replacing one or more hydrogens of the lower alkylene group and/or by substituting both hydrogens on the same carbon with a $C_{3-6}$ monocyclic cycloalkyl group (e.g.,

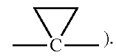

The term "alkenyl" used herein refers broadly to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers broadly to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers broadly to a completely saturated (no double or triple bonds) mono- or multi-cyclic (such as bicyclic) hydrocarbon ring system. When composed of two or more rings, the rings may be joined together in a fused, bridged or spiro fashion. As used herein, the term "fused" refers broadly to two rings which have two atoms and one bond in common. As used herein, the term "bridged cycloalkyl" refers broadly to compounds wherein the cycloalkyl contains a linkage of one or more atoms connecting non-adjacent atoms. As used herein, the term "spiro" refers broadly to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "cycloalkenyl" refers broadly to a mono- or multi-cyclic (such as bicyclic) hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s), 3 to 8 atoms in the ring(s) or 3 to 6 atoms in the ring(s). When composed of two or more rings, the rings may be connected together in a fused, bridged, or spiro fashion. A cycloalkenyl group may be unsubstituted or substituted.

As used herein, "aryl" refers broadly to a carbocyclic (all carbon) monocyclic or multicyclic (such as bicyclic) aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted. As used herein, "heteroaryl" refers to a monocyclic or multicyclic (such as bicyclic) aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers broadly to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s) or 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "aralkyl" and "aryl(alkyl)" refer broadly to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "cycloalkyl(alkyl)" refer broadly to an cycloalkyl group connected, as a substituent, via a lower alkylene group. The lower alkylene and cycloalkyl group of a cycloalkyl(alkyl) may be substituted or unsubstituted.

As used herein, "heteroaralkyl" and "heteroaryl(alkyl)" refer broadly to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrolylalkyl, pyridylalkyl, isoxazolylalkyl and imidazolylalkyl and their benzo-fused analogs.

A "heteroalicyclyl(alkyl)" and "heterocyclyl(alkyl)" refer broadly to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

As used herein, the term "hydroxy" refers broadly to a —OH group.

As used herein, "alkoxy" refers broadly to the Formula —OR wherein R is an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers broadly to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

As used herein, a "cyano" group refers broadly to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers broadly to a "—C(=S)R" group in which R can be the same as defined with respect to O-carboxy. A thiocarbonyl may be substituted or unsubstituted. An "O-carbamyl" group refers to a "—OC(=O)N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers broadly to an "ROC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers broadly to a "—OC(=S)—N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers broadly to an "ROC(=S)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers broadly to a "—C(=O)N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers broadly to a "RC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

An "S-sulfonamido" group refers broadly to a "—$SO_2$N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers broadly to a "R$SO_2$N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers broadly to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer broadly to a "—C(=O)OR" group in which R can be the same as defined with respect to O-carboxy. An ester and C-carboxy may be substituted or unsubstituted.

A "nitro" group refers broadly to an "—$NO_2$" group.

A "sulfenyl" group refers broadly to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers broadly to an "—S(=O)—R" group in which R can be the same as defined with respect to sulfenyl. A sulfinyl may be substituted or unsubstituted.

A "sulfonyl" group refers broadly to an "$SO_2$R" group in which R can be the same as defined with respect to sulfenyl. A sulfonyl may be substituted or unsubstituted.

As used herein, "haloalkyl" refers broadly to an alkyl group in which one or more of the hydrogen atoms are replaced by a halogen (e.g., mono-haloalkyl, di-haloalkyl, tri-haloalkyl and polyhaloalkyl). Such groups include but are not limited to, chloromethyl, fluoromethyl, difluoromethyl, trifluoromethyl, 1-chloro-2-fluoromethyl, 2-fluoroisobutyl and pentafluoroethyl. A haloalkyl may be substituted or unsubstituted.

As used herein, "haloalkoxy" refers broadly to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The terms "amino" and "unsubstituted amino" as used herein refer broadly to a —$NH_2$ group.

A "mono-substituted amine" group refers broadly to a "—NH$R_A$" group in which $R_A$ can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. The $R_A$ may be substituted or unsubstituted. A mono-substituted amine group can include, for example, a mono-alkylamine group, a mono-$C_1$-$C_6$ alkylamine group, a mono-arylamine group, a mono-$C_6$-$C_{10}$ arylamine group and the like. Examples of mono-substituted amine groups include, but are not limited to, —NH(methyl), —NH(phenyl) and the like.

A "di-substituted amine" group refers broadly to a "—N$R_A R_B$" group in which $R_A$ and $R_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. $R_A$ and $R_B$ can independently be substituted or unsubstituted. A di-substituted amine group can include, for example, a di-alkylamine group, a di-$C_1$-$C_6$ alkylamine group, a di-arylamine group, a di-$C_6$-$C_{10}$ arylamine group and the like. Examples of di-substituted amine groups include, but are not limited to, —N(methyl)$_2$, —N(phenyl)(methyl), —N(ethyl)(methyl) and the like.s used herein, "mono-substituted amine(alkyl)" group refers broadly to a mono-substituted amine as provided herein connected, as a substituent, via a lower alkylene group. A mono-substituted amine(alkyl) may be substituted or unsubstituted. A mono-substituted amine(alkyl) group can include, for example, a mono-alkylamine(alkyl) group, a mono-$C_1$-$C_6$ alkylamine($C_1$-$C_6$ alkyl) group, a mono-arylamine(alkyl group), a mono-$C_6$-$C_{10}$ arylamine ($C_1$-$C_6$ alkyl) group and the like. Examples of mono-substituted amine(alkyl) groups include, but are not limited to, —$CH_2$NH(methyl), —$CH_2$NH(phenyl), —$CH_2CH_2$NH (methyl), —$CH_2CH_2$NH(phenyl) and the like.

As used herein, "di-substituted amine(alkyl)" group refers broadly to a di-substituted amine as provided herein connected, as a substituent, via a lower alkylene group. A di-substituted amine(alkyl) may be substituted or unsubstituted. A di-substituted amine(alkyl) group can include, for example, a dialkylamine(alkyl) group, a di-$C_1$-$C_6$ alkylamine($C_1$-$C_6$ alkyl) group, a di-arylamine(alkyl) group, a di-$C_6$-$C_{10}$ arylamine($C_1$-$C_6$ alkyl) group and the like. Examples of di-substituted amine(alkyl)groups include, but are not limited to, —$CH_2$N(methyl)$_2$, —$CH_2$N(phenyl)(methyl), —$CH_2$N(ethyl)(methyl), —$CH_2CH_2$N(methyl)$_2$, $CH_2CH_2$N(phenyl)(methyl), —$NCH_2CH_2$(ethyl)(methyl) and the like.

As used herein, the term "diamino-" denotes a "—N($R_A$)$R_B$—N($R_C$)($R_D$)" group in which $R_A$, $R_C$, and $R_D$ can be independently a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein $R_B$ connects the two "N" groups and can be (independently of $R_A$, $R_C$, and $R_D$) a substituted or unsubstituted alkylene group. $R_A$, $R_B$, $R_C$, and $R_D$ can independently further be substituted or unsubstituted.

As used herein, the term "polyamino" denotes a "—(N($R_A$)$R_B$—)$_n$—N($R_C$)($R_D$)". For illustration, the term polyamino can comprise —N($R_A$)alkyl-N($R_A$)alkyl-N($R_A$)alkyl-N($R_A$)alkyl-H. In some embodiments, the alkyl of the polyamino is as disclosed elsewhere herein. While this example has only 4 repeat units, the term "polyamino" may consist of 1, 2, 3, 4, 5, 6, 7, 8, 9, or 10 repeat units. $R_A$, $R_C$, and $R_D$ can be independently a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein $R_B$ connects the two "N" groups and can be (independently of $R_A$, $R_C$, and $R_D$) a substituted or unsubstituted alkylene group. $R_A$, $R_C$, and $R_D$ can independently further be substituted or unsubstituted. As noted here, the polyamino comprises amine groups with intervening alkyl groups (where alkyl is as defined elsewhere herein).

As used herein, the term "diether-" denotes an "—O$R_B$O—$R_A$" group in which $R_A$ can be a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein $R_B$ connects the two "O" groups and can be a substituted or unsubstituted alkylene group. $R_A$ can independently further be substituted or unsubstituted.

As used herein, the term "polyether" denotes a repeating —(O$R_B$—)$_n$O$R_A$ group. For illustration, the term polyether can comprise —Oalkyl-Oalkyl-Oalkyl-Oalkyl-O$R_A$. In some embodiments, the alkyl of the polyether is as disclosed elsewhere herein. While this example has only 4 repeat units, the term "polyether" may consist of 1, 2, 3, 4, 5, 6, 7, 8, 9, or 10 repeat units. $R_A$ can be a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. $R_B$ can be a substituted or unsubstituted alkylene group. $R_A$ can independently further be substituted or unsubstituted. As noted here, the polyether comprises ether groups with intervening alkyl groups (where alkyl is as defined elsewhere herein and can be optionally substituted).

Where the number of substituents is not specified (e.g. haloalkyl), there may be one or more substituents present. For example, "haloalkyl" may include one or more of the same or different halogens. As another example, "$C_1$-$C_3$ alkoxyphenyl" may include one or more of the same or different alkoxy groups containing one, two or three atoms. As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

When a range of integers is given, the range includes any number falling within the range and the numbers defining ends of the range. For example, when the terms "integer from 1 to 20" is used, the integers included in the range are 1, 2, 3, 4, 5, 6, 7, 8, 9, 10, etc., up to and including 20.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 one millipascal-second" includes "10 one millipascal-second."

Also as used herein, "and/or" refers broadly to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount. The term "consists essentially of" (and grammatical variants), shall be given its ordinary meaning and shall also mean that the composition or method referred to can contain additional components as long as the additional components do not materially alter the composition or method. The term "consists of" (and grammatical variants), shall be given its ordinary meaning and shall also mean that the composition or method referred to is closed to additional components. The term "comprising" (and grammatical variants), shall be given its ordinary meaning and shall also mean that the composition or method referred to is open to contain additional components.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Compounds

As disclosed elsewhere herein, some embodiments disclosed herein pertain to small molecules capable of delivering NO to achieve microbicidal activity. In some embodiments, the cations present in the small molecules have antimicrobial or other desired physiological properties. In some embodiments, the compounds are water-soluble.

In one embodiment, provided herein is a NO releasing compound which exhibits potent antimicrobial characteristics, comprising the structure of Formula I:

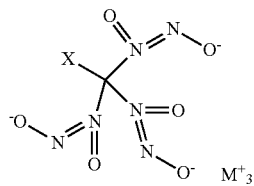

Formula I wherein:
X is selected from the group consisting of H, D, R, and RC(O)—,
R is $C_{1-12}$ alkyl, aryl, heteroaryl, alkylaryl, or arylalkyl, optionally substituted with one or more substituents, wherein the substituents are independently selected from the group consisting of —OH, —NH$_2$, —OCH$_3$, —C(O)OH, —CH$_2$OH, —CH$_2$OCH$_3$, —CH$_2$OCH$_2$CH$_2$OH, —OCH$_2$C(O)OH, —CH$_2$OCH$_2$C(O)OH, —CH$_2$C(O)OH, —NHC(O)—CH$_3$, —C(O)O((CH$_2$)$_a$O)$_b$—H, —C(O)O((CH$_2$)$_a$O)$_b$—(CH$_2$)$_c$H, —C(O)O(C$_{1-5}$alkyl), —C(O)—NH—((CH$_2$)$_d$NH)$_e$—H, —C(O)—NH—((CH$_2$)$_d$NH)$_e$—(CH$_2$)$_f$H, —O—((CH$_2$)$_a$O)$_b$—H, —O—(CH$_2$)$_a$O)$_b$—(CH$_2$)$_c$H, —O—(C$_{1-5}$alkyl), —NH—((CH$_2$)$_d$NH)$_e$—H, and —NH—((CH$_2$)$_d$NH)$_e$—(CH$_2$)$_f$H, each instance of a, b, c, d, e, f, g, h, i, j, k, and l is independently selected from an integer of 0, 1, 2, 3, 4, 5, 6, 7, 8, 9, or 10, and M$^+$ is a pharmaceutically-acceptable cation.

In some embodiments, M$^+$ is a cation with a valence other than one, for example, $^{+2}$ or $^{+3}$, in which case the ratio of the compound of Formula I to the cation is such that the total positive charge equals the total negative charge. So, for a compound with a total charge of negative three, and a cation with a total charge of positive two, there would be two compounds and three cations.

Representative positively charged cations include sodium, potassium, lithium, calcium, magnesium, and quaternary ammonium salts.

In another embodiment, the compound has the following structure:

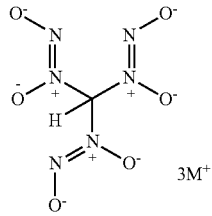

Formula II wherein M$^+$ refers to a pharmaceutically-acceptable cation. The cation can be any pharmaceutically acceptable, non-toxic cation known to those skilled in the art, including but not limited to sodium, potassium, lithium, calcium, magnesium, ammonium, or substituted ammonium. It will be appreciated by those skilled in the art that when the cation (M) has a valency greater than one, the ratio of negative charge in the methyl trisdiazenium diolate moiety to the positive charge in the cation will balance out. For example, if the cation (M) has a charge of +2, then there is a ratio of 2 methyl trisdiazenium diolate moieties to three M$^{+2}$ ions, and if the cation (M) has a charge of +3, then there is a 1/1 ratio of cation to methyl trisdiazenium diolate.

One representative compound is shown below:

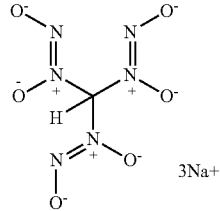

Formula III

Formula II is also described as a methane trisdiazeniumdiolate (MTDD), and Formula III as methane trisdiazeniumdiolate sodium salt.

Although various NO donors (e.g., diazeniumdiolates, S-nitrosothiols, metal nitrosyls, organic nitrates) are known to provide for controlled exogenous NO delivery, the diazeniumdiolate moieties in the compounds disclosed herein are attractive because of their good stability and facile storage, and because they spontaneously undergo proton-triggered dissociation under physiological conditions to regenerate nitric oxide, including NO radicals.

The C-diazeniumdiolates described herein are pH-triggered NO-release donors. Reacting with protons under physiological conditions (e.g., 37° C., pH 7.4), 1 mole of Formula III generates two moles of NO radicals and 2 to 3 moles of nitroxyl compounds.

Several embodiments disclosed herein have one or more of the following advantages: efficient and unique synthesis routes and resultant chemical composition of small molecules.

In several embodiments, the NO-releasing compounds are stable at a variety of temperatures 20° C. (e.g., 40° C., 45° C., 55° C., 60° C., 80° C., etc.) and are stable for prolonged storage periods (e.g., 10 hours, 20 hours, 22 hours, 25 hours, 30 hours, etc., days such as 1 day, 3 days, 5 days, 6 days, 7 days, 15 days, 30 days, 45 days, etc., weeks such as 1 week, 2 weeks, 3 weeks, 4 weeks, 6 weeks, 8 weeks, etc., months such as 1 month, 2 months, 3 months, 4 months, 5 months, 6 months, etc., or even years (1 year or greater)).

In some embodiments, the compounds have NO storage capacities (in μmol NO/mg of the compounds) of greater than or equal to about: 0.25, 0.4, 0.5, 1.0, 1.5, 2.0, 3.0, or ranges including and/or spanning the aforementioned values. In some embodiments, within 2 h of being added to a PBS buffer solution, the compounds release greater than or equal to about: 25%, 50%, 75%, 85%, 90%, 95%, 100%, or ranges including and/or spanning the aforementioned values, their total wt % of bound NO. In several embodiments, NO release in use for reducing or eliminating a biofilm occurs in similar amounts, e.g., about 20-25%, about 30-50%, about 60-75%, at least 80%, at least 85%, at least 90%, at least 95%, ranges including and/or spanning the aforementioned values, of the total wt % of bound NO.

In some embodiments, the NO release may occur over a period of about 0.01 hours, 0.1 hours, 0.25 hours, 0.5 hours, 1 hour, 2 hours, 3 hours, 4 hours, 5 hours, 10 hours, 15 hours, 20 hours, 24 hours, 36 hours, 48 hours, 60 hours, or ranges including and/or spanning the aforementioned values. In several embodiments, the NO release half-life is equal to or at least about: 0.01 hours, 0.1 hours, 0.25 hours, 0.5 hours, 1 hour, 2 hours, 3 hours, 4 hours, 5 hours or ranges including and/or spanning the aforementioned values. In some embodiments, the NO release occurs in less than or equal to about: 0.01 hours, 0.1 hours, 0.25 hours, 0.5 hours, 1 hour, 2 hours, 3 hours, 4 hours, 5 hours, 10 hours, 15 hours, 20 hours, 24 hours or ranges including and/or spanning the aforementioned values.

In some embodiments, the compounds have a degradation rate per hour in an amylase enzyme exposure assay of less than or equal to about: 0.2%, 0.5%, 1.0%, 1.5%, 2.5%, 5.0%, 10%, or ranges including and/or spanning the aforementioned values.

In some embodiments, the compounds have antimicrobial activity. In some embodiments, the compounds can efficiently eradicate or reduce the viability of microbes (e.g., prokaryotic cells, bacteria, viruses, protozoa, fungi, algae, amoebas, slime molds, etc., including drug-resistant microbes) with low toxicity to native tissue and patient cells (e.g., eukaryotic cells, mammalian cells, human cells, etc.).

In some embodiments, the compounds provide greater than or equal to 90% bacterial reduction in a bacterial viability assay performed under static conditions over 2 hours against one or more of *P. aeruginosa, S. aureus P. gingivalis, A. actinomycetemcomitans, A. viscosus,* and/or *S. mutans* at a concentration of equal to or less than about: 4 mg/ml, 2 mg/ml, 1 mg/ml, 0.5 mg/ml, 0.1 mg/ml, 0.05 mg/ml or ranges including and/or spanning the aforementioned values. In some embodiments, the disclosed functionalized NO-releasing compounds provide greater than or equal to 99% bacterial reduction and/or a 2 to 3 log reduction in a bacterial viability assay performed under static conditions over 2 hours against a gram positive bacteria at a concentration of equal to or less than about: 4 mg/ml, 2 mg/ml, 1 mg/ml, 0.5 mg/ml, 0.1 mg/ml, 0.05 mg/ml or ranges including and/or spanning the aforementioned values. In some embodiments, the disclosed functionalized NO-releasing polymers provide greater than or equal to 99% bacterial reduction and/or a 2 to 3 log reduction in a bacterial viability assay performed under static conditions over 2 hours against a gram negative bacteria at a r concentration of equal to or less than about: 4 mg/ml, 2 mg/ml, 1 mg/ml, 0.5 mg/ml, 0.1 mg/ml, 0.05 mg/ml or ranges including and/or spanning the aforementioned values. In several embodiments, bacterial reduction is greater than 95%, greater than 98%, or greater than 99%.

II. Compound Synthesis

Several embodiments disclosed herein provide the synthesis and characterization of the diazeniumdiolate NO donor-modified compounds described herein. The synthesis of compounds capable of controlled NO storage and release is important for taking advantage of NO's role in physiology and for developing NO-based therapeutics.

Several embodiments disclosed herein have one or more of the following advantages: efficient and unique synthesis routes and resultant chemical composition of constructs. Certain compounds described herein have been previously disclosed, but the present disclosure describes their synthesis and utility in pharmaceutical compositions and methods of treating or preventing microbial infections, or reducing microbial loads.

There are a number of ways to make the compounds of Formula I. In one embodiment, compounds with an R(CO)— moiety that does not include acidic α C—H (i.e., alpha to the carbonyl), such as aryl, heteraryl, and branched alkyl groups, like t-butyl groups, can be prepared by reacting all acidic α C—H on the methyl group of a compound with the formula R(CO)CH$_3$ with nitric oxide in basic methanol to give trisdiazeniumdiolates. A representative reaction is shown below:

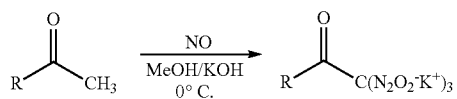

By way of example, the reaction product of acetophenone with nitric oxide in KOH/methanol is:

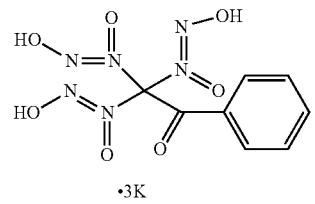 [SMILES: O=C(c1ccccc1)C(/[N+]([O-])=N/O)(/[N+]([O-])=N/O)/[N+]([O-])=N/O]

In another embodiment, compounds where X is H or D can be prepared by reacting acetone with nitric oxide in basic methanol or deuterated methanol to give tris-diazeniumdiolates.

Formula II can be prepared via a number of different approaches, including the reaction of ethanol, acetonitrile, or acetone with nitric oxide gas, in the presence of a basic methanol solution. Ideally, the nitric oxide gas is present at a pressure greater than atmospheric pressure, more ideally, greater than two atmospheres of pressure, and, preferably, greater than ten atmospheres of pressure. Higher pressures help ensure complete reaction. Where there is an incomplete reaction, one of the by-products of the reaction is methane bis-diazeniumdiolate:

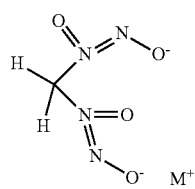

Methane bis-diazeniumdiolate does not release NO or NHO under physiological conditions.

Figure 8:
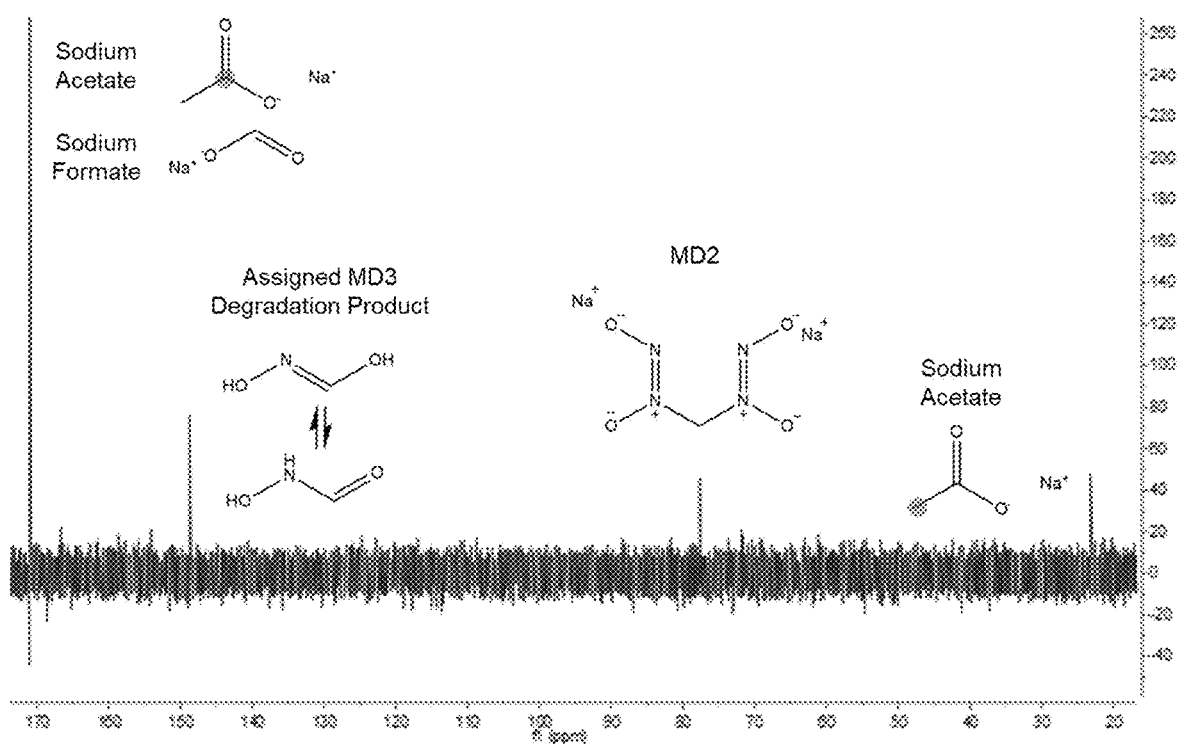
FIG. 8 is a $^{13}$C NMR spectrum of the reaction products when compound of Formula III was neutralized (pH 7) at room temperature.

The reaction of acetone with nitric oxide, at relatively high pressures, in the presence of basic methanol solutions such as sodium or potassium hydroxide in methanol, tends to provide the purest compound. The $^{13}$C NMR for methane tris-diazenium diolate prepared using this approach are shown in FIG. 8, and as can be seen in the figure, there is one product peak.

The proposed reaction mechanism behind this reaction, using sodium hydroxide in methanol to provide the compound where M$^+$ is Na$^+$, is provided below:

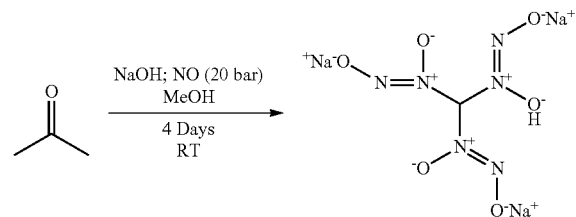

NO-dimer formation:

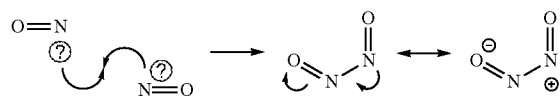

MD3 Formation

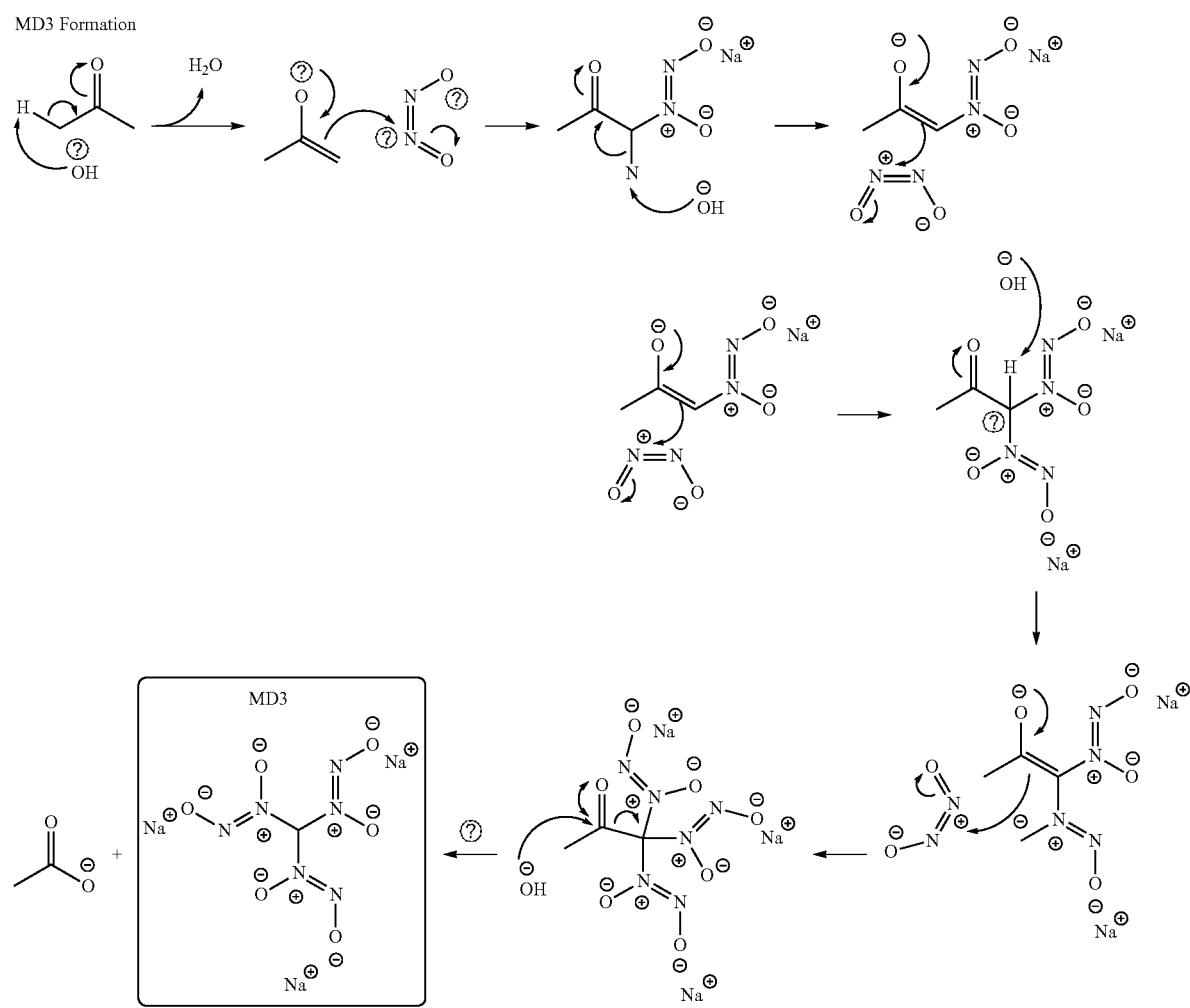

The following proposed mechanism relates to the degradation of this compound to form nitric oxide:

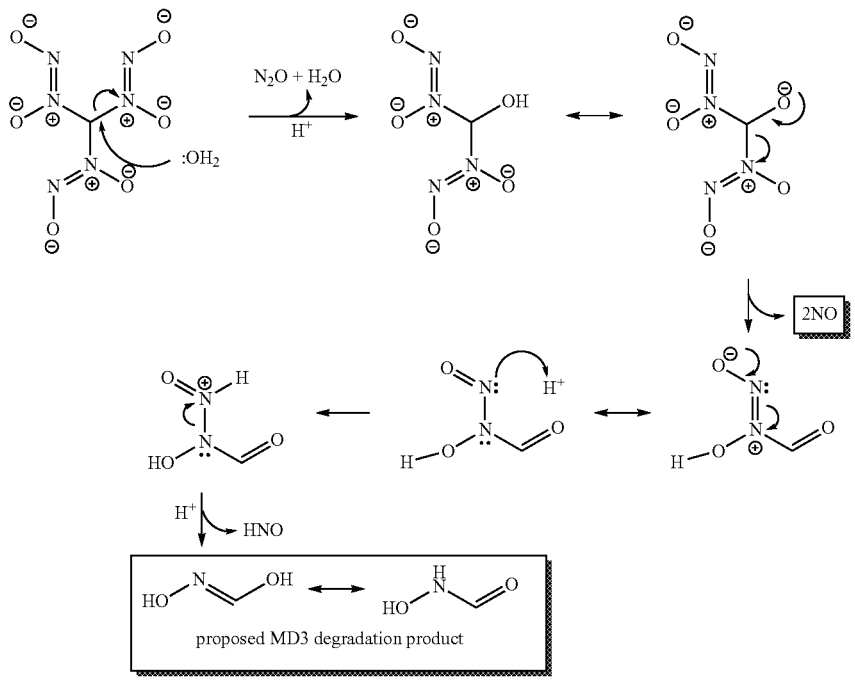

Figure 7:
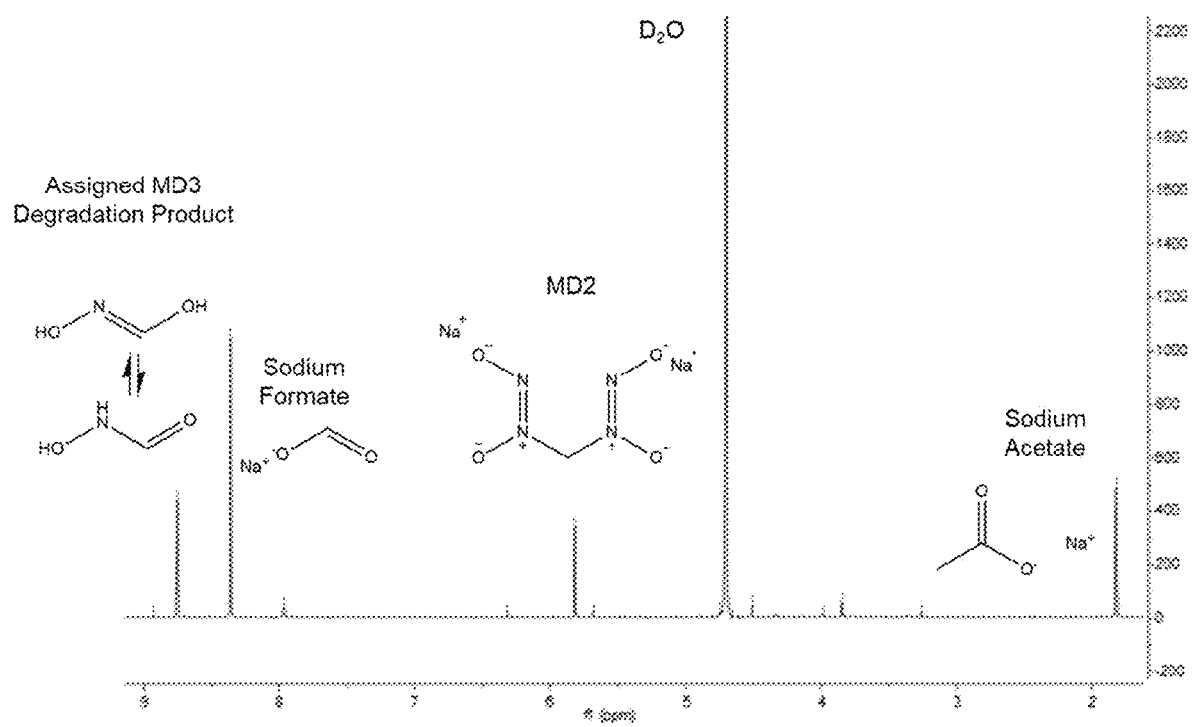
FIG. 7 is a $^1$H NMR spectrum of a the reaction products when compound of Formula III was neutralized (pH 7) at room temperature.

$^1$H and $^{13}$C NMR spectra for the degradation products are shown in FIGS. 7 and 8, respectively. Although not explicity shown, it is anticipated that $N_2O$ is not produced directly but forms when two moles of nitroxyl (HNO) are released which then dimerize and react to form $N_2O$ and $H_2O$ as shown. Nitroxyl groups are reactive nitrogen molecules which could play a role in their own right in enhancing the antimicrobial activity of the compound of Formula III.

The degradation pathway is of particular interest, because it provides clarity in how NO is being produced from a carbon bound diazeniumdiolate. Typically, carbon bound diazeniumdiolates do not generate NO. Instead, they produce HNO, which dimerizes to form nitrous oxide, $N_2O$. In this case, the initial decay of Formula III follows the expected HNO pathway, which in turn leads to the formation of an intermediate alcohol. Upon rearrangement of the alcohol intermediate, 2 moles of NO gas can be released. This matches the experimental results, which show that one mole of the compound of Formula III releases approximately 2 moles of NO. The NMR of the degraded Formula III by-product (shown in FIGS. 9 and 10) also matches the proposed structure for the fully degraded molecule.

III. Pharmaceutical Compositions

Pharmaceutical compositions comprising one or more compounds of Formulas I, II or III, along with a suitable pharmaceutically acceptable carrier or excipient, are also disclosed.

According to several embodiments, the compounds described herein can be present in aqueous solutions comprising concentrations equal to or at least about 100 μg/mL, and can be higher, e.g. about 1 mg/ml, about 5 mg/ml, about 10 mg/ml, about 20/ml, or about 40 mg/ml or higher. The amount of the second compound in the aqueous composition can be at least about 10% by weight, based on the weight of the first compound, and may be higher, e.g., at least about 20% by weight, at least about 30% by weight, or at least about 50% by weight, same basis. The compounds in an aqueous composition are selected such that compounds are mutually miscible.

In some embodiments, the compositions disclosed herein provide NO-releasing compounds discussed herein having NO storage capacities (in μmol NO/mg powder) of greater than or equal to about: 2.0, 4.0, 6.0, 8.0, or 10.0 or ranges including and/or spanning the aforementioned values. In some embodiments, within 2 h of being added to a PBS buffer solution as described in the Examples, the NO-releasing compounds, release greater than or equal to about: 25%, 50%, 75%, 85%, 90%, 95%, 100%, or ranges including and/or spanning the aforementioned values, their total wt % of bound NO.

In some embodiments, the compositions are in the form of a liquid, a dry powder, a gel, or an aerosol. The compositions may be provided in the form of a formulation loaded into a delivery device, such as an inhaler.

In some embodiments, the composition includes a concentration of less than or equal to about: 1 mg/ml, 10 mg/ml, 20 mg/ml, 50 mg/ml, 100 mg/ml, 250 mg/ml of the compounds described herein, or ranges including and/or spanning the aforementioned values.

Formulations for Pulmonary Administration

In some embodiments, the compounds are administered to the pulmonary tract (i.e., via pulmonary administration). In one specific embodiment, pulmonary administration comprises inhalation of the compounds, typically in the form of particles or droplets, such as by nasal, oral inhalation, or both. The formulations can be developed to be aerosolized via a metered dose inhaler, a dry powder inhaler, a liquid spray or a nebulizer devises. Nebulization can be accomplished by compressed air, ultrasonic energy, or vibrating mesh to form a plurality of liquid droplets or solid particles comprising the NO-releasing compounds.

In one aspect of this embodiment, particles may be formulated as an aerosol (i.e.: liquid droplets of a stable dispersion or suspension of particles which include one or more of the compounds described herein in a gaseous medium). Particles delivered by aerosol may be deposited in the airways by gravitational sedimentation, inertial impaction, and/or diffusion.

Whether administered by inhalation or nebulization, the particles or droplets can be administered in two or more separate administrations (doses).

In one embodiment, the compositions are administered via inhalation to treat bacterial infections related to cystic fibrosis. Cystic fibrosis-related bacterial infections include, but are not limited to stenotrophomonis, mybacterium *avium* intracellulaire and *M. abcessus*, burkhoderia *cepacia* and *Pseudomonas aeruginosa* (*P. aeruginosa*) infections.

Biodegradable particles can be used for the controlled-release and delivery of the compounds described herein. Aerosols for the delivery of therapeutic agents to the respiratory tract have been developed. Adjei, A. and Garren, J. Pharm Res. 7, 565-569 (1990); and Zanen, P. and Lamm, J.-W. J. Int. J. Pharm. 114, 111-115 (1995).

Porous Particles

The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. Gonda, I. "Aerosols for delivery of therapeutic and diagnostic agents to the respiratory tract," in Critical Reviews in Therapeutic Drug Carrier Systems 6:273-313, 1990. The deep lung, or alveoli, are the primary target of inhaled therapeutic aerosols for systemic drug delivery.

Accordingly, it can be important to deliver antiviral particles to the deep lung (i.e., the alveolar regions of the lung). Relatively large particles tend to get trapped in the oropharyngeal cavity, which can lead to excessive loss of the inhaled drug. Relatively smaller particles can be delivered to the deep lung, but can be phagocytosed. One way to deliver relatively large particles (sized to avoid phagocytosis), which are light enough to avoid excessive entrapment in the oropharyngeal cavity, is to use porous particles.

In one embodiment, the particles for delivering the compounds described herein to the alveolar regions of the lung are porous, "aerodynamically-light" particles, as described in U.S. Pat. No. 6,977,087. Aerodynamically light particles can be made of a biodegradable material, and typically have a tap density less than 0.4 g/$cm^3$ and a mass mean diameter between 5 μm and 30 μm. The particles may be formed of biodegradable materials such as biodegradable polymers. For example, the particles may be formed of a functionalized polyester graft copolymer consisting of a linear alpha-hydroxy-acid polyester backbone having at least one amino acid group incorporated herein and at least one poly(amino acid) side chain extending from an amino acid group in the polyester backbone. In one embodiment, aerodynamically light particles having a large mean diameter, for example greater than 5 μm, can be used for enhanced delivery of one or more of the compounds described herein to the alveolar region of the lung.

Aqueous Solutions

In several embodiments, the compounds disclosed herein are administered as aqueous solutions, for delivery, for example, topically, intranasally, intraveneously, by injection, and by nebulization. In several embodiments, the solutions comprise one or more salts and are isotonic.

Oral Drug Delivery Vehicles

In several embodiments, compositions can take the form of, for example, tablets, pills, or capsules, prepared using conventional techniques, with pharmaceutically acceptable excipients. Representative excipients include binding agents (e.g., pregelatinized maize starch, polyvinylpyrrolidone or hydroxypropyl methylcellulose), fillers (e.g., lactose, microcrystalline cellulose or calcium hydrogen phosphate), lubricants (e.g., magnesium stearate, talc or silica); disintegrants (e.g., potato starch or sodium starch glycollate), wetting agents (e.g., sodium lauryl sulphate), suspending agents, solubilizers, and mixtures thereof.

The tablets can be coated by methods known in the art. For example, a therapeutic agent can be formulated in combination with hydrochlorothiazide, and as a pH-stabilized core having an enteric or delayed release coating which protects the therapeutic agent until it reaches the target organ.

Liquid preparations for oral or topical administration can take the form of, for example, solutions, syrups or suspensions, or they can be presented as a dry product for constitution with water or another suitable vehicle before use. Such liquid preparations can be prepared by conventional techniques with pharmaceutically acceptable additives, such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations also can contain buffer salts, flavoring, coloring and sweetening agents as appropriate. Preparations for oral administration can be suitably formulated to provide controlled release of the active compound. For buccal administration the compositions can take the form of tablets or lozenges formulated in a conventional manner.

Nanoparticulate Compositions

The compounds described herein can also be administered in the form of nanoparticulate compositions. In one embodiment, the controlled release nanoparticulate formulations comprise a nanoparticulate active agent to be administered and a rate-controlling polymer which functions to prolong the release of the agent following administration. In this embodiment, the compositions can release the active agent, following administration, for a time period ranging from about 2 to about 24 hours or up to 30 days or longer. Representative controlled release formulations including a nanoparticulate form of the active agent are described, for example, in U.S. Pat. No. 8,293,277.

Nanoparticulate compositions comprise particles of the active agents described herein, having a non-crosslinked surface stabilizer adsorbed onto, or associated with, their surface. The average particle size of the nanoparticulates is typically less than about 800 nm, more typically less than about 600 nm, still more typically less than about 400 nm, less than about 300 nm, less than about 250 nm, less than about 100 nm, or less than about 50 nm. In one aspect of this embodiment, at least 50% of the particles of active agent have an average particle size of less than about 800, 600, 400, 300, 250, 100, or 50 nm, respectively, when measured by light scattering techniques.

A variety of surface stabilizers are typically used with nanoparticulate compositions to prevent the particles from clumping or aggregating. Representative surface stabilizers are selected from the group consisting of gelatin, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol, polyvinylpyrrolidone, tyloxapol, poloxamers, poloxamines, poloxamine 908, dialkylesters of sodium sulfosuccinic acid, sodium lauryl sulfate, an alkyl aryl polyether sulfonate, a mixture of sucrose stearate and sucrose distearate, p-isononylphenoxy-poly-(glycidol), SA9OHCO, decanoyl-N-methylglucamide, n-decyl-D-glucopyranoside, n-decyl-D-maltopyranoside, n-dodecyl-D-glucopyranoside, n-dodecyl-D-maltoside, heptanoyl-N-methylglucamide, n-heptyl-D-glucopyranoside, n-heptyl-D-thioglucoside, n-hexyl-D-glucopyranoside, nonanoyl-N-methylglucamide, n-nonyl-D-glucopyranoside, octanoyl-N-methylglucamide, n-octyl-D-glucopyranoside, and octyl-D-thioglucopyranoside. Lysozymes can also be used as surface stabilizers for nanoparticulate compositions.

Representative rate controlling polymers into which the nanoparticles can be formulated include chitosan, polyethylene oxide (PEO), polyvinyl acetate phthalate, gum arabic, agar, guar gum, cereal gums, dextran, casein, gelatin, pectin, carrageenan, waxes, shellac, hydrogenated vegetable oils, polyvinylpyrrolidone, hydroxypropyl cellulose (HPC), hydroxyethyl cellulose (HEC), hydroxypropyl methylcellulose (HPMC), sodium carboxymethylcellulose (CMC), poly (ethylene) oxide, alkyl cellulose, ethyl cellulose, methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly(alkylmethacrylate), poly (vinyl acetate), polymers derived from acrylic or methacrylic acid and their respective esters, and copolymers derived from acrylic or methacrylic acid and their respective esters.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Controlled Release Formulations

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Mucoadhesive Agents

Mucoadhesion is presently defined as the adhesion between two materials, at least one of which is a mucosal surface. Compounds, such as NO donors, are often delivered locally because their half-life is often below the time required for systemic distribution. The mucoadhesive agents described herein enable formulations suitable for mucoadhesive drug delivery systems (buccal, nasal, ocular, gastro, vaginal, and rectal). Mucoadhesive-containing topical and local systems have been shown to exhibit enhanced bioavailability. For example, it typically provides enhanced absorption (compared to a non-mucoadhesive formulation) and taking advantage of mucous tissues having high surface area and high blood flow.

In some embodiments, the mucoadhesive agent is a mucoadhesive polymer. In some embodiments, the mucoadhesive agent has numerous hydrophilic groups, such as hydroxyl, carboxyl, amide, and sulfate. These groups enable attachment to mucus or the cell membrane through physical and chemical interactions such as hydrogen bonding, hydrophobic, electrostatic, or conformational interactions. Hydrophilicity augments through drawing water for greater hydration and physically swell if in a gelatinous state. Aspects considered in selecting an appropriate mucoadhesive agent include the following:

1. Toxicity of the mucoadhesive agent and any potential degradation products, NO donor, and nitrosative environment, considering absorbability and mucus surface irritation,
2. Formulation compatibility with the NO donor,
3. Physiochemical mucoadhesive properties with mucus and epithelial cell surfaces (adhesion, kinetics, specificity, impact to pH and osmolality, stability, etc.), and
4. Commercial considerations (regulatory status, cost, availability, etc.).

In one embodiment, the mucoadhesive agent adheres to the mucosal surface through nonspecific, noncovalent interactions which are primarily electrostatic in nature. In another embodiment, the mucoadhesive agent adheres to the mucosal surface through hydrophilic functional groups that hydrogen bond with similar groups on biological substrates. In another embodiment, the mucoadhesive agent adheres to the mucosal surface through specific receptor sites on the cell or mucus surface. For example, lectins and thiolated polymers adhere to mucosal surfaces through specific receptor sites on the cell or mucus surfaces. As used herein, lectins are proteins or glycoprotein complexes of nonimmune origin that are able to bind sugars selectively in a noncovalent manner. It is proposed that lectins attach to carbohydrates on the mucus or epithelial cell surface. Thiolated polymers, or thiomers, have pendant thiols providing hydrophilicity, for example to polyacrylates or cellulosic polymeric backbones.

The thiol group may form stable covalent bonds with mucus glycoproteins resulting in increased residency and improved bioavailability.

Many such mucoadhesive agents are known in the art. Useful mucoadhesive polymers include but are not limited to carbopols, N-isopropylacrylamide, polyvinyl alcohol/polyvinyl pyrrolidone, dextran, hydroxyethylmethacrylate/methacrylic acid, polyvinyl alcohol, polyacrylamide, polyethylene glycol/poly lactic acid, carboxymethyl chitosan and collagen. The mucoadhesive agent may include a polycarbophil and other acrylate/methacrylate polymers, anionic polymers based on methacrylic acid esters, which form pH selectably dissolvable hydrogels that dissolve (enabling physiological conditions to interact with and further initiate the release of NO) within physiochemically specified pH ranges, generally between about pH 5.5 to about pH 7.5. Such formulations dissolving in the pH range from about 5.5 to about 6.0 is useful for targeting the duodenum. Dissolution at higher pH generally targets lower sections of the intestine. For example, a pH of dissolution of between about 6.5 to about 7.0 may be useful for targeting the colon.

In some embodiments, the mucoadhesive agent comprises a water-soluble polymer. In particular, while a water-soluble polymer may or may not form a hydrogel to some extent when hydrated, it is capable of forming a flowable aqueous solution. Mucoadhesive agents of this type include but are not limited to polyols and polycarbohydrates, hydroxylated celluloses (hydroxypropylmethyl cellulose and hydroxymethyl cellulose).

In certain embodiments, the mucoadhesive agent enhances resonance time of the nitric oxide donor at the targeted site, for example, the respiratory tract.

In other certain embodiments, the mucoadhesive agent may also possess adhesion specificity to a biofilm comprising a pathogenic species. For example, some alginate oligomers are known to interact with *Pseudomonas aeruginosa* biofilms.

Chelating Agents

In illustrative embodiments, compositions disclosed herein may include one or more chelating agents. According to one aspect, a chelating agent is included to scavenge trace metals, so as to quench their potentially deleterious effects on the NO donor compound. Exemplary chelating agents are known in the art and examples include Ethylenediaminetetraacetic acid (EDTA) or diethylenetriaminepentaacetic acid (DTPA), yet other compounds described by Baldari et al., "Current Biomedical Use of Copper Chelation Therapy," Int J Mol Sci. 2020; 21(3):1069. (2020).

Gallium

One aspect of the present invention is pharmaceutical compositions that taking advantage of the synergistic antimicrobial properties of NO and gallium. Synergy is a concept known in the art and methods for determining synergy are provided below. A minireview of antimicrobial synergy measurements was prepared by Christopher Dern of Virginia Commonwealth University and can be found at jcm.asm.org/content/jcm/52/12/4124.full.pdf which is incorporated herein by reference in its entirety.

In illustrative embodiments, disclosed is a pharmaceutical composition comprising a nitric oxide releasing compound and an aqueous solution comprising gallium. In one embodiment, the nitric oxide releasing compound is a diazeniumdiolate or a nitrosothiol. In one embodiment, the gallium is at least partially complexed in the aqueous solution with a citrate moiety. The aqueous solution may also comprise chloride ions. These chloride ions remain from dissolving, for example, gallium chloride in solution. The aqueous solution may also comprise nitrate ions. These nitrate ions remain from dissolving, for example, gallium nitrate in solution. Citrate or other chelating agents, as described herein, may be included in the formulation for stabilizing gallium against the formation of gallium hydroxide, which is not highly soluble in water and thus may precipitate. In an embodiment, a form of gallium is gallium nitrate.

Furthermore, antimicrobial compositions comprising gallium and a nitric oxide-releasing cyclodextrin and their use in decreasing microbial load are provided herein. The inventors of the present application have surprisingly discovered that not only are compositions comprising gallium and nitric oxide donors effective against plankton bacteria and biofilms, but these compositions also exhibit synergistic effects against the same.

Provided herein are compositions comprising gallium and one or more of the compounds described herein, and methods of treating various pathophysiologies using such compositions that leverage the synergistic effects of gallium combined with the NO donating compounds, which in turn leverage enhanced NO-release characteristics and beneficial physical properties, harnessing the abundant potential of NO-releasing pharmacological compounds and compositions. In several embodiments, provided herein are compositions that are highly efficacious as antimicrobials. In several embodiments, provided herein are compositions with beneficial antimicrobial properties. In several embodiments, the polymers and/or scaffolds disclosed herein have advantageous activity as mucoadhesive agents or chelating agents as described herein.

The gallium may be gallium (III), gallium nitrate (Ga(NO$_3$)$_3$), gallium chloride, a pharmaceutically acceptable salt, pharmaceutically acceptable complex, or combination thereof.

The composition may comprise about 0.001 mg to 100 mg of gallium. For example, the composition may comprise about 0.001, 0.002, 0.003, 0.004, 0.005, 0.006, 0.007, 0.008, 0.009, or 0.01 mg of gallium. The composition may comprise about 0.01, 0.02, 0.03, 0.04, 0.05, 0.06, 0.07, 0.08, 0.09, or 0.1 mg of gallium. The composition may comprise about 0.1, 0.2, 0.3, 0.4, 0.5, 0.6, 0.7, 0.8, 0.9, or 1.0 mg of gallium. The composition may comprise about 1, 2, 3, 4, 5, 6, 7, 8, 9, or 10 mg of gallium. The composition may comprise about 10, 20, 30, 40, 50, 60, 70, 80, 90, or 100 mg of gallium.

The composition may comprise gallium dosed at about 0.001 mg to 100 mg of gallium per kg of the patient. The composition may comprise gallium dosed at about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or 100 mg of gallium per kg of the patient.

The gallium may be in the form of a pharmaceutically acceptable salt or pharmaceutically acceptable complex. In one embodiment, the pharmaceutically acceptable salt is an anion selected from the group consisting of nitrate, citrate, chloride, acetate, isocitrate, tartrate, and mixtures thereof. In another embodiment, the anion is the compound described herein, i.e., M$^+$ is gallium. Where the anion is not the compound described herein, gallium is present with a different anion, and the compound is present with a different cation, but some degree of metathesis can occur, leading to the formation of gallium salts of the compounds described herein at equilibrium.

The pharmaceutically acceptable complex agent, which is also described herein as a chelating agent, may be mannitol, maltolate or a derivative, protoporphyrin IX or a derivative, lactoferrin, transferrin, ferritin, bacterial siderophores belonging to the catecholate, hydroxamate, and hydroxycarboxylate groups, bacterial hemophores, and any chelators of iron.

Siderophores

Siderophores have been used in medicine for iron and aluminum overload therapy and antibiotics for improved targeting. For example, an iron-chelating microbial siderophore can be conjugated to an antibiotic or antimicrobial agent to enhance uptake and antibacterial potency. Several embodiments disclosed herein pertain to a pharmaceutical formulation comprising at least one nitric oxide releasing moiety, optionally in combination with at least one siderophore. In some embodiments, the at least one siderophore is functionalized by a NO-donating group, and the composition further includes at least one pharmaceutically acceptable excipient.

Implantation

In several embodiments, the disclosed compositions also can be formulated as a preparation for implantation. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt). The compositions also can be formulated in rectal compositions (e.g., suppositories or retention enemas containing conventional suppository bases, such as cocoa butter or other glycerides), creams or lotions, or transdermal patches.

Composition Properties

In several embodiments, the combination of all the various components of the pharmaceutical composition, including the molecular weight, concentrations, or other chemical features of the compounds, and other components in the compositions, contribute to the tunability of the properties of the compositions disclosed herein. In several embodiments, by changing one or more of these features, one or more properties of the compositions can be tuned according to the preferred properties described herein. In several embodiments, the NO release rate, antimicrobial effect, water solubility, degradation rate, viscosity, gel firmness (where the formulation forms a gel), viscoelasticity, modulus, etc. are tunable.

In those embodiments where polymers are present in the formulations along with the small molecule NO-releasing compounds described herein, the properties of compositions can be tuned by adjusting the molecular weight of certain polymers used in the formulation. In several embodiments, the weight-average molecular weight ($M_w$) in kDa of polymers disclosed herein are greater than or equal to about: 2.5, 5.0, 7.0, 10, 15, 30, 50, 100, 200, 500, 750, 1,000, 2,000, 10,000, or ranges including and/or spanning the aforementioned values. In several embodiments, the number-average molecular weight ($M_n$) in kDa of polymers disclosed herein are greater than or equal to about: 2.5, 5.0, 7.0, 10, 15, 30, 50, 90, 100, 200, 500, 700, 1,000, 2,000, 10,000, or ranges including and/or spanning the aforementioned values. In several embodiments, the polymers disclosed herein may have n repeat units. In several embodiments, n equal to or at least about: 10, 25, 50, 100, 250, 500, 1000, 2500, 5000, 10000, or ranges including and/or spanning the aforementioned values. In several embodiments, size exclusion chromatography (SEC) can be used to measure the molecular weight of the scaffold structures disclosed herein. In several embodiments, multi-angle light scattering (SEC-MALS) detectors can be used. In several embodiments, the scaffold structures can be characterized using their polydispersity index. The polydispersity index (PDI) is a measure of the distribution of molecular mass in a given polymer sample. PDI can be calculated by dividing the weight average molecular weight and the number average molecular weight. In several embodiments, the scaffold structures have a PDI of greater than or equal to about: 1.05, 1.1, 1.2, 1.3, 1.5, 1.7, 1.8, 1.9, 2.0, or ranges including and/or spanning the aforementioned values.

Representative polymers include those disclosed in each of U.S. Patent Application No. 62/441,742, U.S. Patent Application No. 62/483,505 International Application No. PCT/IB2018/050051, U.S. Patent Application No. 62/447,564, International Application No. PCT/IB2018/052144, U.S. patent application Ser. No. 14/421,525, U.S. Patent Application No. 62/639,119, and U.S. Patent Application No. 62/737,603 are used. Each of these applications and publications is incorporated by reference in its entirety for all purposes.

In several embodiments, the compositions (including all the components) may be water soluble and/or mutually miscible. In several embodiments, the compositions are soluble in water (at about 20° C.) at a concentration of greater than or equal to about: 1 mg/ml, 10 mg/ml, 20 mg/ml, 50 mg/ml, 100 mg/ml, 200 mg/ml, 300 mg/ml, 400 mg/ml, 500 mg/ml, or ranges including and/or spanning the aforementioned values.

According to several embodiments, the NO donor can be formulated within a pharmaceutical formulation at a concentration equal to or at least about: 100 μg/mL, and can be higher, e.g. about 1 mg/ml, about 5 mg/ml, about 10 mg/ml, about 20 mg/ml, 25 mg/ml, 50 mg/ml, 75 mg/ml, 100 mg/ml or about 200 mg/ml or higher. In illustrative embodiments, a polymeric species can be formulated within a pharmaceutical formulation at a concentration equal to or at least about: 100 μg/mL, and can be higher, e.g. about 1 mg/ml, about 5 mg/ml, about 10 mg/ml, about 20 mg/ml, 25 mg/ml, 50 mg/ml, 75 mg/ml, 100 mg/ml or about 200 mg/ml or higher. The amount of the polymer in the aqueous composition can be at least about 10% by weight, based on the weight of the NO donor, and may be higher, e.g., at least about 20% by weight, at least about 30% by weight, or at least about 50% by weight, same basis. Any combinations of NO donors and polymers in an aqueous composition are selected to be mutually miscible. As noted above, the NO donor with antimicrobial activity and the polymer are considered mutually miscible if at least about 90% of the polymeric components remain mutually soluble 24 hours after mixing and maintaining at room temperature in water at a concentration of each polymer of 1 mg/ml, upon visible examination. Surprisingly, such mutual miscibility of the water-soluble polymers with the NO donors can be achieved, despite an expectation of phase separation at the 1 mg/ml concentrations and molecular weights described herein. The aqueous compositions described herein can be prepared by intermixing the individual formulation components with water, e.g., at room temperature with stirring.

In several embodiments, the composition disclosed herein have properties characteristic of a viscous fluid and/or of a gel. In several embodiments, a composition has a gelling point at room temperature (in water or PBS) at a concentration (in w/w %) of less than or equal to about: 0.5%, 1%, 2.5%, 5%, 10%, or ranges including and/or spanning the aforementioned values. In several embodiments, the composition may have a gelling point in water. In several embodiments, the composition gels in water (at about 20° C.) at a concentration of greater than or equal to about: 0.5 mg/ml, 1 mg/ml, 10 mg/ml, 20 mg/ml, 50 mg/ml, 100 mg/ml, 250 mg/ml, or ranges including and/or spanning the aforementioned values. In several embodiments, at a concentration of 5% w/w solution, the polymers have a viscosity (in cPa·s at 20° C.) of equal to or at least about: 10, 50, 100, 1,000, 2,000, 5,000, 10,000, or ranges including and/or spanning the aforementioned values. In several embodiments, the polymers have an intrinsic viscosity of equal to or greater than about: 0.5 m$^3$/kg, 1.0 m$^3$/kg, 2.0 m$^3$/kg, 4.0 m$^3$/kg, 8.0 m$^3$/kg, or ranges including and/or spanning the aforementioned values.

In several embodiments, at a concentration of 5% w/w solution, the compositions have a firmness of equal to or at least about: 1.0 mN, 2.5 mN, 5 mN, 10 mN, 15 mN, 20 mN, 30 mN, 50 mN, or ranges including and/or spanning the aforementioned values. In several embodiments, at a concentration of 5% w/w solution, the formulations have a work of adhesion (in mN*mm) of equal to or at least about: 1.0, 2.5, 5, 10, 15, 20, 30, 50, 100, or ranges including and/or spanning the aforementioned values. In several embodiments, at a concentration of 5% w/w solution, the compositions have a storage modulus (G') in Pa of equal to or at least about: 250, 500, 1,000, 2,000, 4,000, 5,000, 10,000, or ranges including and/or spanning the aforementioned values. In several embodiments, at a concentration of 5% w/w solution, the compositions have an elastic modulus (G") in Pa of equal to or at least about: 25, 50, 100, 200, 400, 500, 1,000, 2,000, 5,000, 10,000, or ranges including and/or spanning the aforementioned values. In several embodiments, the aqueous composition is characterized by a barrier activity, as measured by a decrease in the diffusion rate of an anionic dye of more than 2 logs at a total scaffold concentration of 40 mg/ml or less.

In several embodiments, the formulation is a gel and the gel are stable at a variety of temperatures 20° C. (e.g., 40° C., 45° C., 55° C., 60° C., 80° C., etc.) and are stable for prolonged storage periods (e.g., 10 hours, 20 hours, 22 hours, 25 hours, 30 hours, etc., days such as 1 day, 3 days, 5 days, 6 days, 7 days, 15 days, 30 days, 45 days, etc., weeks such as 1 week, 2 weeks, 3 weeks, 4 weeks, 6 weeks, 8 weeks, etc., months such as 1 month, 2 months, 3 months, 4 months, 5 months, 6 months, etc., or even years (1 year or greater)).

In several embodiments, the viscosity of the composition increases with increasing temperature, or decreases with decreasing temperature. For example, if the composition is above the gelling temperature, then the composition has a relatively high viscosity, such as in the form of a gel, and if cooled to below the gelling temperature, then the composition decreases in viscosity, such as in the form of a liquid. In several embodiments, as such, the polymers as disclosed herein may be reversible polymers (e.g., thermoreversible polymers), where the transition from liquid to gel may be reversed upon exposure to appropriate conditions. For instance, as described above, compositions of the present disclosure include thermoreversible polymers, where the viscosity of the composition may be changed depending on the temperature of the composition. In several embodiments, the tunability of the viscosity enables a tailored composition profile upon delivery (e.g., more liquid at a delivery temperature and more viscous at, for example, body temperature).

In several embodiments, the compositions are characterized by a degree of swelling when exposed to water. In some embodiments, the swelling degree % of the composition disclosed herein is equal to or at least about: 100, 250, 500, 1,000, 2,000, 5,000, or ranges including and/or spanning the aforementioned values. In other words, the composition may swell or otherwise expand by 2×, 4×, 5×, 10×, 20×, 50×, 100×, or more.

In certain embodiments, the compositions disclosed herein have a gelling temperature similar to the normal body temperature of a subject, such as similar to human body temperature, or 37° C. By gelling temperature is meant the point on intersection between the plot for the elastic modulus and the plot for the viscous modulus. In some cases, if the composition is below the gelling temperature, then the composition has a relatively low viscosity, such as in the form of a liquid. In some instances, if the composition is above the gelling temperature, then the composition increases in viscosity (e.g., polymerizes), such that the composition is in the form of a gel. Compositions that transition from a liquid to a gel may facilitate administration of the composition to the subject, for example by facilitating injection of a low viscosity (e.g., liquid) composition at a temperature below the gelling temperature. After injection of the composition to the target treatment site, the temperature of the composition may increase due to absorption of heat from the surrounding body tissue, such that the composition increases in viscosity (e.g., transitions from a liquid to a gel, or polymerizes), thus providing structural and/or geometric support to the body tissue at the target treatment site. In some instances, gelling of the composition at the target treatment site may also facilitate retention of the composition at the treatment site by reducing the diffusion and/or migration of the composition away from the treatment site. In certain embodiments, the composition has a gelling temperature of 30° C. to 40° C., such as from 32° C. to 40° C., including from 35° C. to 40° C. In certain instances, the composition has a gelling temperature of 37° C.

Combination Therapy

The compounds described herein can be combined with conventional antimicrobial compounds. For example, in addition to administering one or more of the compounds described herein, a patient can also be administered a conventional antimicrobial agent.

Examples of conventional antibiotic agents include, but are not limited to, amikacin, tobramycin, gentamicin, piperacillin, mezlocillin, ticarcillin, imipenem, ciprofloxacin, ceftazidime, aztreonam, ticarcillin-clavulanate, dicloxacillin, amoxicillin, trimethoprim-sulfamethoxazole, cephalexin, piperacillin-tazobactam, linezolid, daptomycin, vancomycin, metronidazole, clindamycin, colistin, tetracycline, levofloxacin, amoxicillin and clavulanic acid (Augmentin®), cloxacillin, dicloxacillin, cefdinir, cefprozil, cefaclor, cefuroxime, erythromycin/sulfisoxazole, erythromycin, clarithromycin, azithromycin, doxycycline, minocycline, tigecycline, imipenem, meropenem, colistimethate/Colistin®, methicillin, oxacillin, nafcillin, carbenicillin, azlocillin, piperacillin and tazobactam (Zosyn®), cefepime, ethambutol, rifampin, and meropenem.

These antibiotics can also be combined with compounds that bind to or adsorb bacterial toxins, which can be particularly useful where bacterial toxins result in tissue damage. By way of example, *Pseudomonas aeruginosa* produces a variety of toxins that lead to cell lysis and tissue damage in the host. Type II toxins include Exotoxin U (Exo U), which degrades the plasma membrane of eukaryotic cells, leading to lysis, phospholipase C (PLC), which damages cellular phospholipids causing tissue damage and stimulates inflammation, alkaline protease, which leads to tissue damage, cytotoxin, which damages cell membranes of leukocytes and causes microvascular damage, elastase, which destroys elastin, a protein that is a component of lung tissue, and pyocyanin, a green to blue water-soluble pigment that catalyzes the formation of tissue-damaging toxic oxygen radicals, impairs ciliary function, and stimulates inflammation. Examples of compounds that bind these toxins include polyphenols and polyanionic polymers.

Antifungals can also be co-administered, where the microbe is a fungus. Representative antifungal agents which can be used include fluconazole, posaconazole, viroconazole, itraconazole, echinocandin, amphotericin, and flucytosine. The choice of an appropriate antifungal agent can be made by a treating physician, and the following is a summary of fungal pulmonary infections and their treatments.

Histoplasmosis is caused by the fungus *Histoplasma capsulatum*, and conventional treatment includes Itraconazole mild and chronic pulmonary disease, and Amphotericin B (AmB) with itraconazole for moderate-to-severe histoplasmosis.

Blastomycosis is caused by *Blastomyces dermatitidis*, and conventional treatment includes itraconazole for mild-to-moderate disease and liposomal AmB (L-AmB) followed by itraconazole for life-threatening pulmonary infections.

Sporotrichosis is caused by *Sporothrix schenckii*, and conventional treatment for mild-to-moderate pulmonary disease requires itraconazole, whereas AmB followed by itraconazole is recommended for severe disease.

Coccidioidomycosis is caused by *Coccidioides immitis* and *Coccidioides posadasii*. Immunocompetent infected hosts may not require treatment, but immunocompromised patients are treated with fluconazole or itraconazole, and, in serious cases with AmB, followed by an azole.

Opportunistic fungal infections primarily cause infections in patients who tend to be immunocompromised through a congenital or acquired disease process. Representative opportunistic infections are discussed below.

Aspergillosis is caused by Aspergilli, and the associated disorders include invasive pulmonary aspergillosis (IPA), chronic necrotizing aspergillosis, Aspergilloma, and allergic bronchopulmonary aspergillosis. Conventional treatments for IPA include voriconazole, lipid-based AmB formulations, echinocandins, and posaconazole.

Cryptococcosis is an opportunistic infection seen in immunocompromised individuals, including HIV or AIDS patients and organ-transplant recipients. Conventional treatments include AmB, with or without flucytosine, followed by oral fluconazole. For immunosuppressed or immunocompetent patients exhibiting mild-to-moderate symptoms, fluconazole therapy is recommended.

Candidiasis can be caused when lung parenchyma become colonized with *Candida* species. Many critically ill patients are empirically treated with broad-spectrum antibiotics. Further clinical deterioration and lack of improvement in these cases suggest the initiation of empiric antifungal therapy. Triazole antifungals and echinocandins exhibit excellent lung penetration, so, in addition to AmB formulations, can be used to treat pulmonary candidiasis.

Mucormycosis often occurs in patients with diabetes mellitus, organ or hematopoietic stem cell transplant, neutropenia, or malignancy. Pulmonary mucormycosis is primarily observed in patients with a predisposing condition of neutropenia or corticosteroid use. Due to fungal adherence to and damage of endothelial cells, fungal angioinvasion, vessel thrombosis, and successive tissue necrosis, conventional antifungal agents have a difficult time penetrating through the lung tissue. For this reason, conventional treatment includes débridement of necrotic tissue and antifungal therapy, using AmB formulations, posaconazole, and iron chelation therapy.

*Pneumocystis jirovecii* Pneumonia (PCP) occurs in patients with HIV/AIDS, hematologic and solid malignancies, organ transplant, and diseases requiring immunosuppressive agents. PCP is extremely resistant to common antifungal therapy, including AmB formulations and triazole antifungals, but can be treated with Trimethoprim/sulfamethoxazole. Second-line agents primaquine plus clindamycin, atovaquone, IV pentamidine, or dapsone.

The antifungal agents identified herein can be co-administered with the therapeutic approaches described herein.

When the patient has a viral pulmonary infection, conventional antiviral agents used for such viruses can be administered. The selection of antivirals typically depends on the viral infection being treated. Influenza virus is typically treated with oseltamivir (Tamiflu), zanamivir (Relenza), or peramivir (Rapivab), and RSV with ribavirin (Virazol). Coronavirus is also being treated with Tamiflu, ribavirin, certain anti-HIV compounds, and certain interferons, including Betaferon, Alferon, Multiferon, and Wellferon.

Combination Therapy for Particular Use in Treating Covid-19 Infections

The compounds described herein can be combined with additional compounds useful for treating the disease states also treated by the release of NO. In particular, the compounds discussed below can be used in combination therapy to treat Covid-19 infections, or other respiratory infections with similar pathology.

Various compounds that can be combined with the compounds described herein are discussed below.

In one aspect of this embodiment, the at least one other active agent is selected from the group consisting of fusion inhibitors, entry inhibitors, protease inhibitors, polymerase inhibitors, antiviral nucleosides, such as remdesivir, GS-441524, N4-hydroxycytidine, and other compounds disclosed in U.S. Pat. No. 9,809,616, and their prodrugs, viral entry inhibitors, viral maturation inhibitors, JAK inhibitors, angiotensin-converting enzyme 2 (ACE2) inhibitors, SARS-COV-specific human monoclonal antibodies, including CR3022, and agents of distinct or unknown mechanism.

Umifenovir (also known as Arbidol) is a representative fusion inhibitor.

Representative entry inhibitors include Camostat, luteolin, MDL28170, SSAA09E2, SSAA09E1 (which acts as a cathepsin L inhibitor), SSAA09E3, and tetra-O-galloyl-D-glucose (TGG). The chemical formulae of certain of these compounds are provided below:

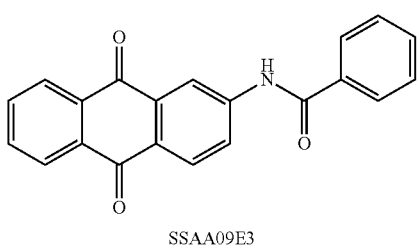

SSAA09E3

-continued
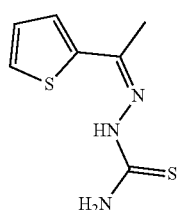
SSAA09E1
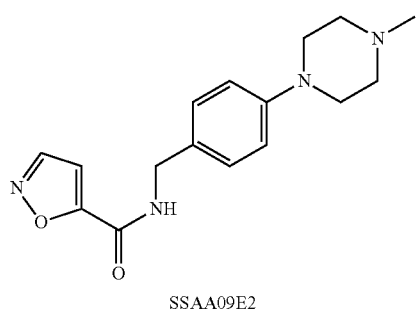
SSAA09E2
Other entry inhibitors include the following:
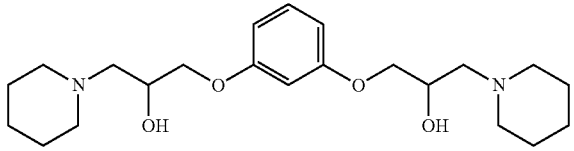
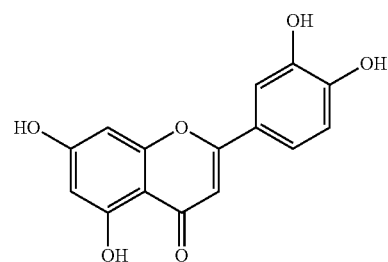
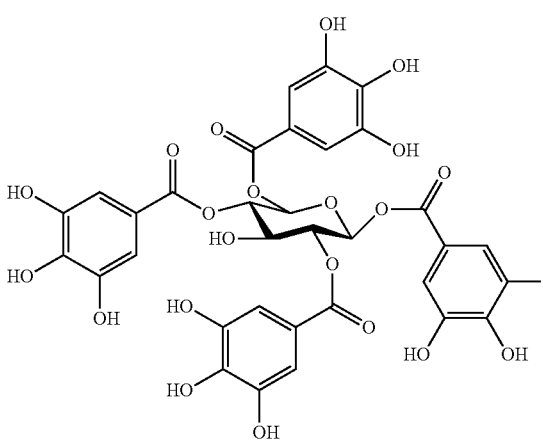
-continued
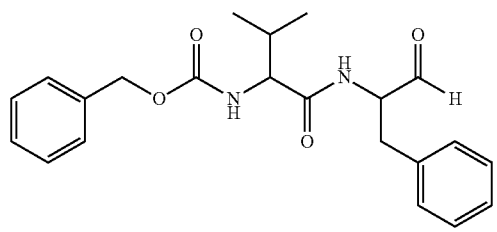
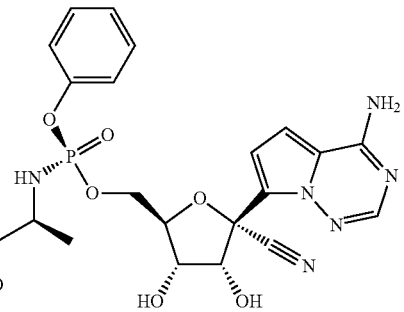
Remdesivir
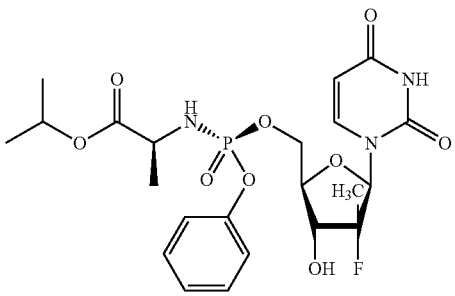
Sofosbuvir
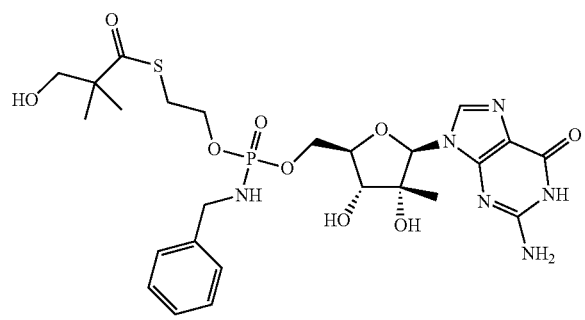
IDX-184

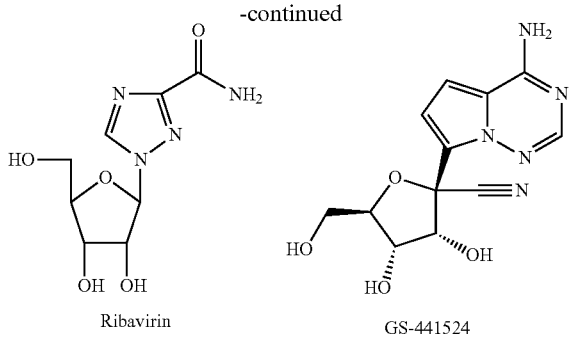

Ribavirin

GS-441524

Additionally, one can administer compounds which inhibit the cytokine storm, such as dexamethasone, anticoagulants and/or platelet aggregation inhibitors that address blood clots, or compounds which chelate iron ions released from hemoglobin by viruses such as COVID-19.

Representative ACE-2 inhibitors include sulfhydryl-containing agents, such as alacepril, captopril (capoten), and zefnopril, dicarboxylate-containing agents, such as enalapril (vasotec), ramipril (altace), quinapril (accupril), perindopril (coversyl), lisinopril (listril), benazepril (lotensin), imidapril (tanatril), trandolapril (mavik), and cilazapril (inhibace), and phosphonate-containing agents, such as fosinopril (fositen/monopril).

For example, when used to treat or prevent infection, the active compound or its prodrug or pharmaceutically acceptable salt can be administered in combination or alternation with another antiviral agent including, but not limited to, those of the formulae above. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

A number of agents for combination with the compounds described herein are disclosed in Ghosh et al., "Drug Development and Medicinal Chemistry Efforts Toward SARS-Coronavirus and Covid-19 Therapeutics," ChemMedChem 10.1002/cmdc.202000223.

Nonlimiting examples of antiviral agents that can be used in combination with the compounds disclosed herein include those listed below.

Compounds for Inhibiting the Cytokine Storm

Throughout its activation, the inflammatory response must be regulated to prevent a damaging systemic inflammation, also known as a "cytokine storm." A number of cytokines with anti-inflammatory properties are responsible for this, such as IL-10 and transforming growth factor β (TGF-β). Each cytokine acts on a different part of the inflammatory response. For example, products of the Th2 immune response suppress the Th1 immune response and vice versa.

By resolving inflammation, one can minimize collateral damage to surrounding cells, with little or no long-term damage to the patient. Accordingly, in addition to using the compounds described herein to inhibit the viral infection, one or more compounds which inhibit the cytokine storm can be co-administered.

Compounds which inhibit the cytokine storm include compounds that target fundamental immune pathways, such as the chemokine network and the cholinergic anti-inflammatory pathway.

JAK inhibitors, such as JAK 1 and JAK 2 inhibitors, can inhibit the cytokine storm, and in some cases, are also antiviral. Representative JAK inhibitors include those disclosed in U.S. Pat. No. 10,022,378, such as Jakafi, Tofacitinib, and Baricitinib, as well as LY3009104/INCB28050, Pacritinib/SB1518, VX-509, GLPG0634, INC424, R-348, CYT387, TG 10138, AEG 3482, and pharmaceutically acceptable salts and prodrugs thereof.

HMGB1 antibodies and COX-2 inhibitors can be used, which downregulate the cytokine storm. Examples of such compounds include Actemra (Roche). Celebrex (celecoxib), a COX-2 inhibitor, can be used. IL-8 (CXCL8) inhibitors can also be used.

Chemokine receptor CCR2 antagonists, such as PF-04178903 can reduce pulmonary immune pathology.

Selective α7Ach receptor agonists, such as GTS-21 (DMXB-A) and CNI-1495, can be used. These compounds reduce TNF-α. The late mediator of sepsis, HMGB1, downregulates IFN-γ pathways, and prevents the LPS-induced suppression of IL-10 and STAT 3 mechanisms.

Compounds for Treating or Preventing Blood Clots

Viruses that cause respiratory infections, including Coronaviruses such as Covid-19, can be associated with pulmonary blood clots, and blood clots that can also do damage to the heart.

The compounds described herein can be co-administered with compounds that inhibit blood clot formation, such as blood thinners, or compounds that break up existing blood clots, such as tissue plasminogen activator (TPA), Integrilin (eptifibatide), abciximab (ReoPro) or tirofiban (Aggrastat).

Blood thinners prevent blood clots from forming, and keep existing blood clots from getting larger. There are two main types of blood thinners. Anticoagulants, such as heparin or warfarin (also called Coumadin), slow down biological processes for producing clots, and antiplatelet aggregation drugs, such as Plavix, aspirin, prevent blood cells called platelets from clumping together to form a clot.

By way of example, Integrilin® is typically administered at a dosage of 180 mcg/kg intravenous bolus administered as soon as possible following diagnosis, with 2 mcg/kg/min continuous infusion (following the initial bolus) for up to 96 hours of therapy.

Representative platelet aggregation inhibitors include glycoprotein IIB/IIIA inhibitors, phosphodiesterase inhibitors, adenosine reuptake inhibitors, and adenosine diphosphate (ADP) receptor inhibitors. These can optionally be administered in combination with an anticoagulant.

Representative anti-coagulants include coumarins (vitamin K antagonists), heparin and derivatives thereof, including unfractionated heparin (UFH), low molecular weight heparin (LMWH), and ultra-low-molecular weight heparin (ULMWH), synthetic pentasaccharide inhibitors of factor Xa, including Fondaparinux, Idraparinux, and Idrabiotaparinux, directly acting oral anticoagulants (DAOCs), such as dabigatran, rivaroxaban, apixaban, edoxaban and betrixaban, and antithrombin protein therapeutics/thrombin inhibitors, such as bivalent drugs hirudin, lepirudin, and bivalirudin and monovalent argatroban.

Representative platelet aggregation inhibitors include pravastatin, Plavix (clopidogrel bisulfate), Pletal (cilostazol), Effient (prasugrel), Aggrenox (aspirin and dipyridamole), Brilinta (ticagrelor), caplacizumab, Kengreal (cangrelor), Persantine (dipyridamole), Ticlid (ticlopidine), Yosprala (aspirin and omeprazole).

Additional Compounds that can be Used

Additional compounds and compound classes that can be used in combination therapy include the following: Antibodies, including monoclonal antibodies (mAb), Arbidol (umifenovir), Actemra (tocilizumab), APN01 (Aperion Biologics), ARMS-1 (which includes Cetylpyridinium chloride (CPC)), ASC09 (Ascletis Pharma), AT-001 (Applied Therapeutics Inc.) and other aldose reductase inhibitors (ARI), ATYR1923 (aTyr Pharma, Inc.), Aviptadil (Relief Therapeutics), Azvudine, Bemcentinib, BLD-2660 (Blade Therapeutics), Bevacizumab, Brensocatib, Calquence (acalabrutinib), Camostat mesylate (a TMPRSS2 inhibitor), Camrelizumab, CAP-1002 (Capricor Therapeutics), CD24Fcm, Clevudine, (Oncolmmune), CM4620-IE (CalciMedica Inc., CRAC channel inhibitor), Colchicine, convalescent plasma, CYNK-001 (Sorrento Therapeutics), DAS181 (Ansun Pharma), Desferal, Dipyridamole (Persantine), Dociparstat sodium (DSTAT), Duvelisib, Eculizumab, EIDD-2801 (Ridgeback Biotherapeutics), Emapalumab, Fadraciclib (CYC065) and seliciclib (roscovitine) (Cyclin-dependent kinase (CDK) inhibitors), Farxiga (dapagliflozin), Favilavir/Favipiravir/T-705/Avigan, Galidesivir, Ganovo (danoprevir), Gilenya (fingolimod) (sphingosine 1-phosphate receptor modulator), Gimsilumab, IFX-1, Ilaris (canakinumab), intravenous immunoglobulin, Ivermectin (importin α/β inhibitor), Kaletra/Aluvia (lopinavir/ritonavir), Kevzara (sarilumab), Kineret (anakinra), LAU-7b (fenretinide), Lenzilumab, Leronlimab (PRO 140), LY3127804 (an anti-Ang2 antibody), Leukine (sargramostim, a granulocyte macrophage colony stimulating factor), Losartan, Valsartan, and Telmisartan (Angiotensin II receptor antagonists), Meplazumab, Metablok (LSALT peptide, a DPEP1 inhibitor), Methylprednisolone and other corticosteroids, MN-166 (ibudilast, Macrophage migration inhibitory factor (MIF) inhibitor), MRx-4DP0004 (a strain of *Bifidobacterium breve*, 4D Pharma), Nafamostat (a serine protease inhibitor), Neuraminidase inhibitors like Tamiflu (oseltamivir), Nitazoxanide (nucleocapsid (N) protein inhibitor), Nivolumab, OT-101 (Mateon), Novaferon (man-made Interferon), Opaganib (yeliva) (Sphingo sine kinase-2 inhibitor), Otilimab, PD-1 blocking antibody, peginterferons, such as peginterferon lambda, Pepcid (famotidine), Piclidenoson (A3 adenosine receptor agonist), Prezcobix (darunavir), PUL-042 (Pulmotect, Inc., toll-like receptor (TLR) binder), Rebif (interferon beta-la), RHB-107 (upamostat) (serine protease inhibitor, RedHill Biopharma Ltd.), Selinexor (selective inhibitor of nuclear export (SINE)), SNG001 (Synairgen, inhaled interferon beta-la), Solnatide, stem cells, including mesenchymal stem cells, MultiStem (Athersys), and PLX (Pluristem Therapeutics), Sylvant (siltuximab), Thymosin, TJM2 (TJ003234), Tradipitant (neurokinin-1 receptor antagonist), Truvada (emtricitabine and tenofovir), Ultomiris (ravulizumab-cwvz), Vazegepant (CGRP receptor antagonist or blocker), and Xofluza (baloxavir marboxil).

Repurposed Antiviral Agents

A number of pharmaceutical agents, including agents active against other viruses, have been evaluated against Covid-19, and found to have activity. Any of these compounds can be combined with the compounds described herein. Representative compounds include lopinavir, ritonavir, niclosamide, promazine, PNU, UC2, cinanserin (SQ 10,643), Calmidazolium (C3930), tannic acid, 3-isotheaflavin-3-gallate, theaflavin-3,3'-digallate, glycyrrhizin, S-nitroso-N-acetylpenicillamine, nelfinavir, niclosamide, chloroquine, hydroxychloroquine, 5-benzyloxygramine, ribavirin, Interferons, such as Interferon (IFN)-α, IFN-β, and pegylated versions thereof, as well as combinations of these compounds with ribavirin, chlorpromazine hydrochloride, triflupromazine hydrochloride, gemcitabine, imatinib mesylate, dasatinib, and imatinib.

IV. Types of Microbes that can be Treated

The following are non-limiting examples of microbes, including bacteria, viruses, and fungi, that can be treated using the compounds described herein.

Types of Bacterial Infections that can be Treated

In one embodiment, the compounds described herein are used to treat bacterial infections in the respiratory tract. Examples of pathogens that can be treated include *Haemophilus influenzae, Pseudomonas aeruginosa, Staphylococcus aureus, Staphylococcus warneri, Staphylococcus lugdunensis, Staphylococcus epidermidis, Streptococcus milleri/anginous, Streptococcus pyogenes*, non-tuberculosis mycobacterium, *Mycobacterium tuberculosis, Burkholderia* spp., *Achromobacter xylosoxidans, Pandoraeasputorum, Stenotrophomonas maltophilia, Alcaligenes xylosoxidans, Haemophilus pittmaniae, Serratia marcescens, Candida albicans*, drug resistant *Candida albicans, Candida glabrata, Candida krusei, Candida guilliermondii, Candida auris, Candida tropicalis, Aspergillus niger, Aspergillus terreus, Aspergillus fumigatus, Aspergillus flavus, Morganella morganii, Inquilinus limosus, Ralstonia mannitolilytica, Pandoraea apista, Pandoraea pnomenusa, Pandoraea sputorum, Bdellovibrio bacteriovorus, Bordetella bronchiseptica, Vampirovibrio chlorellavorus, Actinobacter baumanni, Cupriadidus metallidurans, Cupriavidus pauculus, Cupriavidus respiraculi, Delftia acidivordans, Exophilia dermatitidis, Herbaspirillum frisingense, Herbaspirillum seropedicae, Klebsiella pneumoniae, Pandoraea norimbergensis, Pandoraea pulmonicola, Pseudomonasmendocina, Pseudomonas pseudoalcaligenes, Pseudomonas putida, Pseudomonas stutzeri, Ralstonia insidiosa, Ralstonia pickettii, Neisseriagonorrhoeae*, NDM-1 positive *E. coli, Enterobacter cloaca*, Vancomycin-resistant *E. faecium*, Vancomycin-resistant *E. faecalis, E. faecium, E. faecalis*, Clindamycin-resistant *S. agalactiae, S. agalactiae, Bacteroides fragilis, Clostridium difficile, Streptococcus pneumonia, Moraxella catarrhalis, Haemophilus haemolyticus, Haemophilus parainfluenzae, Chlamydophilia pneumoniae, Mycoplasma pneumoniae, Atopobium, Sphingomonas, Saccharibacteria, Leptotrichia, Capnocytophaga, Oribacterium, Aquabacterium, Lachnoanaerobaculum, Campylobacter, Acinetobacter, Agrobacterium; Bordetella; Brevundimonas; Chryseobacterium; Delftia; Enterobacter; Klebsiella; Pandoraea; Pseudomonas; Ralstonia*, and *Prevotella*.

Representative non-tuberculosis *mycobacterium* include *Mycobacterium abscessus, Mycobacterium avium, Mycobacteriumintracellulare, Mycobacterium fortuitum, Mycobacterium gordonae, Mycobacterium kansasii, Mycobacterium avium* complex, *Mycobacteriummarinum, Mycobacterium terrae* and *Mycobacterium cheloni*.

Representative *Burkholderia* spp. Include *Burkholderia cepacia, Burkholderia cepacia* complex, *Burkholderia multivorans, Burkholderia cenocepacia, Burkholderia stabilis, Burkholderia vietnamiensis, Burkholderia dolosa, Burkholderia ambifaria, Burkholderia anthina, Burkholderia pyrrocinia, Burkholderia gladioli, Burkholderia ubonensis, Burkholderia arboris, Burkholderia latens, Burkholderia lata, Burkholderia metallica, Burkholderia seminalis, Burkholderia contaminans*, and *Burkholderia diffusa*.

In some embodiments, the bacteria are drug resistant, and in some aspects of these embodiments, the bacteria are multi-drug resistant. For example, the bacteria may be resistant to antibiotics such as amikacin, aztreonam, methicillin, vancomycin, nafcillin, gentamicin, ampicillin, chloramphenicol, doxycycline, colistin, delamanid, pretomanid, clofazimine, bedaquiline, and/or tobramycin.

The bacteria may develop resistance to these drugs, but cannot easily develop resistance to the nitric oxide-based approaches described herein.

Types of Viral Infections that can be Treated

RNA and DNA viruses that can be treated are summarized below.

RNA Viruses

Currently, there are 5 recognized orders and 47 families of RNA viruses, and there are also many unassigned species and genera. Related to but distinct from the RNA viruses are the viroids and the RNA satellite viruses.

There are several main taxa: levivirus and related viruses, picornaviruses, alphaviruses, flaviviruses, dsRNA viruses, and the -ve strand viruses (Wolf et al., "Origins and Evolution of the Global RNA Virome," mBio, 9(6) (November 2018)).

Positive strand RNA viruses are the single largest group of RNA viruses, with 30 families. Of these, there are three recognized groups. The picorna group (Picornavirata) includes bymoviruses, comoviruses, nepoviruses, nodaviruses, picornaviruses, potyviruses, obemoviruses and a subset of luteoviruses (beet western yellows virus and potato leafroll virus). The flavi-like group (Flavivirata) includes carmoviruses, dianthoviruses, flaviviruses, pestiviruses, statoviruses, tombusviruses, single-stranded RNA bacteriophages, hepatitis C virus and a subset of luteoviruses (barley yellow dwarf virus). The alpha-like group (Rubivirata) includes alphaviruses, carlaviruses, furoviruses, hordeiviruses, potexviruses, rubiviruses, tobraviruses, tricornaviruses, tymoviruses, apple chlorotic leaf spot virus, beet yellows virus and hepatitis E virus.

A division of the alpha-like (Sindbis-like) supergroup has been proposed, with two proposed groups. The 'altovirus' group includes alphaviruses, furoviruses, hepatitis E virus, hordeiviruses, tobamoviruses, tobraviruses, tricornaviruses and rubiviruses, and the 'typovirus' group includes apple chlorotic leaf spot virus, carlaviruses, potexviruses and tymoviruses.

There are five groups of positive-stranded RNA viruses containing four, three, three, three, and one order(s), respectively. These fourteen orders contain 31 virus families (including 17 families of plant viruses) and 48 genera (including 30 genera of plant viruses). Alphaviruses and flaviviruses can be separated into two families, the Togaviridae and Flaviridae.

This analysis also suggests that the dsRNA viruses are not closely related to each other but instead belong to four additional classes, Birnaviridae, Cystoviridae, Partitiviridae, and Reoviridae, and one additional order (Totiviridae) of one of the classes of positive ssRNA viruses in the same subphylum as the positive-strand RNA viruses.

There are two large clades: One includes the families Caliciviridae, Flaviviridae, and Picornaviridae and a second that includes the families Alphatetraviridae, Birnaviridae, Cystoviridae, Nodaviridae, and Permutotetraviridae.

Satellite viruses include Albetovirus, Aumaivirus, Papanivirus, Virtovirus, and Sarthroviridae, which includes the genus Macronovirus.

Double-stranded RNA viruses (dsRNA viruses) include twelve families and a number of unassigned genera and species recognized in this group. The families include Amalgaviridae, Birnaviridae, Chrysoviridae, Cystoviridae, Endornaviridae, Hypoviridae, Megabirnaviridae, Partitiviridae, Picobirnaviridae, Reoviridae, which includes Rotavirus, Totiviridae, Quadriviridae. Botybirnavirus is one genus, and unassigned species include *Botrytis porri* RNA virus 1, *Circulifer tenellus* virus 1, *Colletotrichum camelliae* filamentous virus 1, Cucurbit yellows associated virus, *Sclerotinia sclerotiorum* debilitation-associated virus, and *Spissistilus festinus* virus 1.

Positive-sense ssRNA viruses (Positive-sense single-stranded RNA viruses) include three orders and 34 families, as well as a number of unclassified species and genera. The order Nidovirales includes the families Arteriviridae, Coronaviridae, which includes Coronaviruses, such as SARS-CoV and SARS-CoV-2, Mesoniviridae and Roniviridae. The order Picornavirales includes families Dicistroviridae, Iflaviridae, Marnaviridae, Picornaviridae, which includes Poliovirus, Rhinovirus (a common cold virus), and Hepatitis A virus, Secoviridae, which includes the subfamily Comovirinae, as well as the genus Bacillariornavirus and the species Kelp fly virus. The order Tymovirales includes the families Alphaflexiviridae, Betaflexiviridae, Gammaflexiviridae, and Tymoviridae. A number of families are not assigned to any of these orders, and these include Alphatetraviridae, Alvernaviridae, Astroviridae, Barnaviridae, Benyviridae, Botourmiaviridae, Bromoviridae, Caliciviridae, which includes the Norwalk virus (i.e., norovirus), Carmotetraviridae, Closteroviridae, Flaviviridae, which includes Yellow fever virus, West Nile virus, Hepatitis C virus, Dengue fever virus, and Zika virus, Fusariviridae, Hepeviridae, Hypoviridae, Leviviridae, Luteoviridae, which includes Barley yellow dwarf virus, Polycipiviridae, Narnaviridae, Nodaviridae, Permutotetraviridae, Potyviridae, Sarthroviridae, Statovirus, Togaviridae, which includes Rubella virus, Ross River virus, Sindbis virus, and Chikungunya virus, Tombusviridae, and Virgaviridae. Unassigned genuses include Blunervirus, Cilevirus, Higrevirus, Idaeovirus, Negevirus, Ourmiavirus, Polemovirus, Sinaivirus, and Sobemovirus. Unassigned species include *Acyrthosiphon pisum* virus, Bastrovirus, Blackford virus, Blueberry necrotic ring blotch virus, Cadicistrovirus, *Chara australis* virus, Extra small virus, Goji berry chlorosis virus, *Harmonia axyridis* virus 1, Hepelivirus, Jingmen tick virus, Le Blanc virus, Nedicistrovirus, *Nesidiocoris tenuis* virus 1, Niflavirus, *Nylanderia fulva* virus 1, Orsay virus, *Osedax japonicus* RNA virus 1, Picalivirus, Planarian secretory cell nidovirus, Plasmopara *halstedii* virus, Rosellinia necatrix fusarivirus 1, Santeuil virus. Secalivirus, *Solenopsis invicta* virus 3, and Wuhan large pig roundworm virus.

Satellite viruses include the family Sarthroviridae and the genuses Albetovirus, Aumaivirus, Papanivirus, Virtovirus, and the Chronic bee paralysis virus. Six classes, seven orders and twenty four families are currently recognised in this group. A number of unassigned species and genera are yet to be classified Negative-sense ssRNA viruses (Negative-sense single-stranded RNA viruses) are, with the exception of the Hepatitis D virus, within a single phylum, Negarnaviricota, with two subphyla, Haploviricotina and Polyploviricotina, with four classes, Chunqiuviricetes, Milneviricetes, Monjiviricetes and Yunchangviricetes. The subphylum Polyploviricotina has two classes, Ellioviricetes and Insthoviricetes.

There are also a number of unassigned species and genera. The Phylum Negarnaviricota includes Subphylum Haploviricotina, Class Chunqiuviricetes, Order Muvirales, Family Qinviridae. The Class Milneviricetes includes Order Serpentovirales and Family Aspiviridae. The Class Monjiviricetes includes Order Jingchuvirales and Family Chuviridae. The order Mononegavirales includes familes Bornaviridae, which includes the Borna disease virus, Filoviridae, which includes the Ebola virus and the Marburg virus, Mymonaviridae, Nyamiviridae, Paramyxoviridae, which includes Measles, Mumps, Nipah, Hendra, and NDV, Pneumoviridae, which RSV and Metapneumovirus, Rhabdoviridae, which Rabies, and Sunviridae, as well as genuses Anphevirus, Arlivirus, Chengtivirus, Crustavirus, and Wastrivirus. Class Yunchangviricetes includes order Goujianvirales and family Yueviridae.

Subphylum Polyploviricotina includes class Ellioviricetes, order Bunyavirales, and the families Arenaviridae, which includes Lassa virus, Cruliviridae, Feraviridae, Fimoviridae, Hantaviridae, Jonviridae, Nairoviridae, Peribunyaviridae, Phasmaviridae, Phenuiviridae, Tospoviridae, as well as genus Tilapineviridae.

Class Insthoviricetes includes order Articulavirales and family Amnoonviridae, which includes the Taastrup virus, and family Orthomyxoviridae, which includes Influenza viruses.

The genus Deltavirus includes the Hepatitis D virus.

Specific viruses include those associated with infection of mucosal surfaces of the respiratory tract, including Betacoronavirus (SARS-COV-2 and MERS-COV), rhinoviruses, influenza virus (including influenza A and B), parainfluenza). Generally, orthomyxoviruses and paramyxoviruses can be treated.

DNA Viruses

A DNA virus is a virus that has DNA as its genetic material and replicates using a DNA-dependent DNA polymerase. The nucleic acid is usually double-stranded DNA (dsDNA) but may also be single-stranded DNA (ssDNA). DNA viruses belong to either Group I or Group II of the Baltimore classification system for viruses. Single-stranded DNA is usually expanded to double-stranded in infected cells. Although Group VII viruses such as hepatitis B contain a DNA genome, they are not considered DNA viruses according to the Baltimore classification, but rather reverse transcribing viruses because they replicate through an RNA intermediate. Notable diseases like smallpox, herpes, and the chickenpox are caused by such DNA viruses.

Some have circular genomes (Baculoviridae, Papovaviridae and Polydnaviridae) while others have linear genomes (Adenoviridae, Herpesviridae and some phages). Some families have circularly permuted linear genomes (phage T4 and some Iridoviridae). Others have linear genomes with covalently closed ends (Poxviridae and Phycodnaviridae).

Fifteen families are enveloped, including all three families in the order Herpesvirales and the following families: Ascoviridae, Ampullaviridae, Asfarviridae, Baculoviridae, Fuselloviridae, Globuloviridae, Guttaviridae, Hytrosaviridae, Iridoviridae, Lipothrixviridae, Nimaviridae and Poxviridae.

Of these, species of the order Herpesvirales, which includes the familes Alloherpesviridae, Herpesviridae, which includes human herpesviruses and the Varicella Zoster, and the families Adenoviridae, which includes viruses which cause human adenovirus infection, and Malacoherpesviridae, infect vertebrates.

Asfarviridae, which includes African swine fever virus, Iridoviridae, Papillomaviridae, Polyomaviridae, which includes Simian virus 40, JC virus, and BK virus, and Poxviridae, which includes Cowpox virus and smallpox, infect vertebrates. Anelloviridae and Circoviridae also infect animals (mammals and birds respectively).

The family Smacoviridae includes a number of single-stranded DNA viruses isolated from the feces of various mammals, and there are 43 species in this family, which includes six genera, namely, Bovismacovirus, Cosmacovirus, Dragsmacovirus, Drosmacovirus, Huchismacovirus and Porprismacovirus. Circo-like virus Brazil hs1 and hs2 have also been isolated from human feces. An unrelated group of ssDNA viruses includes the species bovine stool associated circular virus and chimpanzee stool associated circular virus.

Animal viruses include parvovirus-like viruses, which have linear single-stranded DNA genomes, but unlike the parvoviruses, the genome is bipartate. This group includes Hepatopancreatic parvo-like virus and Lymphoidal parvo-like virus. Parvoviruses have frequently invaded the germ lines of diverse animal species including mammals.

The human respiratory-associated PSCV-5-like virus has been isolated from the respiratory tract.

Representative viruses associated with lung infections that can be treated using the methods described herein include Coronavirus, Picornavirus, influenza virus (including influenza A and B), common cold, respiratory syncytial virus (RSV), adenovirus, parainfluenza, rhinoviruses, and SARS). Generally, orthomyxoviruses and paramyxoviruses can be treated.

In addition to viruses associated with respiratory infections, causing bronchitis, sinusitis, and/or pneumonia, the human papilloma virus (HPV) is associated with certain throat cancers.

Types of Fungal Infections that can be Treated

Representative fungal infections that can be treated include *Candida albicans*, drug resistant *Candida albicans*, *Candida glabrata, Candida krusei, Candida guilliermondii, Candida auris, Candidatropicalis, Aspergillus niger, Aspergillus terreus, Aspergillus fumigatus*, and/or *Aspergillus flavus*.

V. Methods of Treatment

The compounds disclosed herein can be used in anti-infective/antimicrobial applications. Depending on the location of the infection, the compounds and/or compositions discussed herein can be administered by inhalation, nebulization, intranasal delivery, direct injection or application to, for example, an infected tissue. Administration can also include parenteral administration (e.g., intravenous, intramuscular, or intraperitoneal injection), subcutaneous administration, administration into vascular spaces, and/or administration into joints (e.g., intra-articular injection).

The compounds can also be administered via topical, vaginal, rectal, buccal, intrathecal, and intraarterial administration, or applied as a liquid or gel to a site of treatment.

In several embodiments, the compounds allow the efficient reduction in viability and/or eradication of microbes (e.g., prokaryotic cells, bacteria, protozoa, fungi, algae, amoebas, slime molds, etc.). In particular, such compounds are effective against such microbes that have developed at least some degree of drug resistance to traditional antimicrobial or antiviral therapies alone or in combination with other known antimicrobial or antiviral therapies.

Unlike conventional antimicrobial treatments, NO, an endogenously produced free radical, eradicates bacteria using a variety of mechanisms, including, but not limited to, lipid peroxidation, nitrosation of membrane proteins, and DNA damage via reactive oxygen/nitrogen species (e.g., peroxynitrite, dinitrogen trioxide). Multiple biocidal mechanisms allow NO to significantly diminish the risk of fostering microbial resistance. Furthermore, NO has the improved ability to actively degrade both a biofilm matrix and mucus structure, thus allowing for more efficient biocidal action and mucociliary clearance in infections associated with biofilms and/or excess mucous.

NO is also a potent antibacterial agent that acts on bacteria via nitrosative and/or oxidative stress. NO is a broad-spectrum antibacterial agent and in some embodiments, the compounds described herein deliver NO, and are therefore capable of eradicating both bacteria and biofilms, potentially through the formation of reactive NO byproducts (e.g., peroxynitrite and dinitrogen trioxide) that cause oxidative and nitrosative damage to microbial DNA and/or membrane structures. Advantageously, the wide range of mechanisms by which NO exerts its antibacterial effects reduces the risk that bacteria will develop resistance. Thus, NO-releasing compounds described herein are useful for combatting bacterial infections. The antibacterial efficacy of NO-releasing materials is dependent on both NO payloads and associated release kinetics. In some instances, high NO total is an important parameter to effectively evaluate storage capability of suitable compounds. However, NO release that is too fast, and high NO storage, can result in undesired toxicity to mammalian cells. Therefore, challenges exist in preparing biocompatible NO-releasing materials with high NO storage and low cytotoxicity, and such challenges, among others, are addressed according to several embodiments disclosed herein.

Real-time detection of NO can be performed using a chemiluminescence-based nitric oxide analyzer (NOA). The total NO storage and dissociation kinetics of water-soluble NO Donors were measured in physiological condition (pH 7.40, 37° C.). The resulting NO-release parameters (e.g., total NO storage, half-life of NO release, maximum flux, and conversion efficiency) were evaluated for suitability as a pharmaceutical product. In general, small molecule derivatives of many compounds can be designed to exhibit large NO storage capabilities with consistent NO-release kinetics (e.g., species which consistently have NO-release half-lives from 0.5 h to 24+ h).

Treatment of Drug-Resistant Bacteria

In several embodiments, the microbial load to be reduced and/or eliminated comprises drug-resistant bacteria. In several embodiments, the drug-resistant bacteria comprise carbapenem-resistant Enterobacteriaceae. In several embodiments, the drug-resistant bacteria comprise Methicillin-resistant *Staphylococcus aureus*. In several embodiments, the microbe comprises human immunodeficiency virus, herpes simplex virus, papilloma virus, parainfluenza virus, influenza, hepatitis, Coxsackie Virus, herpes zoster, measles, mumps, rubella, rabies, pneumonia, (hemorrhagic viral fevers, H1N1, and the like), prions, parasites, fungi, mold, yeast and bacteria (both gram-positive and gram-negative) including, among others, *Candida albicans, Aspergillus niger, Escherichia coli* (*E. coli*), *Pseudomonas aeruginosa* (*P. aeruginosa*), and *Staphylococcus aureus* (*S. aureus*), Group A streptococci, *S. pneumoniae, Mycobacterium tuberculosis, Campylobacter jejuni, Salmonella, Shigella, P. gingivalis, A. actinomycetemcomitans, A. viscosus*, and/or *S. mutans* and a variety of drug resistant bacteria. The terms microorganism and microbe shall be used interchangeably. Microbes can include wild-type, genetically-engineered or modified organisms.

Treatment of Pulmonary Infections

The methods described herein can be used to treat, prevent, manage or lessen the severity of symptoms and infections associated with one or more pulmonary diseases or infections in a subject. The methods involve administering one or more of the compounds described herein to the subject. The compounds can be administered to the mouth, nasal passages, throat, esophagus, larynx, pharynx, trachea, bronchioles, bronchi, upper airways, lower airways, subcutaneously or via an implant (for example, up under the ribs and into the chest cavity), and combinations thereof.

In some embodiments, the compounds are nebulized, inhaled, or delivered intranasally. In one specific embodiment, the methods comprise inhalation of particles including one or more of the compounds described herein aerosolized via nebulization. Nebulizers generally use compressed air or ultrasonic power to create inhalable aerosol droplets of the particles or suspensions thereof. In this embodiment, the nebulizing results in pulmonary delivery to the subject of aerosol droplets of the particles or suspension thereof. In another embodiment, the methods comprise inhalation of particles aerosolized via a pMDI, wherein the particles or suspensions thereof are suspended in a suitable propellant system (including but not limited to hydrofluoroalkanes (HFAs) containing at least one liquefied gas in a pressurized container sealed with a metering valve. Actuation of the valve results in delivery of a metered dose of an aerosol spray of the particles or suspensions thereof.

In one embodiment, the compounds are administered during lung lavage, which can be whole lung lavage or bronchoalveolar lavage (BAL). In BAL, also known as bronchoalveolar washing, a bronchoscope is passed through the mouth or nose into the lungs and fluid is squirted into a small part of the lung and then collected for examination. The compounds can travel through the fluid, and treat the entire fluid-coated portion of the lung.

Bronchoalveolar lavage is commonly used to diagnose infections in people with immune system problems, pneumonia in people on ventilators, some types of lung cancer, and scarring of the lung (interstitial lung disease). It is the most common method used to sample the epithelial lining fluid (ELF) and to determine the protein composition of the pulmonary airways. It is often used in immunological research as a means of sampling cells (for example, T cells) or pathogen levels (for example, influenza virus) in the lung. During the procedure, the compounds described herein can be administered. Whole lung lavage (WLL; or "lung washing") is a treatment for pulmonary alveolar proteinosis. While the lung is washed, therapy with the compounds can also be administered, and the fluid allows the compounds to contact the entire fluid-coated surface of the lung.

In some embodiments, the compounds are used to treat or prevent microbial infections, including those caused by viruses such as Coronavirus, including SARS, MERS, and SARS-CoV2.

In other embodiments, the infection is caused by a spore-forming microbe, such as certain bacteria and all fungi. Because most pharmaceuticals are only active against the bacteria or fungus when it is not in spore form, the treatments must take place over an extended period of time, so that the spores can become active bacteria/fungi, and then be treated with the antimicrobial agents.

The compounds described herein are effective not only at killing active bacteria/fungi, but also against spores. Accordingly, using the methods described herein, one can lessen the duration of treatment. By way of example, treatment of infections such as tuberculosis or NTM (non-tuberculosis mycobacterial infections) takes around 1 year for an effective treatment, largely because of the continued presence of spores. The duration of treatment often leads to poor patient compliance, particularly with respect to patients co-infected with HIV, because the drugs commonly used to treat HIV are incompatible with the drugs used to treat tuberculosis. The main source of drug interactions in the management of TB/HIV co-infection is through the effects of the antibacterial compound rifampicin inducing the cytochrome P450 system, which affects metabolism of many drugs used to treat HIV. The methods described herein can be used to minimize treatment time, thus increasing patient compliance, and minimize or avoid the issues associated with drug interactions with drugs used to treat HIV.

In one aspect, the pulmonary diseases or infections the result of or associated with cystic fibrosis. Carbocysteine is a mucolytic agent that can help break down the mucous, and can be co-administered with the compounds described herein.

In another aspect, the subject has at least one pulmonary infection, and if there are two or more pulmonary infections, the infections are either concurrent or successive in order.

In some aspects, the pulmonary infections are in one lung, and in other aspects, in both lungs, and can be in one or more of the three lobes of the right lung, or one or both of the two lobes of the left lung.

Examples of pulmonary infections that can be treated include bronchiectasis infection, pneumonia, valley fever, allergic bronchopulmonary aspergillosis (ABPA), ventilator acquired pneumonia, hospital acquired pneumonia, community acquired pneumonia, ventilator associated tracheobronchitis, lower respiratory tract infection, non-tuberculous Mycobacteria, anthrax, legionellosis, pertussis, bronchitis, Bronchiolitis, COPD-associated infection, and post-lung transplantation.

The pulmonary infection can be caused by one or more bacterial or fungal pathogens.

Where the pulmonary infections are CF-related pulmonary infections, the methods described herein can be used to treat, manage, or lessen the severity of the CF-related pulmonary infection.

In some embodiments, the pulmonary infection is located in or on the lung mucosa, the bronchi and/or the bronchioles.

In some embodiments, the pulmonary infection is located on the surface of or within a bacterial biofilm, aggregated bacteria, a fungal biofilm, or aggregated fungi.

In still other embodiments, the pulmonary infection is located in the sputum.

The bacterial pathogen can be a gram-positive bacteria or gram-negative bacteria, and can include one or more of a bacterial biofilm and planktonic bacteria.

The compounds described herein can penetrate and disrupt biofilms, so in embodiments where a bacterial biofilm is present, the methods can involve (i) reducing the bacterial biofilm, (ii) impairing growth of the bacterial biofilm, and (iii) preventing reformation of the bacterial biofilm.

In still other embodiments, a fungal pathogen is present, which can include planktonic fungi and/or biofilm fungi.

The methods can be used to treat, manage or lessen the severity of the pulmonary infection by one or both of: prevention of the infection by the bacterial or fungal pathogen; reduction of the bacterial or fungal pathogen; and/or reducing the viscosity of the sputum.

The methods can treat, manage or lessen the severity of pulmonary infections by: preventing elaboration or secretion of exotoxins from the bacterial or fungal pathogen; inhibiting cell viability or cell growth of planktonic cells of the bacterial or fungal pathogen; inhibiting biofilm formation by the bacterial or fungal pathogen; and inhibiting biofilm viability or biofilm growth.

Representative pathogens which can be killed using the methods described herein include *Haemophilus influenzae, Pseudomonasaeruginosa, Staphylococcus aureus, Staphylococcus warneri Staphylococcus lugdunensis, Staphylococcus epidermidis, Streptococcus* milleri/anginous, *Streptococcus pyogenes,* non-tuberculosis *mycobacterium, Mycobacterium tuberculosis, Burkholderia* spp., *Achromobacter xylosoxidans, Pandoraeasputorum, Stenotrophomonas maltophilia, Alcaligenes xylosoxidans, Haemophilus pittmaniae, Serratia marcescens, Candidia albacans, Candida parapsilosis, Candida guilliermondii, Morganella morganii, Inquilinus limosus, Ralstonia mannitolilytica, Pandoraea apista, Pandoraea pnomenusa, Pandoraea sputorum, Bdellovibrio bacteriovorus, Bordetellabronchiseptica, Vampirovibrio chlorellavorus, Actinobacter baumanni, Cupriadidus metallidurans, Cupriavidus pauculus, Cupriavidus respiraculi, Delftia acidivordans, Exophilia dermatitidis, Herbaspirillum frisingense, Herbaspirillum seropedicae, Klebsiella pneumoniae, Pandoraea norimbergensis, Pandoraea pulmonicola, Pseudomonas mendocina, Pseudomonas pseudoalcaligenes, Pseudomonas putida, Pseudomonas stutzeri, Ralstonia insidiosa, Ralstonia pickettii, Neisseria gonorrhoeae,* NDM-1 positive *E. coli, Enterobacter cloaca,* Vancomycin-resistant *E. faecium,* Vancomycin-resistant *E. faecalis, E. faecium, E. faecalis,* Clindamycin-resistant *S. agalactiae, S. agalactiae, Bacteroides fragilis, Clostridium difficile, Streptococcus pneumonia, Moraxella catarrhalis, Haemophilus haemolyticus, Haemophilus parainfluenzae, Chlamydophilia pneumoniae, Mycoplasma pneumoniae, Atopobium, Sphingomonas, Saccharibacteria, Leptotrichia, Capnocytophaga, Oribacterium, Aquabacterium, Lachnoanaerobaculum, Campylobacter, Acinetobacter; Agrobacterium; Bordetella; Brevundimonas; Chryseobacterium, Delftia; Enterobacter; Klebsiella; Pandoraea; Pseudomonas; Ralstonia,* and *Prevotella.*

Common pulmonary infections include inhalation anthrax, whooping cough (also known as pertussis, and caused by *Bordetella pertussis), streptococcus* (pneumococcus, *Streptococcus pneumoniae),* mycobacteria, including mycobacteria tuberculosis and Nontuberculous mycobacterial (NTM) lung disease (*Mycobacterium avium* complex (MAC), M *abscessus, M kansasii, M. malmoense, M. szulgai,* and *M. xenopi*).

The methods described herein can lessen the severity of one or more of the following symptoms in a subject being treated: cough, wheezing, breathlessness, bronchiectasis, nasal polyps, hemoptysis, respiratory failure, and pulmonary exacerbation.

Administration of the Compounds Described Herein to Treat or Prevent Coronavirus Infection The compounds described herein can be delivered to one or more regions of the respiratory tract of a patient, for example, using nebulizers or nasal sprays, for a sufficient period of time, to treat or prevent a Coronavirus infection. The nitric oxide generated as the compounds degrade can be effective at treating or preventing a Coronavirus infection. Exposure to the compounds, and the nitric oxide produced by these compounds, is not significantly damaging to lung tissue, even if carried out for extended periods of time.

The compounds can be administered anywhere along the respiratory tract, depending on the status of the patient's infection. If the virus is not present in large quantities in the lung, and is largely limited to the patients mouth, nose, and throat, therapy can be limited to those regions of the respiratory tract.

This approach can also be used in a prophylactic manner for patients at risk for developing a Coronavirus infection, by virtue of having been, or suspected of having been, in contact with individuals with a Coronavirus infection.

If the patient's lungs are infected, then administration of the compounds directly to the lungs is more desirable. The compounds can be administered, for example, via a nebulizer. In addition to treating the viral infection, the compounds are also helpful in preventing secondary infections, such as bronchitis or pneumonia, which are caused by bacteria and which frequently follow viral infections. Minimization of the risk of secondary infection can, in some cases, be even more important than treatment of the underlying viral infection.

It can be important to follow the course of treatment, particularly where a patient has an active infection and could experience severe adverse consequences if the treatment is not successful, or has a disease such as COPD that progresses over time, and it can be important to monitor the progression of the disease.

Methods of following the progress of the treatment include taking periodic readings with a pulse oximeter, and taking periodic chest X-Rays/ultrasounds/CT scans. One can also checking for residual microbial infection, for example, using ELISA tests, or other tests which look for antibodies specific to certain microbial infections, as well as analyzing blood or sputum samples for residual infection. A patient's body temperature can be followed as well, particularly for following the treatment of microbial infections in the short-term.

For pulmonary inflammatory disorders, it can be useful to follow the course of treatment with periodic lung function tests, which can include spirometry, as well as performance tests (such as the distance a patient can walk in a given time period).

Treatment of Cystic Fibrosis

Cystic fibrosis (CF) is a genetic disorder characterized by poor mucociliary clearance and chronic bacterial infections. As shown herein, in several embodiments, nitric oxide (NO) has broad spectrum antibacterial activity against CF-relevant bacteria, making it an attractive alternative to traditional antibiotics. Treatment with NO limits bacterial resistance due to its multiple biocidal mechanisms (e.g., induction of nitrosative and oxidative stress). It has surprisingly been found that by storing NO on the compound described herein, bactericidal efficacy is improved and systemic cytotoxicity is reduced. Treatments are effective against planktonic and biofilm-based pathogens, and cytotoxicity assays against mammalian lung cells demonstrate little harm to a treated subject's cells. It has also surprisingly been found that the combination of gallium and a NO donor is synergistically effective.

CF is a debilitating disease characterized by chronic bacterial infection of the lungs, resulting in life expectancies as low as two decades. A genetic defect in the CF transmembrane conductance regulator (CFTR) impedes the normal transport of ions (e.g., $Cl^-$) to the airway surface liquid, inhibiting water transport. As such, the airway epithelium dehydrates, creating thickened mucus that can no longer be efficiently cleared via mucociliary clearance mechanisms. As goblet cells continually excrete mucins into the dehydrated airway, mucus accumulation is accelerated to the point where the cilia become damaged, or nonfunctional, and are unable to clear mucus from the airway. Planktonic bacteria thrive in this static environment, promoting the formation of complex communities of pathogenic bacteria known as biofilms. The exopolysaccharide matrix produced by these biofilms inhibits oxygen diffusion, creating pockets of anaerobic environments and altering bacterial metabolism. This combination of a concentrated mucus layer and robust biofilms severely decreases the antibacterial efficacy of common CF therapies.

Inflammatory Lung Disorders

There are a number of additional pulmonary disorders with an inflammatory component. Representative disorders include asthma, COPD, chronic bronchitis, emphysema (and co-administration of the compounds described herein with Retinoids like Retin-A can help rebuild alveoli), acute bronchitis (viral or bacterial), lung diseases affecting the air sacs (alveoli) and/or interstitium include pneumonia, tuberculosis (caused by the bacteria *Mycobacterium tuberculosis*), emphysema, pulmonary edema, whether caused by COPD, heart failure, or direct injury to the lung, lung cancer, acute respiratory distress syndrome (ARDS), pneumoconiosis, interstitial lung disease (ILD), sarcoidosis, idiopathic pulmonary fibrosis, and autoimmune disease.

Disorders such as asthma, chronic obstructive pulmonary disease (COPD), and pulmonary fibrosis are the result of ongoing inflammatory processes. Asthma is an ongoing disease of the bronchial tubes, where the airways overreact to external factors like smoke, air pollution, and allergens. The bronchial tubes become narrower due to the ensuing inflammation in the tissue lining the airways. This then produces the symptom of dyspnea, where the patient complains of trouble breathing and has difficulty moving air in and out of the lungs.

COPD is another inflammatory disease where both the airways and lung tissue are affected. This can manifest as a combination of chronic obstructive bronchitis and emphysema, where the former is the result of chronic inflammation of the bronchial tubes and the latter is due to breakdown of the alveoli.

Pulmonary fibrosis is another chronic lung disease that is due to scarring or thickening of the lungs, which affects oxygen exchange.

Symptoms for these lung diseases include trouble breathing, shortness of breath, inability or decreased ability to exercise, coughing with or without blood or mucus, and pain when breathing in or out. For asthma, wheezing and chest tightness are common symptoms along with coughing and shortness of breath. COPD patients usually present with a chronic cough with large amounts of mucus production, as well as similar symptoms to that of asthma. Pulmonary fibrosis can produce a dry cough as well as fatigue, unexplained weight loss, and musculoskeletal pain.

Chest x-rays can show scar tissue, lung hyperinflation, flattened hemidiaphragms, or bronchial wall thickening. Computerized tomography scans, spirometry, arterial blood gas, and other tests may be appropriate depending on clinical presentation and history.

Conventional therapies for lung disease can be effective in symptomatic treatment but are not curative. Treatment initially consists of corticosteroids, beta agonists, leukotriene modifier or receptor antagonists, or methylxanthines like theophylline. In the early stages of lung disease, these medications can be given as monotherapy, but as the disease progresses, treatment is more likely to consist of multiple medications as well as supplemental oxygen and pulmonary rehabilitation.

Patients suffering from these disorders can benefit from treatment with the compounds described herein. Because patients suffering from inflammatory respiratory disorders often have an underlying microbial infection, it can be useful to combine anti-inflammatory compounds with the NO-producing compounds to both treat the inflammatory lung disease and the respiratory infections.

Depending on the particular lung disorder to be treated, the course of therapy can be followed in different ways. The treatment of microbial infections can be followed, for example, by following the severity of the symptoms, the presence of fever, the use of pulse oximetry, and the like. The treatment of pulmonary inflammatory disorders can be followed by X-ray, lung function tests, and the like. Challenge tests are lung function tests used to help confirm a diagnosis of asthma, where a patient inhales a small amount of a substance known to trigger symptoms in people with asthma, such as histamine or methacholine. After inhaling the substance, lung function is evaluated. Following therapeutic treatment, one can determine whether diminution of lung function following inhalation of these substances is lessened, relative to before therapy was initiated, which indicates that the therapy is effective for such a patient.

Treatment of Dental Caries

Dental caries (e.g., tooth decay) is another important disease state that affects 60%-70% school age children and the majority of adults in most industrialized countries. Worldwide, 11% of the total population suffers from severe periodontitis, which contributes to tooth loss and systematic diseases such as coronary, cardiovascular, stroke, and adverse pregnancy outcomes. Of >700 microorganisms in the oral cavity, cariogenic bacteria (e.g., *Streptococcus mutans, Actinomyces viscosus*) and periodontal pathogens (e.g., *Porphyromonas gingivalis, Aggregatibacter actinomycetemcomitans*) play a major role in the initiation and progression of oral diseases. Oral disease is among the most prevalent health problems faced by humans. Gram-positive cariogenic (e.g., *Streptococcus mutans, Actinomyces viscosus*) and Gram-negative periodontal (e.g., *Porphyromonas gingivalis, Aggregatibacter actinomycetemcomitans*) bacteria represent the main aggravators associated with the evolution and progression of dental caries and periodontal disease, respectively. Unfortunately, current treatments to combat these pathogens come with undesirable side effects. For example, the systemic use of antibiotics may result in gastrointestinal disturbance and foster bacterial resistance. Chlorhexidine, a common oral antiseptic, can alter taste, stain teeth and tongue, and irritate buccal mucosa. Macromolecule NO-delivering vehicles (e.g., silica nanoparticles, gold, etc.) kill Gram-negative periodontal pathogens. However, these materials have not been demonstrated to kill Gram-positive cariogenic bacteria at a safe concentration (e.g., a concentration that is bacteriocidal but non-toxic towards mammalian cells) Similar with those nanomaterials, the lack of biodegradability and potential cytotoxicity of the silica nanoparticles also hinders their future for biomedical application. Current research also focuses on utilizing nanomaterials including silver, gold, zinc, and copper, as replacement for traditional antibiotics that suffered from fostering bacterial resistance. However, these nanomaterials may accumulate inside the body and may cause accumulative toxicity, limiting their future for certain applications. Developing oral therapeutics that are capable of killing those disease-causing bacteria is important to maintain a healthy oral cavity. In several embodiments, the compositions disclosed herein (including, for example, NO scaffolds), resolve one or more of these issues or others.

Providing Wound Care

An unmet need in the area of wound healing, general surgery, and orthopedic surgery is for an antimicrobial material that can release NO at a requisite rate, and that can degrade during a desired timeframe. This degradation rate can be made to comport (through appropriate formulation) with the healing cycle of each specific condition and/or can comport to a time where the wound is at high risk of infection. Examples of these conditions include procedures such as hernia repair, diabetic foot ulcer healing, and orthopedic tendon repairs to name only a few. In several embodiments, the compounds and materials disclosed herein are targeted towards compositions that have tailorable degradation times.

Some embodiments provide a method for treating a tissue defect comprising positioning any of the compounds described herein at, over, or into the tissue defect. In several embodiments, the tissue defect is a wound. Several embodiments provide a method for treating a wound, for performing tissue repair, and/or for providing tissue and organ supplementation. In several embodiments, the first step of treating a tissue defect, wound, and/or supplementing and replacing tissue involves identifying a patient in need of an antimicrobial scaffold to aid in the remedying and healing of a tissue defect, healing of a wound, or in need of a tissue supplement.

A non-limiting list of patients in need of an antimicrobial compound includes patients suffering tissue defects. In several embodiments, the patients in need of an antimicrobial scaffold suffer from wounds including those from burns, skin ulcers, lacerations, bullet holes, animal bites, and other wounds prone to infection. Antimicrobial compounds can also be used to treat diabetic foot ulcers, venous leg ulcers, pressure ulcers, amputation sites, in other skin trauma, or in the treatment of other wounds or ailments. Patients in need of an antimicrobial scaffold also include patients in need of repair and supplementation of tendons, ligaments, fascia, and dura mater. The compounds can also be used in supplement tissue in procedures including, but not limited to, rotator cuff repair, Achilles tendon repair, leg or arm tendon or ligament repair (e.g., torn ACL), vaginal prolapse repair, bladder slings for urinary incontinence, breast reconstruction following surgery, hernia repair, staple or suture line reinforcement, bariatric surgery repair, pelvic floor reconstruction, dural repair, gum repair, bone grafting, and reconstruction. Further, a patient in need of an antimicrobial scaffold also includes one in need of tissue or organ replacement. In several embodiments, the compositions described herein can be used as fillers and/or to supplement and/or replace tissue by acting as an artificial extracellular matrix. In such an application, an antimicrobial scaffold can be used to support cell and tissue growth. Briefly, cells can be taken from a patient or a viable host and seeded on an antimicrobial scaffold either in vivo or ex vivo. Then as the patient's natural tissues invade the material, it is tailored to degrade and leave only naturally occurring tissues and cells free of bacterial infection.

In several embodiments, applications also include delivery of therapeutic molecules to a localized site, use as adhesives or sealants, and as viscosupplements, and in wound healing, among others. The stabilized compositions may also be used as tissue fillers, dermal fillers, bone fillers, bulking agents, e.g., as a urethral or an esophageal bulking agent, and embolic agents as well as agents to repair cartilage defects/injuries and agents to enhance bone repair and/or growth. In several embodiments, a composition comprising an antimicrobial scaffold can be placed in or on a patient in, for example, a void space to fill the space.

In several embodiments, the compounds are used to repair injured tissue. In several embodiments, the composition is formulated for administration to a target treatment site in a subject. For example, the composition may be formulated to facilitate administration to a damaged or infected tissue in a subject.

In several embodiments, after administration of the composition (e.g., gallium and NO donor, which comprises an antimicrobial scaffold), the composition may increase in temperature due to absorption of heat from surrounding body tissue of the subject. In several embodiments, the body temperature of the subject is sufficient to cause the composition to increase in viscosity (e.g., transition from a liquid to a gel. In several embodiments, the increase in viscosity (e.g., gelling) may give rise to a 3-dimensional network sufficient to provide structural and/or geometric support to a body tissue, such as a cardiac tissue (e.g., a cardiac tissue of an infarct region). In several embodiments, a syringe or catheter may be used to inject the composition in vivo. In several embodiments, the composition may be injected directly to the treatment site, or may be allowed to partially pre-heat in the syringe in order to increase the viscosity of the composition prior to injection. In several embodiments, a pre-heated formulation may reduce the possibility that a less viscous composition may diffuse and/or migrate away from the tissue area of interest after injection.

In several embodiments, after administration of the composition (e.g., comprising the antimicrobial compound of Formula III), the composition may increase in temperature due to absorption of heat from surrounding body tissue of the subject.

The present invention is further defined in the following Examples. It should be understood that these Examples, while indicating preferred embodiments of the invention, are given by way of illustration only.

EXAMPLES

Example 1: Synthesis and Characterization of the Compound of Formula III

This example pertains to the synthesis and identification of one embodiment of the compound of Formula III. This embodiment has the following features, advantages, and/or uses.

In several embodiments, this molecule has antibacterial properties with the NO-releasing material acting as an antibacterial agent. Compounds such as those disclosed were found to be the product of certain high pressure nitric oxide synthetic strategies. In this context, the compounds can form in trace to major components of the reaction, depending on reaction conditions, such as NO pressure, base content, temperature and, reactant content.

The methane trisdiazeniumdiolate, sodium salt, was prepared according to the following procedure in Table 1:

TABLE 1

Reaction parameters initially used to synthesize the compound of Formula III

| Substance | Mass/vol | mol | Eq. |
|---|---|---|---|
| NaOH | 6 g | 0.15 | 4 |
| MeOH | 150 mL | — | (40 mg/mL) |
| Acetone | 2.78 mL | 0.0325 | 1 |

NaOH was dissolved in MeOH
Acetone was added to the stirring solution.
Mixture was transferred to a 400 mL Parr reactor, which was equipped with stir bar.
Parr reactor was sealed.
3x $N_3$ Purge with 100 Psi of $N_2$ while stirring.
2.5 bar of NO charged into Parr vessel and allowed to stir at room temperature for 4 days.
The solution was cloudy with an off-white to slightly yellow precipitate.
The reaction solution was filtered via vacuum filtration using 110 mm GF/F filter paper.
A 15 mL aliquot of the filtrate was recovered and saved for testing if needed.
The solids collected during filtration were washed with 150 ml of MeOH.
The solids were dried overnight under vacuum at room temperature.
Recovery: 5.0 g + 4.2 g = 9.2 g off-white powder
NCT-19-168; $^1$HNMR = 7.4, 5.8.

The synthesized compound was isolated and tested to confirm identity. FTIR, HPLC, UV-Vis spectroscopy, $^1$H NMR and $^{13}$C NMR analysis were used to support the conclusions that the synthesis yielded the compound of Formula III.

Figure 2:
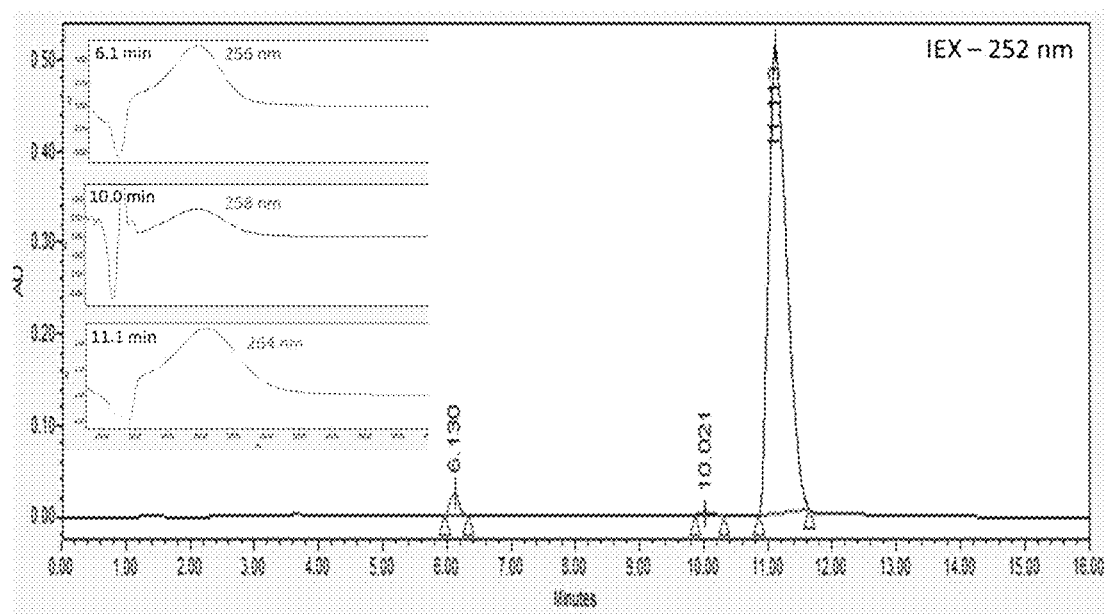
FIG. 2 shows an ion exchange chromatogram of a composition including the compound of Formula III with a retention time of 11 minutes ($\lambda$=252 nm). The UV absorbance spectrum of the analyte retained for approximately 6 minutes, the UV absorbance spectrum of the analyte retained for approximately 10 minutes, and the UV absorbance spectrum of the analyte retained for approximately 11 minutes are shown in the insets.

Referring now to FIG. 1, the FTIR spectrum is shown of the compound of Formula III according to the present disclosure. Referring now to FIG. 2, an ion exchange chromatogram is shown of the compound of Formula III with a retention time of 11 minutes (=252 nm). The UV absorbance spectrum of the analyte retained for approximately 6 minutes, the UV absorbance spectrum of the analyte retained for approximately 10 minutes, and the UV absorbance spectrum of the analyte retained for approximately 11 minutes are shown in the insets.

Figure 3:
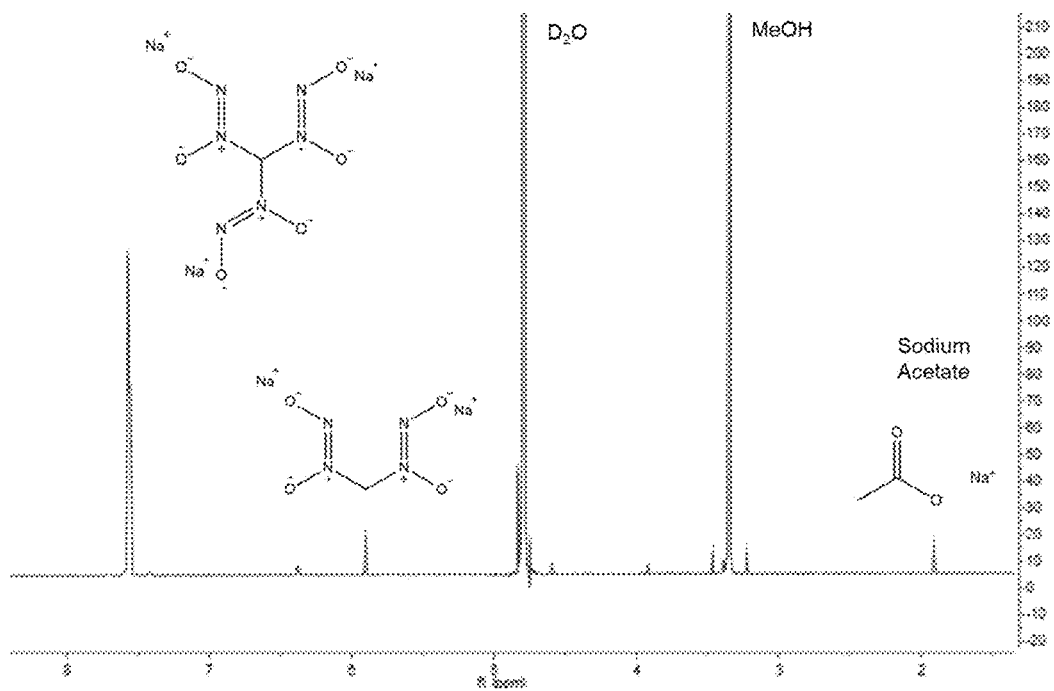
FIG. 3 shows the $^1$H NMR spectrum of the compound of Formula III in $D_2O$.
Figure 4:
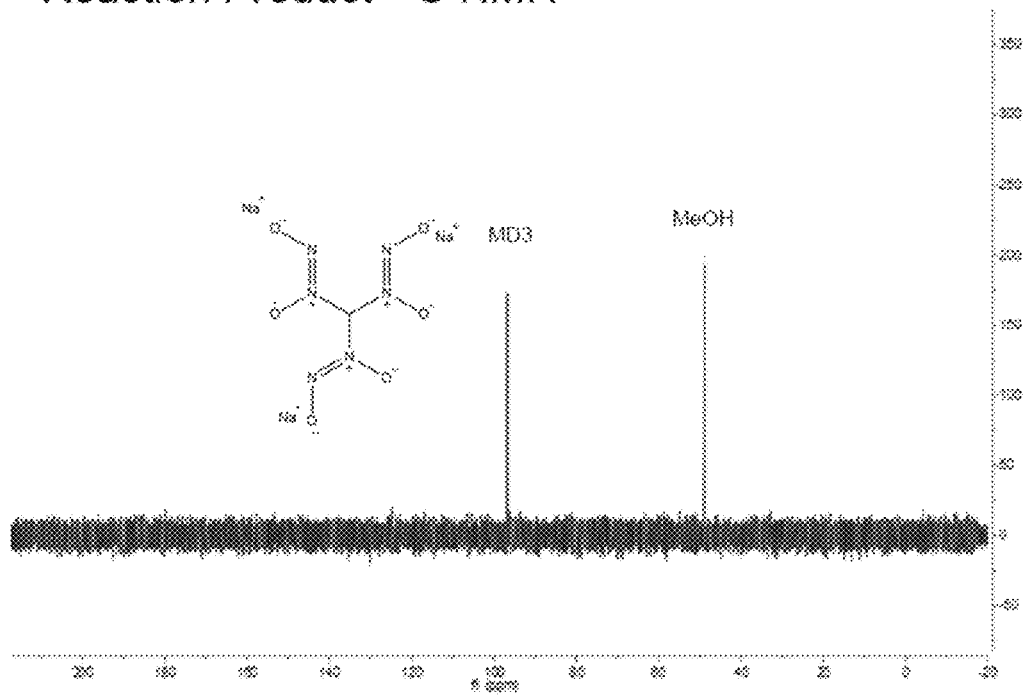
FIG. 4 shows the $^{13}$C NMR spectrum of the compound of Formula III
Figure 5:
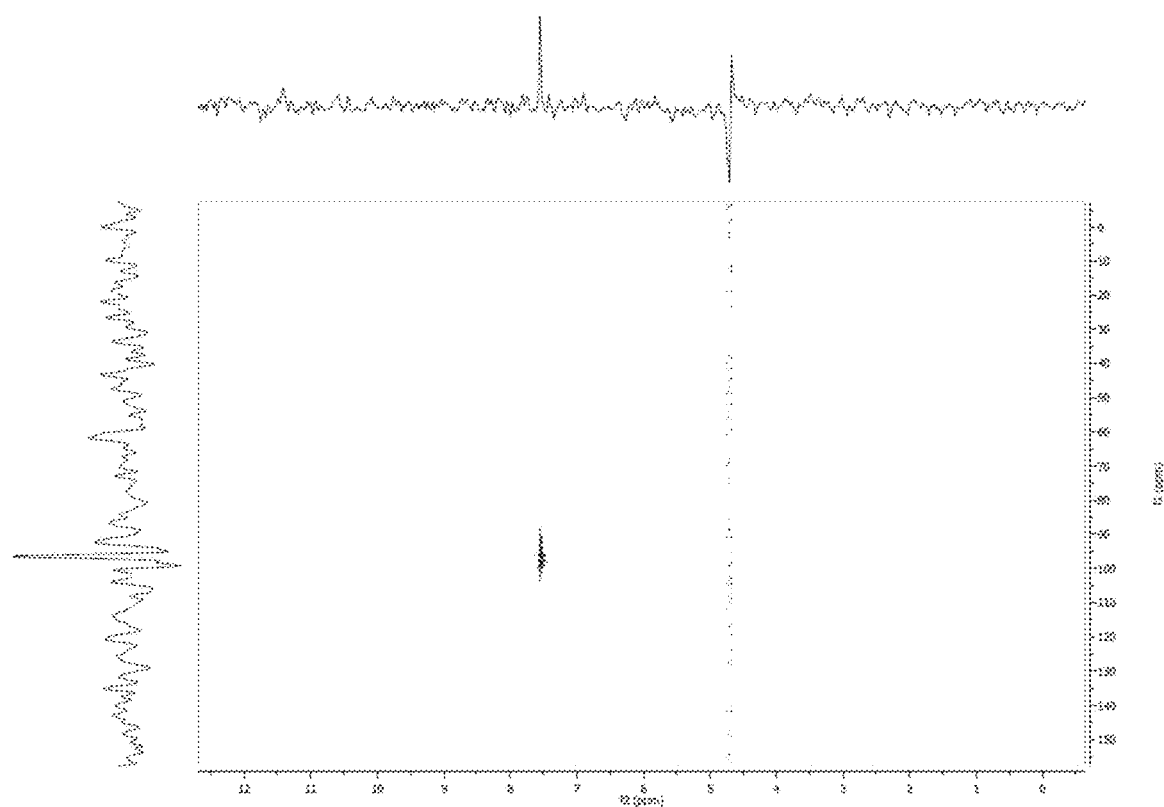
FIG. 5 shows the 2D NMR of the compound of Formula III.
Figure 6:
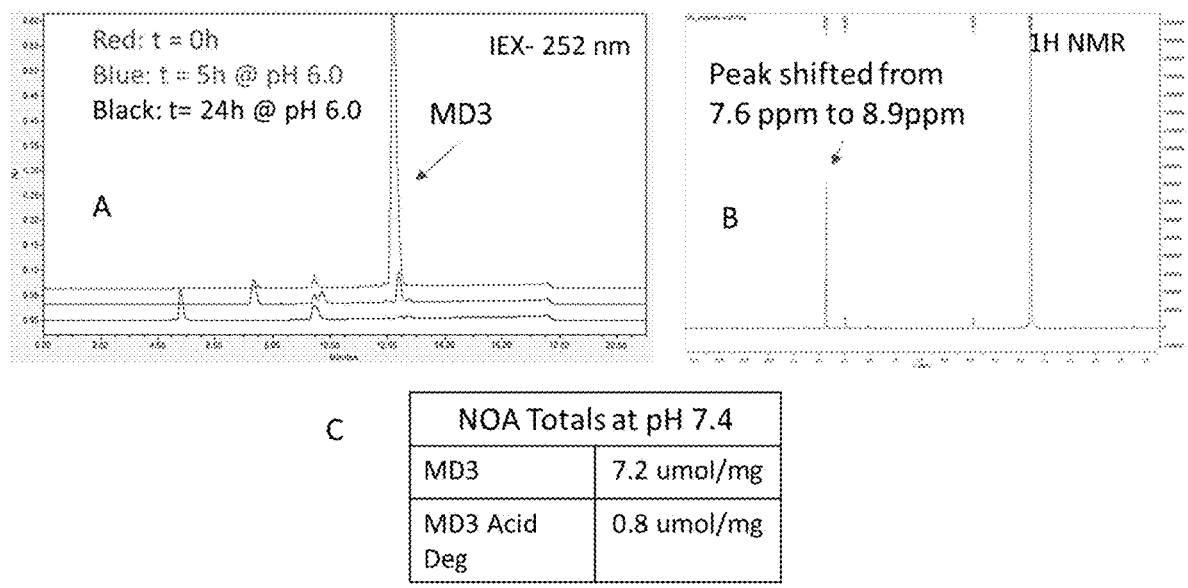
FIG. 6 shows A) HPLC chromatograms (IEX-UV) with the top chromatogram showing the separation of components prior to acid degradation of the compound of Formula III (referenced as MD3), the middle chromatogram showing the separation of components after 5 h of acid degradation, and the bottom chromatogram showing the separation of components after 24 h of acid degradation, B) the $^1$H NMR spectrum of the acid degraded components, C) a table of NOA Totals for compound of Formula III before and after acid degradation.

FIG. 3 shows the $^1$H NMR of the compound of Formula III. The peak at 7.5 ppm is assigned to the single proton on the compound of Formula III. FIG. 4 shows the $^{13}$C NMR of the compound of Formula III. The peak at 100 ppm is assigned to the single carbon on the compound of Formula III. FIG. 5 shows 2D NMR of the compound of Formula III. FIG. 6 shows A) HPLC chromatograms (IEX-UV) with the top chromatogram (red) showing the separation of components prior to acid degradation of the compound of Formula III (referenced as MD3), the middle chromatogram (blue) showing the separation of components after 5 h of acid degradation, and the bottom chromatogram (black) showing the separation of components after 24 h of acid degradation, B) the $^1$H NMR spectrum of the acid degraded components, C) a table of NOA Totals for the compound of Formula III before and after acid degradation. FIG. 7 is a $^1$H NMR spectrum and FIG. 8 is $^{13}$C NMR spectrum of a composition comprising the products of the compound of Formula III after degraded at neutral pH at room temperature.

Analytical results for the compound of Formula III are summarized in Table 2.

TABLE 2

Analytical test results compiled for the compound of Formula I.

| Test | Results |
|---|---|
| UV | $\lambda_{max}$ = 264 nm |
| IR | O-H and/or N-H (3436 $cm^{-1}$), Sharp C-H (3025 $cm^{-1}$), C = N (1649 $cm^{-1}$), N-O (1354, 1232 $cm^{-1}$) |
| H NMR | Singlet δ = 7.6 ppm, Singlet δ = 5.9 ppm |
| C13, 2D NMR | 1 peak at δ = 100 ppm, correlated to 7.6 ppm |
| C, N, H Analysis | C, 4.14%; N, 27.85%; H, 1.42% |
| XPS | C, O, N, Na confirmed |

Antimicrobial Activity

Figure 9:
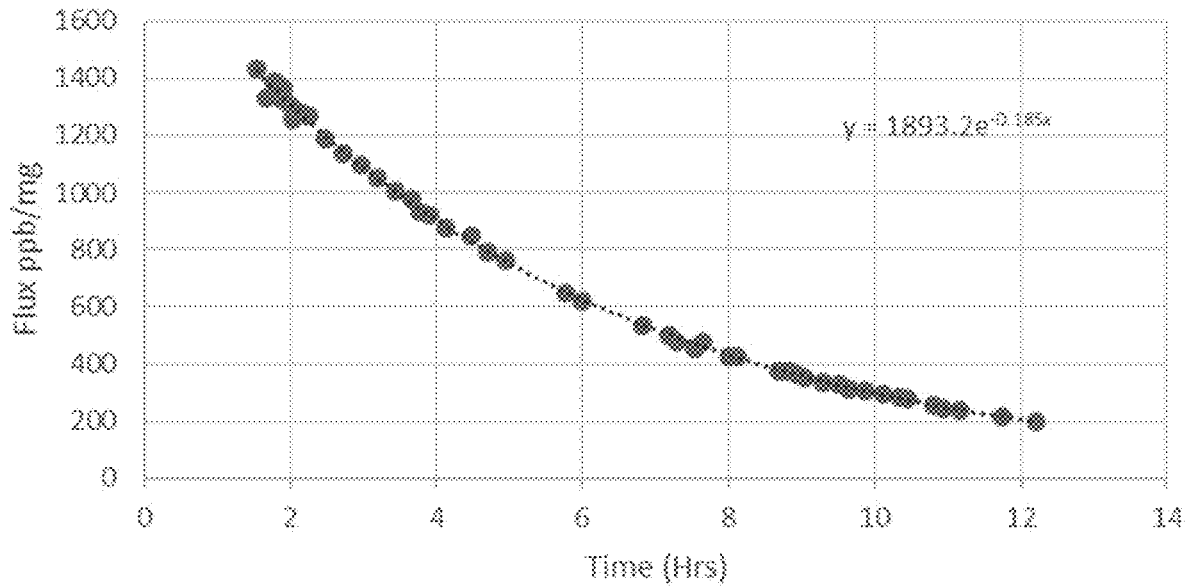
FIG. 9 shows a graphical representation of the nitric oxide analysis (NOA) release profile for compound of Formula III at pH 7.4, as measured by chemiluminescence, showing 6.7 µmol NO/mg of material being released with a $T_{1/2}$ of approximately 3.75 h, suggesting release of only a single diazeniumdiolate group, which has a theoretical load of 7.6 µmol NO/mg.
Figure 10:
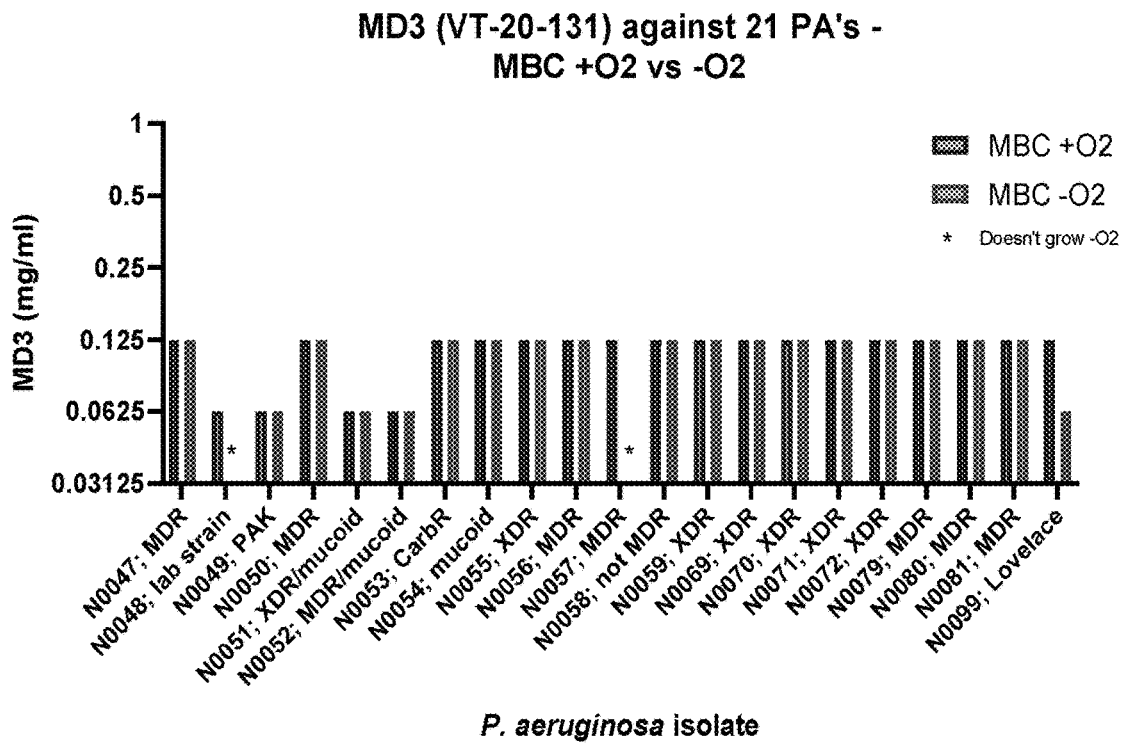
FIG. 10 compares the MBC results for 21 strains of *P. aeruginosa* when grown under aerobic and anaerobic conditions.

The NO release of the compound of Formula III at pH 7.4 is shown in FIG. 9. The release profile was measured by chemiluminescence, showing 6.7 μmol NO/mg material releasing with a $T_{1/2}$ of approximately 3.75 h. In keeping with the described degradation pathway, 2 moles of NO are released per 1 mole of Formula III which converts to a theoretical yield of 7.6 μmol NO/mg.

The antibacterial efficacy of the compound of Formula III derived according to the synthesis example against various *Pseudomonas* bacteria strains are set forth in Tables 3-5. The results from testing varying amounts of the compound mixed with a representative excipient (β-cyclodextrin) is set forth in Table 6.

TABLE 3

Antimicrobial data for compound of Formula III.

| Batch | Species | Strain | MIC (mg/ml) | MBC (mg/ml) |
|---|---|---|---|---|
| NCT-19-096 | *Pseudomonas aeruginosa* | ATCC 19143 | 0.049 | 0.049 |
| NCT-19-096 re-slurry | *Pseudomonas aeruginosa* | ATCC 19143 | 0.049 | 0.098 |
| NCT-19-168 | *Pseudomonas aeruginosa* | ATCC 19143 | 0.0625 | 0.0625 |
| NCT-19-168 (acid degraded) | *Pseudomonas aeruginosa* | ATCC 19143 | 0.5 | 1 |

TABLE 4

Antimicrobial data for compound of Formula III.

| Batch | Species | Strain | MBEC-aerobic (mg/ml) |
|---|---|---|---|
| NCT-19-096 re-slurry | *Pseudomonas aeruginosa* | PAK | 0.391 |

TABLE 5

Antimicrobial data for compound of Formula III against *P. aeruginosa*.

| Batch | MIC (mg/ml) | MBC (mg/ml) | MBEC (mg/mL) |
|---|---|---|---|
| Reaction Precipitate | 0.049 | 0.049 | 0.391 |
| Reaction Precipitate BIOC11 mixture | 0.391 | 0.781 | 1.56 |

TABLE 6

The relationship between increasing excipient concentrations on the antimicrobial efficacy of the combined composition of β-cyclodextrin and compound of Formula III (referenced in table as MTDD).

| % MTDD (NCT-19-096) | % β-cyclodextrin | NO-loading (μmol/mg) | MIC against *P. aeruginosa* (mg/ml) |
|---|---|---|---|
| 100 | 0 | 6.7 | 0.049 |
| 90 | 10 | 6.0 | 0.049 |
| 80 | 20 | 5.4 | 0.098 |
| 60 | 40 | 4.0 | 0.098 |
| 40 | 60 | 2.7 | 0.195 |
| 20 | 80 | 1.3 | 0.391 |
| 10 | 90 | 0.7 | 0.781 |
| 0 | 100 | 0.0 | >6.25 |

Example 2: In Vitro Antimicrobial Activity of the Compound of Formula III Against *P. aeruginosa*

Minimum Inhibitory Concentration/Minimum Bactericidal Concentration (MIC/MBC) assays were performed using the CLSI method to evaluate efficacy of the compound of Formula III against several lab and clinical isolates of *P. aeruginosa*.

As used herein, the Minimum Bactericidal Concentration (MBC) is defined as the lowest concentration of antibiotic that kills 99.9% of the bacteria, and the Minimum Inhibitory Concentration (MIC) is defined as the lowest concentration of an antimicrobial ingredient or agent that is bacteriostatic (prevents the visible growth of bacteria).

MICs are used to evaluate the antimicrobial efficacy of various compounds by measuring the effect of decreasing concentrations of antibiotic/antiseptic over a defined period in terms of inhibition of microbial population growth. These evaluations can be quite useful during the R&D phase of a product to determine appropriate concentrations required in the final product.

Various concentrations of the compounds are inoculated with cultured bacteria, and the results are measured using agar dilution or broth dilution (macro or micro) to determine at what level the MIC endpoint is established.

The Minimum Bactericidal Concentration (MBC) can be determined from the broth dilution of MIC tests by subculturing to agar plates that do not contain the test agent and incubating for 24 hours. The MBC is identified by determining the lowest concentration of antibacterial agent that reduces the viability of the initial bacterial inoculum by a pre-determined reduction such as ≥99.9%. The MBC is complementary to the MIC; whereas the MIC test demonstrates the lowest level of antimicrobial agent that greatly inhibits growth, the MBC demonstrates the lowest level of antimicrobial agent resulting in microbial death. In other words, if a MIC shows inhibition, plating the bacteria onto agar might still result in organism proliferation because the antimicrobial did not cause death. Antibacterial agents are usually regarded as bactericidal if the MBC is no more than four times the MIC.

The Clinical and Laboratory Standards Institute (CLSI) has established protocols and standards for establishing MIC and MBC in products. A common methodology utilized for MIC is CLSI M07-A9, Methods for Dilution Antimicrobial Susceptibility Tests for Bacteria That Grow Aerobically. CLSI also has developed methods specific for the yeasts, filamentous fungi, and anaerobic bacteria. For MBC determination, CLSI M26-A, Methods for Determining Bactericidal Activity of Antimicrobial Agents, is an accepted industry standard.

As shown in Table 7, the compound of Formula III (referenced as MD3 in the table) was effective against all 9 strains tested, with 0.125 mg/ml resulting in a 3-log reduction of bacteria (MBC).

TABLE 7

MIC/MBC results for the compound of Formula III against strains of *P. aeruginosa*

| | MD3 (mg/ml) VT-20-110 | | | |
|---|---|---|---|---|
| *P. aeruginosa* Phenotype | MIC, rep 1 | MIC, rep 2 | MBC, rep 1 | MBC, rep 2 |
| PAK WT | 0.125 | 0.0625 | 0.125 | 0.125 |
| MDR, CarbR, TobraR. | 0.063 | 0.125 | 0.125 | 0.125 |
| ATCC, obligate aerobe | 0.063 | 0.063 | 0.125 | 0.125 |

TABLE 7-continued

MIC/MBC results for the compound of Formula III against strains of *P. aeruginosa*

| | MD3 (mg/ml) VT-20-110 | | | |
|---|---|---|---|---|
| *P. aeruginosa* Phenotype | MIC, rep 1 | MIC, rep 2 | MBC, rep 1 | MBC, rep 2 |
| Not MDR, CarbS, TobraS. Mucoid | 0.063 | 0.063 | 0.125 | 0.125 |
| XDR, CarbR, TobraI. | 0.063 | 0.063 | 0.125 | 0.125 |
| XDR, CarbR, TobraR. | 0.063 | 0.063 | 0.125 | 0.125 |
| XDR, TobraR, CarbR. | 0.063 | 0.063 | 0.125 | 0.125 |
| XDR, TobraR, CarbR. | 0.063 | 0.063 | 0.125 | 0.125 |
| XDR, TobraR, CarbR. | 0.125 | 0.063 | 0.125 | 0.125 |

MD3 is therefore effective against *P. aeruginosa*, a major pathogen affecting cystic fibrosis patients.

Example 3: Efficacy of the Compound of Formula III In Vitro Against Non-Tuberculosis *Mycobacterium*, *Mycobacterium abscessus*

MIC/MBC assays were performed using the CLSI method described above to evaluate the efficacy of the compound of Formula III against several lab and clinical isolates of *Mycobacterium abscessus*, a common NTM species. As shown below in Table 8, the compound of Formula III was effective against all 9 strains tested, with 1 mg/ml resulting in a 3-log reduction of bacterial survival (MBC).

TABLE 8

Formula III is bactericidal against NTM

| *M. abcessus* | | N0010; Clinical Isolate | | N0016; Clinical Isolate | | N0017; Clinical Isolate | | N0018; Clinical Isolate | |
|---|---|---|---|---|---|---|---|---|---|
| Replicate | Batch | MIC | MBC | MIC | MBC | MIC | MBC | MIC | MBC |
| 1 | VT-20-110 | 0.25 | 1 | 0.25 | 1 | 0.5 | 2 | 0.25 | 1 |
| 2 | VT-20-110 | 0.25 | 1 | 0.25 | 1 | 0.25 | 1 | 0.25 | 1 |

| *M. abcessus* | | N0019; Clinical Isolate | | N0020; Clinical Isolate | | N0046; Ordway | |
|---|---|---|---|---|---|---|---|
| Replicate | Batch | MIC | MBC | MIC | MBC | MIC | MBC |
| 1 | VT-20-110 | 0.25 | 1 | 0.25 | 1 | 0.5 | 1 |
| 2 | VT-20-110 | 0.25 | 1 | 0.25 | 1 | 0.25 | 1 |

The data show that the compound has in vitro efficacy beyond just *P. aeruginosa*.

Example 4: Formula III is a Broad-Spectrum Antimicrobial

MIC/MBC assays were performed using the CLSI method to evaluate efficacy of the compound of Formula III against additional clinical isolates of various pathogens. The results are shown below in Table 9. The compound of Formula III is referenced as MD3 in the table.

TABLE 9

MIC/MBC results for the compound of Formula III for a range of gram-negative and gram-positive bacteria.

| Type | Species | Strain ID | Phenotype | MD3 (mg/ml) VT-20-110 | | | |
| --- | --- | --- | --- | --- | --- | --- | --- |
| | | | | MIC, Rep 1 | MIC, Rep 2 | MBC, Rep 1 | MBC, Rep 2 |
| Gram Neg. | *Acetinobacter baumannii* | N0075 | Carb-R, XDR | 0.063 | 0.063 | 0.25 | 0.25 |
| | *Burkolderia cenocepacia* | N0034 | Clinical Isolate | 0.063 | 0.063 | 0.125 | 0.125 |
| | *Escherichia coli* | N0077 | Carb-R, $3^{rd}$-gen Ceph-R, ESBL+, MDR | 0.125 | 0.125 | 0.25 | 0.25 |
| | *Haemophilus influenzae* | N0097 | Chloramphenicol-R, Tet-R, and Amp-R | 0.125 | 0.125 | 0.125 | 0.25 |
| | *Mycobacterium abcessus* | N0019 | Clinical Isolate | 0.25 | 0.25 | 1 | 1 |
| | *Pseudomonas aeruginosa* | N0049 | PAK WT | 0.125 | 0.0625 | 0.125 | 0.125 |
| Gram Pos. | *Staphylococcus aureus* (MRSA) | N0040 | Clinical isolate; MDR, MRSA, Vanco-S | 0.125 | 0.125 | 0.25 | 0.25 |
| | *Staphylococcus aureus* (MSSA) | N0007 | Wichita; ATCC 29213 | 0.125 | 0.125 | 0.125 | 0.125 |
| | *Streptococcus pyogenes* | N0098 | Erythromycin-R | 0.03125 | 0.03125 | 0.0625 | 0.125 |

The data show that Formula III has broad-spectrum anti-microbial activity.

Example 5: Efficacy In Vitro Against a *P. aeruginosa* Biofilm

*P. aeruginosa* biofilms grown on peg lids of a 96-well plate were exposed to the compound of Formula III for 18-24 h, then biofilms were isolated and surviving bacteria enumerated. The data showed that the compound of Formula III eradicated *P. aeruginosa* biofilms. A concentration of 0.391 mg/ml MD3 was sufficient to eradicate bacteria biofilms (>3-log reduction).

Example 6: Efficacy In Vitro Against *P. aeruginosa* Phenotypes Under Aerobic and Anaerobic Growth Conditions As an extension to the work performed in Example 2, the anti-microbial activity of the compound of Formula III was compared for 21 strains of *P. aeruginosa* under aerobic and anaerobic growth conditions. The results are presented in FIG. 10. Out of the 21 strains tested, the activity of the compound of Formula III was identical for 18 of the strains. Two of the strains could not be compared because those two bateria strains could not be grown under anaerobic conditions. Only one strain showed a difference in susceptibility, but the difference was minimal. Therefore, the compound of Formula III shows very consistent anti-microbial activity to *P. aeruginosa* under both aerobic and anaerobic growth conditions.

Example 7: Efficacy In Vitro—Time Kill Assay

The bactericidal activity of the compound of Formula III was evaluated over time for *P. aeruginosa*. *P. aeruginosa* cultures were grown at 37° C. in either PBS or cation-adjusted Mueller Hinton broth (CAMHB) with varying concentrations of the compound of Formula III, and bacteria were quantified at various timepoints during growth. In PBS, bacteria can survive but have no nutrients to replicate. In CAMHB, bacteria have the nutrients needed to grow and do replicate to high titers with time.

Figure 11A:
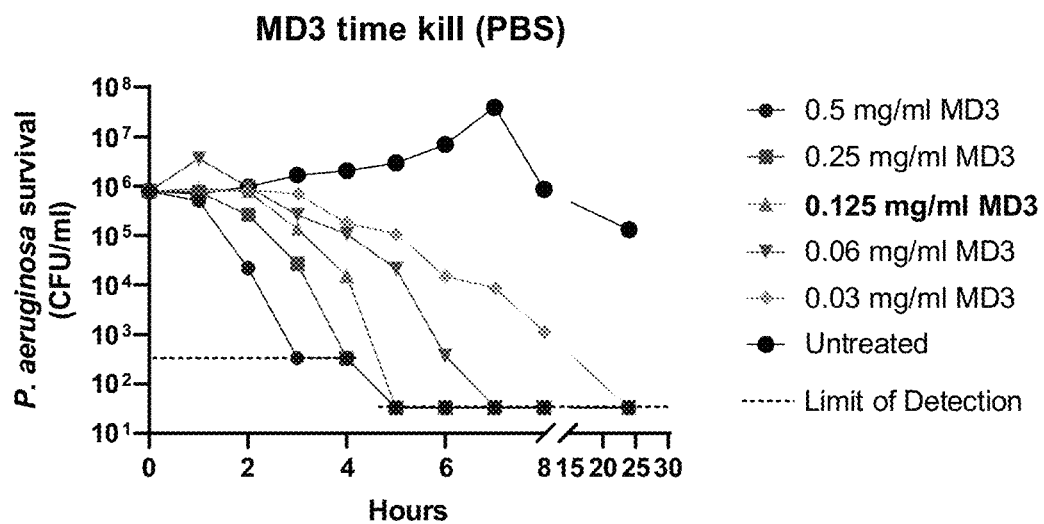
FIGS. 11A and B are graphs showing the dose dependent time kill results of *P. aeruginosa*, in terms of (CFU/ml) versus time (hours), following exposure to the compound of Formula III.
Figure 11B:
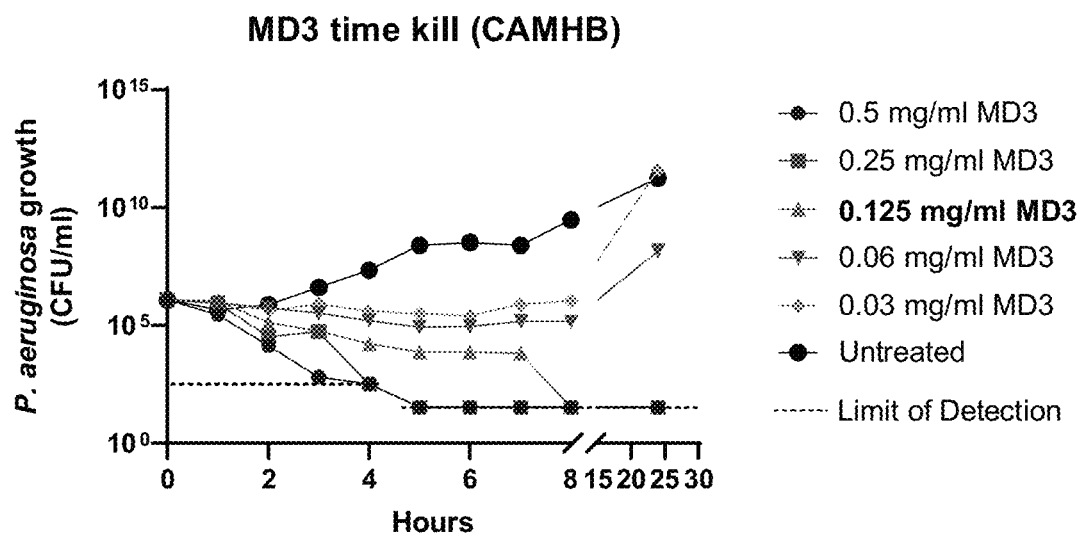

As shown in FIGS. 11A-B, in both PBS and CAMHB, the compound of Formula III (referenced as MD3 in the graphs) eradicated bacteria in a dose- and time-dependent manner. Within the PBS buffer system, the bacteria titers decrease to below the limit of detection for all concentrations of MD3 used but the time required to kill the bacteria increased with decreasing dose. The same trend is observed in the CAMHB system, but because bacteria grow in CAMHB, the lowest two doses of MD3 that were evaluated were insufficient to kill all the bacteria. The bacteria that survived out to 8 hours rapidly reproduced to establish titers close to the untreated control group at 24 hours. All doses greater than or equal to 0.125 mg/ml were effective enough to kill all bacteria within 8 hours; however, the smaller the dose the longer it took to fully kill the bacteria.

Example 8: Nitric Oxide is Key to the Antimicrobial Activity of the Compound of Formula III The activity of the compound of Formula III against *P. aeruginosa* and *S. aureus* was compared with that of its degradation products (referenced as MD3 NO-lib in the table) using the CSLI methods described above. The main degradation product of the compound of Formula III is N-hydroxyl formamide under physiological conditions. In *P. aeruginosa*, the MBC of the compound of Formula III was 64× lower than the MBC of the MD3 NO-lib, and in *S. aureus*, the MBC of MD3 was 16× lower than the MBC of the MD3 OG-lib. The data are shown below in Table 10. The compound of Formula III is referenced as MD3 in the table.

TABLE 10

Comparison of MIC/MBC results for the compound of Formula III and its degraded by-products.

| Species | Strain | MD3 VT-20-110 | | | | MD3 (NO-liberated) VT-20-110 | | | |
| --- | --- | --- | --- | --- | --- | --- | --- | --- | --- |
| | | MIC Rep 1 | MIC Rep 2 | MBC Rep 1 | MBC Rep 2 | MIC Rep 1 | MIC Rep 2 | MBC Rep 1 | MBC Rep 2 |
| *P. aeruginosa* | N0049, PAK, Lab strain | 0.125 | 0.0625 | 0.125 | 0.125 | 2 | 2 | 8 | 8 |
| *S. aureus* | N0040, MRSA, Clinical isolate | 0.125 | 0.125 | 0.25 | 0.25 | 2 | 2 | 4 | 4 |

Since the compound of Formula III functions by releasing NO, and NO-lib does not, it is reasonable to conclude that NO is a significant driver of Formula III's bactericidal activity in vitro.

Figure 12:
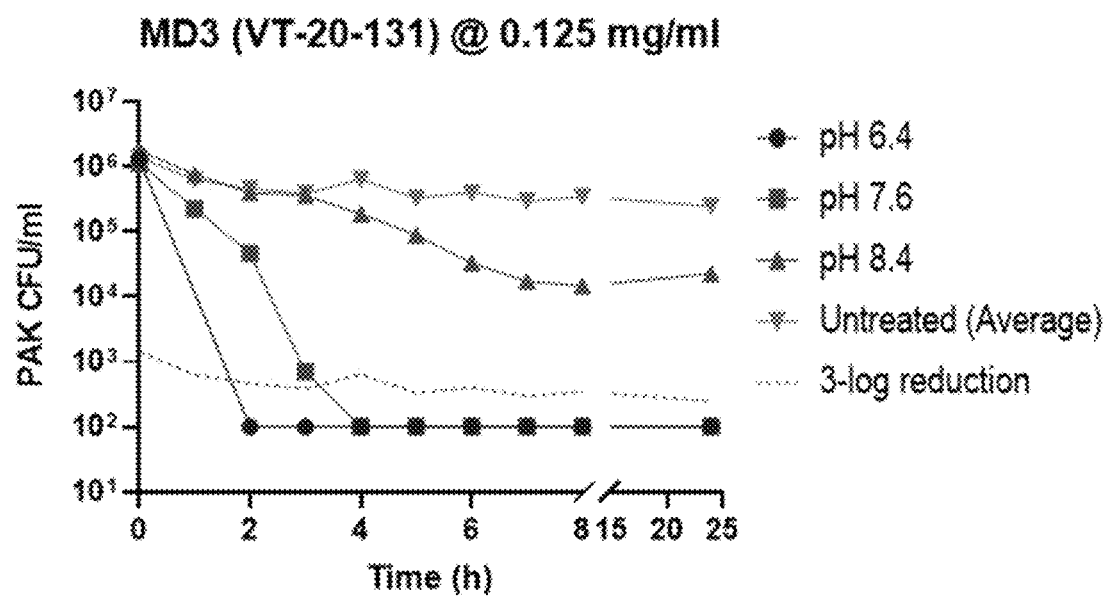
FIG. 12 shows the the effect of pH on the time kill results of *P. aeruginosa* following exposure to the compound of Formula III (0.125 mg/ml).

In support of the key role that NO plays in the antimicrobial activity of the compound of Formula III, a time-kill study was conducted at three different pH conditions: 6.4, 7.6, and 8.4. The rate of NO release is dependent on pH. The lower the pH, the faster the compound of Formula III degrades and releases NO. In turn, the more NO that is released the faster the bacteria are killed. FIG. 12 shows a graph of the time kill assay results which show that bacterial kill rate it dependent on pH. The untreated results are an average of the untreated samples ruan at each pH and show the differences in kill rates is not due to pH itself but due to the differing amounts of NO that are released at each of the time points at the corresponding pH conditions.

Example 9: Animal Toxicology Studies with the Compounds of Formula III

Animal studies were performed using severe, combined, immunodeficient (SCID) mice, using the study design outline in Table 11. No adverse effects were observed even for maximum dose group 6 (100 mg/Kg). All mice remained bright, alert, and responsive throughout the duration of the study.

TABLE 11

Maximum tolerated dose study design carried out in mice.

| | |
| --- | --- |
| Experiment | Maximum tolerated dose (MTD) |
| Test system | 6- to 8-week-old female SCID mice (6 total) |
| Dosing | Intratracheal, once daily for 3 consecutive days |
| Experimental arms | 1. Buffer only |
| | 2. 1 mg/kg MD3 |
| | 3. 3.16 mg/kg MD3 |
| | 4. 10 mg/kg MD3 |
| | 5. 31.6 mg/kg MD3 |
| | 6  100 mg/kg MD3 |
| Readouts | Daily clinical scores, adverse effects, animal weights, survival |

Example 12: Comparison of the Efficacy of MD3 and MD2

In some cases, the synthesis of MD3 also generated an impurity, referred to herein as MD2, or methane bis-diazeniumdiolate, which has the following formula:

The activity of mixtures of these compounds was evaluated against *P. aeruginosa* (PAK), with the goal of determining how the percentage of the compound of Formula III (referenced as MD3 in the table) relative to MD2 in different samples affected the activity of the mixture against *P. aeruginosa*.

TABLE 12

MIC/MBC results for the compound of Formula III of varying purity.

| TA: | Strain: | MIC (mg/ml) | MBC (mg/ml) |
| --- | --- | --- | --- |
| Run #1, vial 7 (97% MD3) | N0049 | 0.0625 | 0.125 |
| Run #2, vial 7 (50% MD3) | N0049 | 0.125 | 0.25 |
| Run #3, vial 7 (5% MD3) | N0049 | 0.25 | 0.5 |

The results, shown in Table 12, demonstrate that the higher the percentage of the compound of Formula III there is in the sample relative to the percentage of MD2, the better the activity is against PAK. It should be noted that when samples have degraded under simulated physiological conditions, that MD2 does not not degrade to any significant degree. Nor does it grow in as a degradation product of the compound of Formula III. Therefore, MD2 does not release NO or HNO when subjected to physiological temperatures and pHs. In the table, where a percentage of MD3 is shown, the balance, adding up to 100%, is predominantly MD2, with minor amounts of other impurities.

Example 13: pH Vs Efficacy of the Compound of Formula III

The efficacy of the compound of Formula III against PAK was evaluated at various pHs, 6.4, 7.6, and 8.4, all of which are physiological pHs, though at different places in the human body. For example, terminal pH in the proximal small bowel ranges from 5.5 to 7.0 and gradually rises to 6.5-7.5 in the distal ileum. There is a decrease in luminal pH from the terminal ileum to the caecum (range 5.5-7.5). The pH in the colon can range from 7.9 to 8.5. A normal blood pH level is 7.40, and this is approximately the pH in the lung. The pH of saliva is ranges from 6.5 to 7.5.

As shown below in FIG. 12, the compound of Formula III at a dosage of 0.125 mg/ml and a pH of 6.4, was sufficient to reduce the concentration of PAK (CFU/ml) from $10^6$ to $10^2$ in two hours, and the concentration stayed at this level for up to 25 hours. In contrast, the compound of Formula III at a dosage of 0.125 mg/ml and a pH of 8.4 was only sufficient to reduce the concentration of PAK (CFU/ml) from $10^6$ to $10^5$ in six hours, and the concentration stayed at this level for up to 25 hours. The compound of Formula III at a dosage of 0.125 mg/ml and a pH of 7.4 was sufficient to reduce the concentration of PAK (CFU/ml) from $10^6$ to $10^2$ in four hours, and the concentration stayed at this level for up to 25 hours. PAK concentrations in untreated control remained at $10^6$ for the entire experiment.

Figure 13:
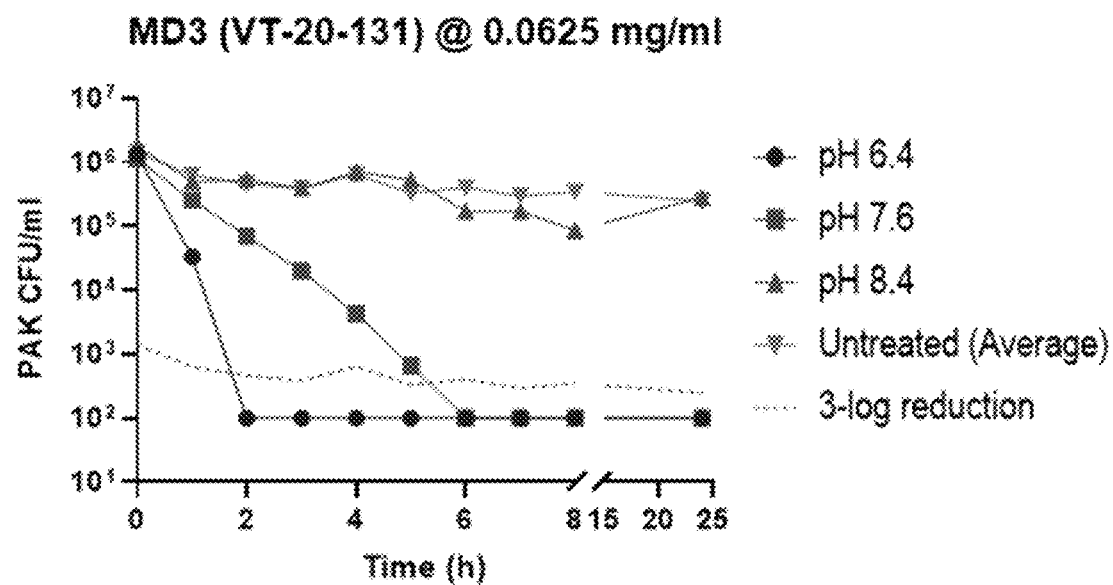
FIG. 13 shows the the effect of pH on the time kill results of *P. aeruginosa* following exposure to the compound of Formula III (0.0625 mg/ml).

As shown below in FIG. 13, when the experiment was repeated, using the compound of Formula III at a dosage of 0.0625 mg/ml and a pH of 6.4, this was sufficient to reduce the concentration of PAK (CFU/ml) from $10^6$ to $10^2$ in two hours, and the concentration stayed at this level for up to 25 hours. In contrast, the compound of Formula III at a dosage of 0.125 mg/ml and a pH of 8.4 was only sufficient to reduce the concentration of PAK (CFU/ml) from $10^6$ to $10^5$ in eight hours, and the concentration returned to $10^6$ at 25 hours. The compound of Formula III at a dosage of 0.125 mg/ml and a pH of 7.4 was sufficient to reduce the concentration of PAK (CFU/ml) from $10^6$ to $10^2$ in six hours, and the concentration stayed at this level for up to 25 hours. PAK concentrations in untreated control remained at $10^6$ for the entire experiment.

Figure 14:
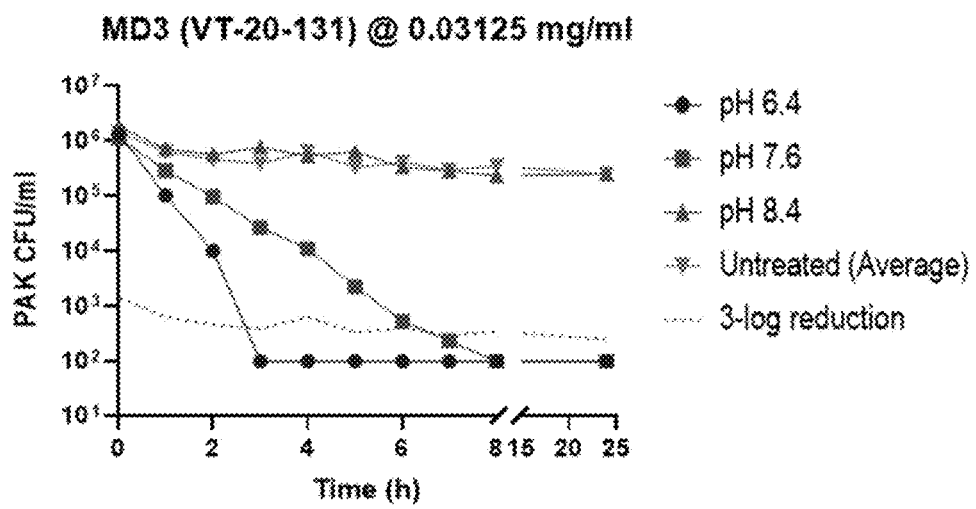
FIG. 14 shows the the effect of pH on the time kill results of *P. aeruginosa* following exposure to the compound of Formula III (0.03125 mg/ml).
Figure 15:
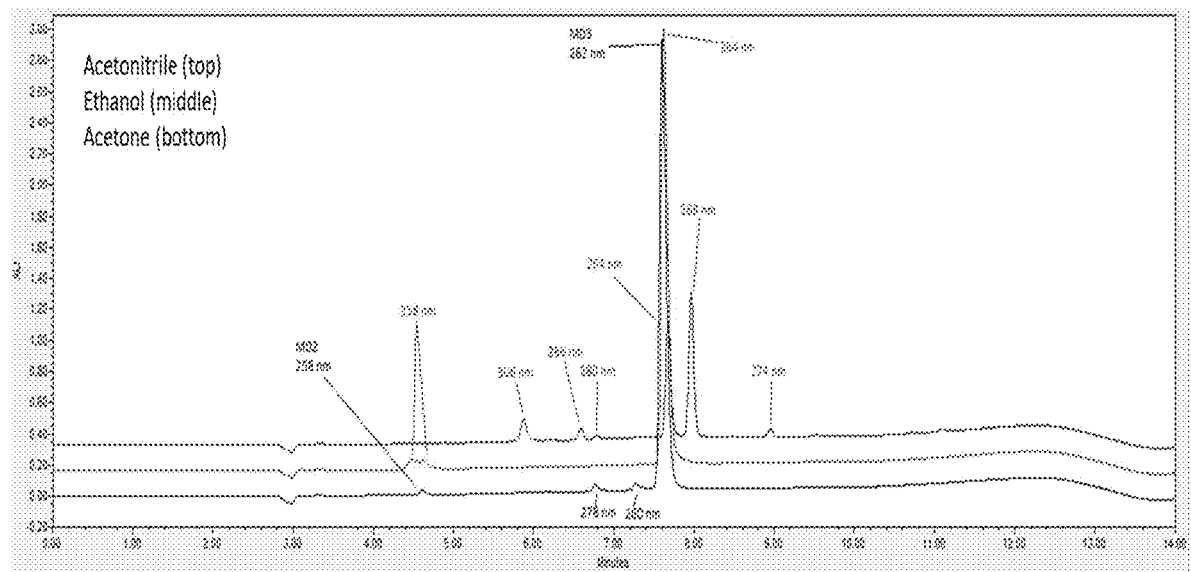
FIG. 15 compares the chromatograms (impurity profiles) of different lots of the compound of Formula III that were manufactured with starting reactants acetonitrile (top), ethanol (middle), and acetone (bottom).

As shown below in FIG. 14, when the experiment was repeated, using the compound of Formula III at a dosage of 0.03125 mg/ml and a pH of 6.4, this was sufficient to reduce the concentration of PAK (CFU/ml) from $10^6$ to $10^2$ in three hours, and the concentration stayed at this level for up to 25 hours. In contrast, the compound of Formula III at a dosage of 0.03125 mg/ml and a pH of 8.4 was insufficient to significantly reduce the concentration of PAK (CFU/ml). MD3 at a dosage of 0.03125 mg/ml and a pH of 7.4 was sufficient to reduce the concentration of PAK (CFU/ml) from $10^6$ to $10^2$ in eight hours, and the concentration stayed at this level for up to 25 hours. PAK concentrations in untreated control remained at $10^6$ for the entire experiment.

Based on the data, a conclusion can be reached that the efficacy of the compound of Formula III is pH-dependent due to the role pH plays on affecting the NO release rate from the compound of Formula III.

Example 14: Comparison of Various Reactants on Purity and Synthetic Process Optimization The compound of Formula III can be prepared using acetone, ethanol or acetonitrile as a starting material as well as other compound with similar functional groups, though when prepared from ethanol or acetonitrile (or any other compound), the impurity profiles for each will be unique. A set of chromatograms are shown of samples of the compound of Formula III prepared from acetone, ethanol, and acetonitrile. In each case a different set of impurities were observed. While the material prepared from ethanol was comparable in purity to the material prepared from acetone (>90% area), the material prepared from acetonitrile was significantly less pure (<40% area).

The process for synthesizing the compound of Formula III starting from acetone was optimized. A series of experiments were run to evaluate the effects of starting acetone concentration (14 vs 30 mg/mL), base equivalents (4 vs 6), NO pressure (2.5 vs 20 bar), and temperature (10 vs 20° C.) on the yield and purity of product produced. Table 13 show the results of the experiments run at an acetone concentration of 14 mg/ml and a temperature of 20° C. for 4 days. Each condition was run in duplicate.

TABLE 13

Compound of Formula III results associated with synthesis conditions.

| Sample | Pressure (bar) | Base Eq (NaOH) | MD2 (Area %) | MD3 (Area %) | NO Total (umol/mg) |
|---|---|---|---|---|---|
| 1 | 2.5 | 4 | 5.0 | 93.3 | 5.5 |
| 2 | | | 3.1 | 95.7 | 5.7 |
| 3 | 2.5 | 6 | 20.4 | 79.0 | 5.7 |
| 4 | | | 16.7 | 82.6 | 5.2 |
| 5 | 20 | 4 | 0.6 | 97.5 | 6.3 |
| 6 | | | 1.0 | 96.2 | 6.1 |
| 7 | 20 | 6 | 2.8 | 94.4 | 5.9 |
| 8 | | | 3.2 | 94.2 | 5.9 |

The best overall conditions identified from these experiments are listed here: an acetone concentration of 14 mg/mL, an NO pressure of 20 bar, and a base equivalent of 4. Temperature had no effect between 10 and 20° C. when run at these conditions. At these conditions, an average purity of ~97% area was achieved with a yield >95%.

Example 15: Comparison of the Antimicrobial Activity of the Compound of Formula III with Other NO Releasing Compounds Other NO donating compounds have been studied for their potential anti-microbial activity. However it can be anticipated that different NO donors will range in their anti-microbial activity due to their varying chemical properties: NO load capacity, NO release rate, water solubility, pKa, molecular weight, etc. Therefore the antimicrobial activity of the compound of Formula III was compared to two other NO donating compounds that were synthesized and characterized in our laboratories: the first was a hepta-substituted ethanolamine β-cyclodextrin compound where all seven secondary amines were functionalized with diazeniumdiolate groups; the second was 2,6-cis-dimethylpiperidine functioned with a group. The results of their antimicrobial activities are shown in Table 14.

TABLE 14

The MIC/MBCs of two NO donors compared to the MIC/MBCs compound of Formula III for various strains of *M. abscessus*.

| | | | *M. abscessus* | | | | | | | | | | | | | |
|---|---|---|---|---|---|---|---|---|---|---|---|---|---|---|---|---|
| | | | N0010; clinical | | N0016; clinical | | N0017; clinical | | N0018; clinical | | N0019; clinical | | N0020; clinical | | N0046 | |
| Compound | NO Load | T1/2 | MIC | MBC | MIC | MBC | MIC | MBC | MIC | MBC | MIC | MBC | MIC | MBC | MIC | MBC |
| β-CD/NO | 4.2 | 0.25 hr | 4 | 16 | 1 | 16 | 1 | 16 | 4 | 16 | 2 | 8 | 4 | 8 | 8 | 16 |
| cis-DMP/NO | 6.9 | 1 hr | 1 | 4 | 2 | 4 | 2 | 4 | 1 | 4 | 2 | 4 | 1 | 2 | 2 | 4 |
| MD3 | 6.7 | 3 hr | 0.25 | 1 | 0.25 | 1 | 0.25 | 1 | 0.25 | 1 | 0.25 | 1 | 0.25 | 1 | 0.25 | 1 |

From the compiled data, it is clear the antimicrobial activity of the compound of Formula III is greater than the antimicrobial activity for either of the other two NO donor molecules. A portion of the increased activity can be attributed to its high NO loading capability, but it is no higher than cis-DMP/NO and yet it four times as effective at killing bacteria. This suggests that the extended NO half-life of the compound of Formula III in comparison to other NO donor compounds plays a critical role as well. The compound of Formula III also releases nitroxyl (HNO) in addition to NO upon degradation at neutral pH conditions. HNO is another reactive nitrogen compound. On its own, nitroxyl will form a dimer with itself which then rearranges to yield one mole of $N_2O$ and one mole of water.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein.

Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above.

Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited.

The methods disclosed herein include certain actions taken by a practitioner; however, they can also include any third-party instruction of those actions, either expressly or by implication. For example, actions such as "administering an NO-donating composition" include "instructing the administration of an NO-donating composition." In addition, where features or aspects of the disclosure are described in terms of Markush groups, those skilled in the art will recognize that the disclosure is also thereby described in terms of any individual member or subgroup of members of the Markush group.

The contents of all documents referred to herein are hereby incorporated by reference for all purposes.

What is claimed is:

1. A method of treating bronchiectasis associated with a pulmonary microbial infection, comprising administering an effective antimicrobial amount of a compound having the formula:

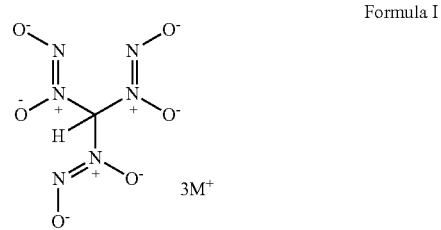

Formula I wherein:
X is selected from the group consisting of H or D,
and $M^+$ is a pharmaceutically-acceptable cation selected from the group consisting of sodium, potassium, lithium, and quaternary ammonium, to a patient in need of treatment thereof,
wherein the compound is present in a composition formulated for pulmonary administration, and
wherein the bronchiectasis is associated with a pulmonary bacterial infection caused by one or more bacteria selected from the group consisting of *Acetinobacter baumannii, Burkolderia cenocepacia, Escherichia coli, Haemophilus influenza, Mycobacterium abcessus, Pseudomonas aeruginosa, Staphylococcus aureus,* and *Streptococcus pyogenes*.

2. The method of claim 1, wherein the compound has the structure of Formula II:

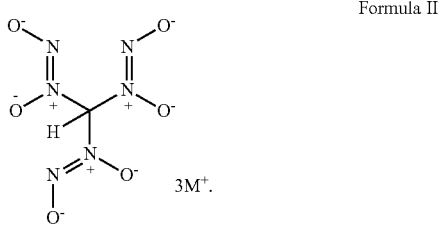

Formula II

3. The method of claim 1, wherein the compound has a purity of greater than 98%.

4. The composition of claim 1, formulated for administration via inhalation, nebulization, or intranasal administration.

5. The composition of claim 1, wherein the compound is present in a microparticle or nanoparticle for pulmonary delivery.

6. The composition of claim 5, wherein the compound is present in an inhaler, in a liquid spray, or in an aerosol.

7. The composition of claim 6, wherein the inhaler is a metered dose inhaler or a dry powder inhaler.

8. The composition of claim 1, wherein the compound is loaded into biodegradable polymeric particles to provide for the controlled-release and delivery of the compound.

9. The composition of claim 1, further comprising a mucoadhesive agent, a chelating agent, or a low molecular weight polyethylene glycol.

10. The composition of claim 9, in the form of a mucoadhesive drug delivery system for pulmonary administration.

11. The composition of claim 1, further comprising one or more additional active agents.

12. The composition of claim 1, further comprising a gallium (III) salt or a siderophore.

13. The composition of claim 12, wherein the gallium salt is gallium nitrate or gallium chloride.

14. The composition of claim 12, wherein the gallium salt is present at a concentration that provides between 0.001 and 100 mg of gallium.

15. The method of claim 1, wherein an effective antimicrobial amount of the compound is between 1 and 100 mg/kg.

* * * * *